(12) United States Patent
Schmidt et al.

(10) Patent No.: US 9,353,078 B2
(45) Date of Patent: May 31, 2016

(54) AMINO, AMIDO AND HETEROCYCLIC COMPOUNDS AS MODULATORS OF RAGE ACTIVITY AND USES THEREOF

(71) Applicants: Ann Marie Schmidt, Franklin Lakes, NJ (US); Ravichandran Ramasamy, Ardsley, NY (US); Alexander Shekhtman, Glenmont, NY (US); Vivek Rai, Allahabad (IN); Michaele B. Manigrasso, New York, NY (US)

(72) Inventors: Ann Marie Schmidt, Franklin Lakes, NJ (US); Ravichandran Ramasamy, Ardsley, NY (US); Alexander Shekhtman, Glenmont, NY (US); Vivek Rai, Allahabad (IN); Michaele B. Manigrasso, New York, NY (US)

(73) Assignees: New York University, New York, NY (US); The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/503,919

(22) Filed: Oct. 1, 2014

(65) Prior Publication Data
US 2015/0094307 A1   Apr. 2, 2015

Related U.S. Application Data

(60) Provisional application No. 61/885,183, filed on Oct. 1, 2013, provisional application No. 61/885,176, filed on Oct. 1, 2013.

(51) Int. Cl.
| | |
|---|---|
| A61K 31/535 | (2006.01) |
| C07D 319/20 | (2006.01) |
| C07D 213/75 | (2006.01) |
| C07D 277/28 | (2006.01) |
| C07D 239/42 | (2006.01) |

(52) U.S. Cl.
CPC ............ *C07D 319/20* (2013.01); *C07D 213/75* (2013.01); *C07D 239/42* (2013.01); *C07D 277/28* (2013.01)

(58) Field of Classification Search
USPC ...................... 514/235.8, 352, 370
See application file for complete search history.

(56) References Cited

U.S. PATENT DOCUMENTS

| | | | |
|---|---|---|---|
| 7,361,678 B2 | 4/2008 | Mjalli et al. | |
| 2003/0013770 A1 | 1/2003 | Ottosen | |
| 2004/0110832 A1 | 6/2004 | Mjalli et al. | |
| 2009/0088406 A1 | 4/2009 | Kurimura et al. | |
| 2010/0119512 A1 | 5/2010 | Feener et al. | |
| 2010/0249038 A1 | 9/2010 | Logsdon et al. | |
| 2010/0254983 A1 | 10/2010 | Schmidt et al. | |
| 2011/0015217 A1* | 1/2011 | McKnight et al. | ............ 514/275 |
| 2012/0088778 A1 | 4/2012 | Mjalli et al. | |
| 2012/0252818 A1 | 10/2012 | Chiosis et al. | |

FOREIGN PATENT DOCUMENTS

| | | |
|---|---|---|
| WO | 2007089616 | 8/2007 |
| WO | 2009029617 | 3/2009 |
| WO | 2009051804 | 4/2009 |
| WO | 2012119035 | 9/2012 |

OTHER PUBLICATIONS

McKnight et al. CAS: 162: 8526, 2014.*
Hudson et al., "Interaction of the RAGE cytoplasmic domain with diaphanous-1 Is required for ligand-stimulated cellular migration through activation of Rac1 and Cdc42", The Journal of Biological Chemistry, 2008, 283:34457-34468.
Rai et al., "Signal transduction in receptor for advanced glycation end products (RAGE) solution structure of c-terminal RAGE (ctRAGE) and its binding to mDia1", The Journal of Biological Chemistry, 2012, 287:5133-5144.
Toure et al., "Formin mDia1 mediates vascular remodeling via integration of oxidative and signal transduction Pathways", Circulation Research, 2012, 110:1279-1293.
Xu et al., "Advanced glycation end product (AGE)-receptor for AGE (RAGE) signaling and up-regulation of Egr-1 in hypoxic macrophages", The Journal of Biological Chemistry, 2010, 285:23233-23240.
Yan et al., "The RAGE axis: a fundamental mechanism signaling danger to the vulnerable vasculature", Circ Res, 2010, 106:842-853.
Yan et al., "Tempering the wrath of RAGE: an emerging therapeutic strategy against diabetic complications, Neurodegeneration and Inflammation", Ann Med, 2009, 41:408-422.
PubChem CID 14570, 2005, Retrieved from the Internet, http://pubchem.ncbi.nlm.nih.gov/compound/14570.
Schmidt et al., "Activation of Receptor for Advanced Glycation End Products A Mechanism for Chronic Vascular Dysfunction in Diabetic Vasculopathy and Atherosclerosis", Circulation Research, 1999, 84:489-197.
Bucciarelli et al., "RAGE Blockade Stabilizes Established Atherosclerosis in Diabetic Apolipoprotein E-Null Mice", Circulation, 2002, 106:2827-2835.
Naka et al., "RAGE Axis Animal Models and Novel Insights Into the Vascular Complications of Diabetes", Arterioscler Thromb Vasc Biol, 2004, 24:1342-1349.

(Continued)

*Primary Examiner* — Rei-Tsang Shiao
(74) *Attorney, Agent, or Firm* — Klauber & Jackson LLC

(57) ABSTRACT

Amino, amido, and heterocyclic compounds are disclosed. The compounds may be prepared as pharmaceutical compositions, and may be used for the prevention and treatment of a variety of conditions in mammals including humans, including by way of non-limiting example, diabetes complications, inflammation, and neurodegeneration, obesity, cancer, ischemia/reperfusion injury, cardiovascular disease and other diseases related to RAGE activity.

21 Claims, 10 Drawing Sheets

(56) References Cited

OTHER PUBLICATIONS

Wendt et al., "RAGE modulates vascular inflammation and atherosclerosis in a murine model of type 2 diabetes", Atherosclerosis, 2006, 185:70-77.
Cuccurullo et al., "Suppression of Rage as a Basis of Simvastatin-Dependent Plaque Stabilization in Type 2 Diabetes", Arterioscler Thromb Vasc Biol., 2006, 26: 2716-2723.
Singh et al., "Advanced Glycation End Products and Diabetic Complications", Korean J Physiol Pharmacol, 2014, 18:1-14.
Lee et al., "Receptor for Advanced Glycation Endproducts (RAGE), Its Ligands, and Soluble RAGE: Potential Biomarkers for Diagnosis and Therapeutic Targets for Human Renal Diseases", Genomics Inform, 2013,11:224-229.
Aleshin et al., "RAGE modulates myocardial injury consequent to LAD infarction via impact on JNK and STAT signaling in a murine model", Am J Physiol Heart Circ Physiol, 2008, 294: H1823-H1832.
Bucciarelli et al., "Receptor for Advanced-Glycation End Products Key Modulator of Myocardial Ischemic Injury", Circulation, 2006, 113:1226-1234.
Bucciarelli et al., "RAGE and Modulation of Ischemic Injury in the Diabetic Myocardium", Diabetes, 2008, 57:1941-1951.
Taguchi et al., "Blockade of RAGE±amphoterin signalling suppresses tumour growth and metastases", Nature, 2000, 405:354-360.
Malik et al., "Role of receptor for advanced glycation end products in the complication and progression of various types of cancers", Biochimica et Biophysica Acta, 2015, 1850:1898-1904.
Boone et al., "The receptor for advanced glycation end products (RAGE) enhances autophagy and neutrophil extracellular traps in pancreatic cancer", Cancer Gene Therapy, 2015, 22:326-334.
Hsieh et al., "Expression analysis of S100 proteins and RAGE in human tumors using tissue microarrays", Biochemical and Biophysical Research Communications, 2003, 307:375-381.
Hoffman et al., "RAGE Mediates a Novel Proinflammatory Axis: A Central Cell Surface Receptor for S100/Calgranulin Polypeptides", Cell, 1999, 97:889-901.
Chavakis et al, "The Pattern Recognition Receptor (RAGE) Is a Counterreceptor for Leukocyte Integrins: A Novel Pathway for Inflammatory Cell Recruitment", J. Exp. Med., 2003, 198:1507-1515.
Cecil et al., "Inflammation-Induced Chondrocyte Hypertrophy Is Driven by Receptor for Advanced Glycation End Products", The Journal of Immunology, 2005, 175:8296-8302.
Oczypok et al., "Pulmonary receptor for advanced glycation endproducts promotes asthma pathogenesis through IL-33 and accumulation of group 2 innate lymphoid cells", J Allergy Clin Immunol, 2015, 136:747-756.
Akirav et al., "The Receptor for Advanced Glycation End Products (RAGE) Affects T Cell Differentiation in OVA Induced Asthma", PLoS One, 2014, 9:e95678.
Ullah et al., "Receptor for advanced glycation end products and its ligand high-mobility group box-1 mediate allergic airway sensitization and airway inflammation", J Allergy Clin Immunol, 2014, 134:440-50.
Zhou et al., "HMGB1 and RAGE levels in induced sputum correlate with asthma severity and neutrophil percentage", Human Immunology, 2012, 73:1171-1174.
Song et al., "RAGE Regulates the Metabolic and Inflammatory Response to High-Fat Feeding in Mice", Diabetes, 2014, 63:1948-1965.
Christaki et al., "Receptor for advanced glycation end products in bacterial infection: is there a role for immune modulation of receptor for advanced glycation end products in the treatment of sepsis?", Curr Opin Infect Dis, 2012, 25:304-311.
van Zoelen et al., "The Receptor for Advanced Glycation End Products Impairs Host Defense in Pneumococcal Pneumonia1", The Journal of Immunology, 2009, 182:4349-4356.
Ekong et al., "Blockade of the receptor for advanced glycation end products attenuates acetaminophen-induced hepatotoxicity in mice", Journal of Gastroenterology and Hepatology, 2006, 21:682-688.
Zeng et al., "Blockade of Receptor for Advanced Glycation End Product (RAGE) Attenuates Ischemia and Reperfusion Injury to the Liver in Mice", Hepatology, 2004, 39:422-432.
Cataldegirmen et al., "RAGE limits regeneration after massive liver injury by coordinated suppression of TNF-and NF-B", J Exp Med, 2005, 201:473-484.
Zeng et al., "Opposing roles of RAGE and Myd88 signaling in extensive liver resection", FASEB J., 2012, 26:882-893.
Miyata et al. , "The Receptor for Advanced Glycation End Products (RAGE) Is a Central Mediator of the Interaction of AGEb 2 Microglobulin with Human Mononuclear Phagocytes Via an Oxidant-sensitive Pathway", J. Clin. Invest., 1996, 98:1088-1094.
Yan et al., "Receptor-dependent cell stress and amyloid accumulation in systemic amyloidosis", Nature Medicine, 2000, 6:643-651.
Sousa et al., "Familial Amyloid Polyneuropathy: Receptor for Advanced Glycation End Products-Dependent Triggering of Neuronal Inflammatory and Apoptotic Pathways", The Journal of Neuroscience, 2001, 21:7576-7586.
Röcken et al., "Advanced Glycation End Products and Receptor for Advanced Glycation End Products in AA Amyloidosis", American Journal of Pathology, 2003, 162:1213-1220.
Mezentsev et al., "Pharmacological Control of Receptor of Ddvanced Glycation End-Products and its Biological Effects in Psoriasis", Int J Biomed Sci, 2013, 9:112-122.
Shubbar et al., "Psoriasin (S100A7) increases the expression of ROS and VEGF and acts through RAGE to promote endothelial cell proliferation", Breast Cancer Res Treat, 2012, 134:71-80.
Turovskaya et al., "RAGE, carboxylated glycans and S100A8/A9 play essential roles in colitis-associated carcinogenesis", Carcinogenesis, 2008, 29:2035-2043.
Hofmann et al., "RAGE Mediates a Novel Proinflammatory Axis: A Central Cell Surface Receptor for S100/Calgranulin Polypeptides", Cell, 1999, 97:889-901.
Sun et al, "Immune complexes activate human endothelium involving the cell-signaling HMGB1-RAGE axis in the pathogenesis of lupus vasculitis", Laboratory Investigation, 2013, 93:626-638.
Nadatani et al, "High-Mobility Group Box 1 Inhibits Gastric Ulcer Healing through Toll-Like Receptor 4 and Receptor for Advanced Glycation End Products", PLoS One, 2013, 8:e80130.
Gugliucci et al., "The Axis AGE-RAGE-Soluble RAGE 14 and Oxidative Stress in Chronic Kidney Disease", Advances in Experimental Medicine and Biology, 2014, 191-208.
Gray et al., "The pathobiology of diabetic vascular complications—cardiovascular and kidney disease", J Mol Med, 2014, 92:441-452.
Fukami et al., "Receptor for advanced glycation endproducts and progressive kidney disease", Curr Opin Nephrol Hypertens, 2015, 24:54-60.
Creager et al., "Diabetes and Vascular Disease Pathophysiology, Clinical Consequences, and Medical Therapy: Part I", Circulation, 2003; 108:1527-1532.
Gkogkolou et al., "Advanced glycation end products Key players in skin aging?", Dermato-Endocrinology, 2012, 4:259-270.
Tian et al., "The Relationship Between Inflammation and Impaired Wound Healing in a Diabetic Rat Burn Model", J Burn Care Res DOI: 10.1097/BCR.0000000000000171, 2004.
Kim et al., "Thymosin beta 4 improves dermal burn wound healing via downregulation of receptor of advanced glycation end products in db/db mice", Biochimica et Biophysica Acta 2014, 840:3452-3459.
Zhang et al., "Role of High Mobility Group Box 1 (HMGB1) in Wound Healing", Journal of Surgical Research, 2012, 176:343-347.
Yamamoto et al. ,"Controlling the receptor for advanced glycation end-products to conquer diabetic vascular ,mmplic.ations", Journal of Diabetes Investigation, 2012, 3:107-114.
Kikuchi et al., "Potential of the Angiotensin Receptor Blockers (ARBs) Telmisartan, Irbesartan, and Candesartan for Inhibiting the HMGB1/RAGE Axis in Prevention and Acute Treatment of Stroke", Int. J. Mol. Sci., 2013, 14:18899-18924.
Winden et al., "Antenatal exposure of maternal secondhand smoke (SHS) increases fetal lung expression of RAGE and induces RAGE-mediated pulmonary inflammation", Respiratory Research, 2014, 15:129.

(56) References Cited

OTHER PUBLICATIONS

Wood et al., "Acute secondhand smoke-induced pulmonary inflammation is diminished in RAGE knockout mice", Am J Physiol Lung Cell Mol Physiol, 2014, 307: L758-L764.

Barton et al., "Primary alveolar macrophages exposed to diesel particulate matter increase RAGE expression and activate RAGE signaling", Cell Tissue Res, 2014, 358:229-238.

Collison et al., RAGE-mediated neutrophil dysfunction is evoked by advanced glycation end products (AGEs), J. Leukoc. Biol., 2002, 71:433-444.

Achouiti et al., "The receptor for advanced glycation end products promotes bacterial growth at distant body sites in *Staphylococcus aureus* skin infection", Microbes and Infection, 2015, 17:622-627.

Lutterloh et al., "Inhibition of the RAGE products increases survival in experimental models of severe sepsis and systemic infection", Critical Care, 2007, 11:R122.

* cited by examiner

Comp#2-RAGE tail Fluorescence Titration

Comp#4-Rage-tail Fluorescence

Figure 7

Test Compound Dissociation

| Compound | Dissociation Constant | Group |
|---|---|---|
| 1 | 4 ± 1 nM | Lead Series II-1 |
| 2 | 6.5 ± 1 nM | Singleton |
| 3 | 18 ± 4 nM | Lead Series I-3 |
| 4 | 2 ± 1 nM | Lead Series I-4 |
| 5 | 1.1 ± 0.2 nM | Singleton |
| 6 | 0.1 ± 0.05 nM | Lead Series II-6 |
| 7 | 0.55 ± 0.05 nM | Singleton |
| 8 | 2 ± 0.5 nM | Lead Series II-8 |
| 9 | 17.3 ± 0.5 µM | Singleton |
| 10 | 3 ± 1 nM | Singleton |
| 11 | 1.2 ± 0.5 nM | Singleton |
| 12 | 0.6 ± 0.1 nM | Singleton |
| 13 | 123 ± 1 nM | Lead Series II-13 |
| 14 | 1.4 ± 0.3 nM | Lead Series II-14 |

Effect of Compounds 1-14 on CML-AGE-Induced Migration in Murine Aortic Smooth Muscle Cells Concentration= 1μm Effect of Compounds 1-14 on CML-AGE-Induced Migration in Human Aortic Smooth Muscle Cells

Figure 10

Effect of Compounds 1-14 on Delayed Type Hypersensitivity (DTH) in Mice: Effects on Inflammation

- Female CF-1 mice (6 wks of age) were sensitized with methylated BSA.
- After 21 days, compounds were injected twice daily for two days (5mg/kg by IP).
- Following the final compound injection, the left plantar hind paw was injected subcutaneously with mBSA.
- The following morning, animals were assessed using a semi-quantitative clinical scoring method (0-5).

| Significant decrease in inflammation | Moderate decrease in inflammation | No decrease in inflammation |
|---|---|---|
| Compound 3 | Compound 4 | Compound 1 |
| Compound 12 | Compound 6 | Compound 2 |
|  | Compound 10 | Compound 5 |
|  |  | Compound 7 |
|  |  | Compound 8 |
|  |  | Compound 9 |
|  |  | Compound 11 |
|  |  | Compound 13 |
|  |  | Compound 14 |

AMINO, AMIDO AND HETEROCYCLIC COMPOUNDS AS MODULATORS OF RAGE ACTIVITY AND USES THEREOF

CROSS REFERENCE TO RELATED APPLICATIONS

This application claims priority under 35 USC §119(e) from U.S. Provisional Application Ser. Nos. 61/885,176 and 61/885,183, which were filed Oct. 1, 2013, each of which applications is herein specifically incorporated by reference in its entirety.

GOVERNMENTAL SUPPORT

The research leading to the present invention was funded in part by NIH grant 1R24DK103032-01. The United States government has certain rights in the invention.

FIELD OF THE INVENTION

This invention relates to amino, amido, and heterocyclic compounds capable of modulating the receptor for advanced glycation end products (RAGE) activity. Specifically, this invention relates to amino, amido, and heterocyclic compounds capable of modulating the interaction of RAGE and its ligands, and uses of such compounds to treat diseases or conditions related to RAGE activity. More particularly, the amino, amido, and heterocyclic compounds may be used to treat diabetes complications, inflammation, and neurodegeneration, obesity, cancer, ischemia/reperfusion injury, cardiovascular disease and other diseases related to RAGE activity. Also encompassed herein, are compositions of amino, amido, and heterocyclic compounds, pharmaceutical compositions of amino, amido, and heterocyclic compounds, and assays and methods for using same to identify compounds capable of modulating RAGE activity.

BACKGROUND OF THE INVENTION

The receptor for advanced glycation end products (RAGE) is a multiligand cell surface macromolecule that plays a central role in the etiology of diabetes complications, obesity, inflammation, cancer and neurodegeneration. The cytoplasmic domain of RAGE, C terminal RAGE or ctRAGE (RAGE tail) is critical for RAGE-dependent signal transduction. As the most membrane proximal event, mDia1 binds to RAGE and is essential for RAGE ligand-stimulated phosphorylation of kinases and cellular properties such as AKT and cell proliferation/migration of smooth muscle cells; activation of cdc42 and rac 1 in smooth muscle cells and transformed cells; and upregulation of early growth response 1 in hypoxic macrophages, as examples. RAGE contains an unusual α-turn that mediates the mDia1-RAGE interaction and is required for RAGE dependent signaling (Shekhtman et al, *J. Bio. Chem.*, 2012, 287(7) 5133-5142).

RAGE-ligand interactions evoke central changes in cellular properties including stimulation of cellular migration and proliferation and leading to such pathological conditions as diabetes and its complications, Alzheimer's disease, inflammation and cancers. RAGE also plays a pivotal role in the atherosclerotic process (Schmidt, et al. (1999) *Circ Res* 84, 489-497). Thus, inhibition of the RAGE activity is desirable for treatment of these conditions.

US application publication, US2012/0088778 discloses azole derivatives as modulators of the interaction of RAGE and its ligands or RAGE activity. The azole compounds are reported to be useful for treatment of diseases including acute and chronic inflammation, the development of diabetic late complications, and others.

US application publication, US2010/0254983 discloses methods for treating obesity using antagonists of binding of RAGE ligands to RAGE.

US application publication, US2010/0119512 discloses carboxamide derivatives as modulators of the interaction of RAGE and its ligands or RAGE activity.

U.S. Pat. No. 7,361,678 discloses composition of 3,5-diphenyl-imidazole derivatives as modulators of the interaction of RAGE and its ligands or RAGE activity.

International application publication, WO2007/089616, discloses tertiary amides as modulators of the interaction of RAGE and its ligands or RAGE activity.

US application publication, US2010/0249038, discloses novel peptides as antagonists of RAGE.

Many or most of the ligands disclosed in the above applications bind to the extracellular domain of RAGE.

In view of the above, a need exists for therapeutic agents, and corresponding pharmaceutical compositions and related methods of treatment that address conditions causally related to RAGE activity, and it is toward the fulfillment and satisfaction of that need, that the present invention is directed.

SUMMARY OF THE INVENTION

The present invention provides amino, amido, and heterocyclic compounds capable of modulating the receptor for advanced glycation end products (RAGE) activity.

Specifically, the invention provides amino, amido, and heterocyclic compounds capable of modulating the interaction of RAGE and its ligands, and uses of such compounds to treat diseases or conditions related to RAGE activity.

More specifically, the invention provides amino, amido, and heterocyclic compounds capable of modulating the interaction of RAGE and its ligands binding to the intracellular domain of the RAGE, and uses of such compounds to treat diseases or conditions related to RAGE activity.

In one aspect, the present invention provides a method for preventing, treating or ameliorating in a mammal a disease or condition that is causally related to RAGE activity in vivo, which comprises administering to the mammal an effective disease-treating or condition-treating amount of a compound according to formula A-Ia or A-Ib:

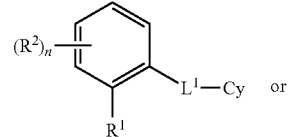

A-Ia

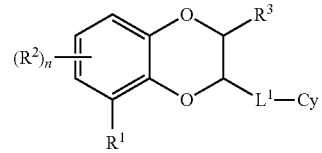

A-Ib wherein
$L^1$ is —NH—, —$CH_2$—NH—, —$CH_2$—$CH_2$—NH—, —CO—NH— or —CO—NH-$L^2$-CO—NH—; and
Cy is substituted or unsubstituted aryl or substituted or unsubstituted heteroaryl; or L¹ is a bond and Cy is

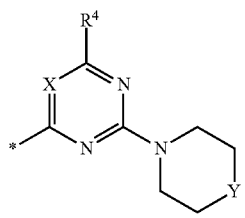

R¹ is H, substituted or unsubstituted $C_1$-$C_6$ alkyl, substituted or unsubstituted $C_1$-$C_6$ alkoxy, or halo;
each R² is independently selected from OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or two adjacent R¹ and R² groups may join together to form a substituted or unsubstituted carbocyclic or heterocyclic ring;
R³ is H, or substituted or unsubstituted $C_1$-$C_6$ alkyl;
the subscript n is 0, 1, 2, or 3;
L² is $C_1$-$C_3$ alkylene;
X is CH or N; Y is O or NR⁵;
R⁴ is substituted or unsubstituted alkyl, substituted or unsubstituted cycloalkyl,
substituted or unsubstituted aryl, or substituted or unsubstituted heteroaryl;
R⁵ is H or substituted or unsubstituted alkyl; and * represents an attachment point;
or a pharmaceutically acceptable salt, solvate or prodrug thereof;
and stereoisomers, isotopic variants and tautomers thereof.
In one embodiment, with respect to the compound of formula A-Ia, the compound is according to formula A-II, A-III, A-IV, A-V, A-VI, A-VII:

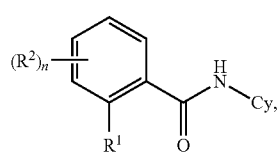

A-II

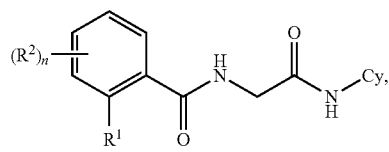

A-III

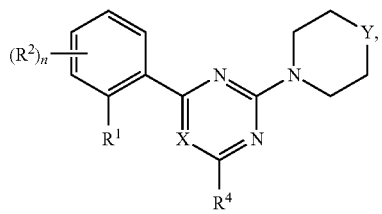

A-IV

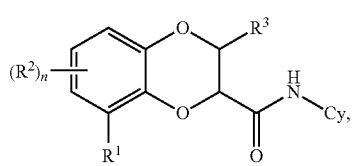

A-V

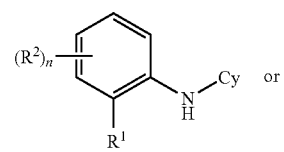

A-VI

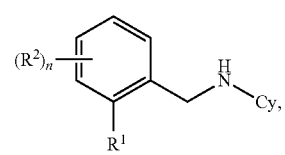

A-VII wherein Cy, X, Y, R¹, R², R⁴, and n are as described for formula A-Ia.

In one embodiment, with respect to the compound of formula A-Ib, the compound is according to formula A-V:

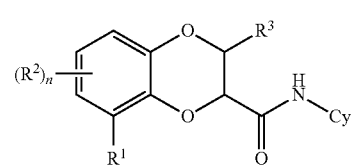

A-V wherein Cy, X, Y, R¹, R², R³, and n are as described for formula A-Ib.

In one particular embodiment, with respect to the compound of formula A-Ia or A-Ib, the compound is according to formula A-XIVa, A-XIVb, A-XIVc, A-XIVd, A-XV, A-XVIb, or A-XXb.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-I':

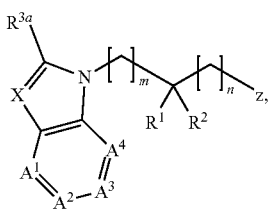

wherein each $A^1$, $A^2$, $A^3$, $A^4$, X, Z, $R^1$, $R^2$, and $R^{3a}$ are as described herein.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-I:

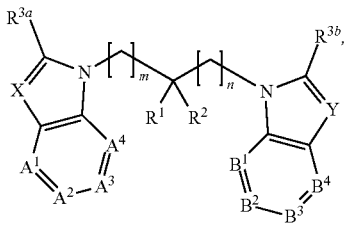

wherein
each $A^1$, $A^2$, $A^3$, $A^4$, $B^1$, $B^2$, $B^3$, and $B^4$, is independently $CR^4$ or N; provided that only 1 or 2 of $A^1$, $A^2$, $A^3$, and $A^4$ are N, and only 1 or 2 of $B^1$, $B^2$, $B^3$, and $B^4$ are N at any one time;

X is $CR^{5a}$ or N; X is $CR^{5b}$ or N;

$R^1$ is hydroxy, substituted hydroxyl, amino, or substituted amino;

$R^2$ is H, alkyl or aryl;

each $R^{3a}$ and $R^{3b}$ is independently H, substituted or unsubstituted alkyl, substituted or unsubstituted cycloalkyl, substituted or unsubstituted aryl, halo, or cyano;

each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;

$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring;

$R^{5b}$ is independently H, substituted or unsubstituted alkyl, substituted or unsubstituted cycloalkyl, substituted or unsubstituted aryl, halo, or cyano; or $R^{5b}$ and $R^{3b}$ may join together to form a substituted or unsubstituted carbocyclic or heterocyclic ring; and each of the subscript m and n is independently 1, 2, or 3;

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-II:

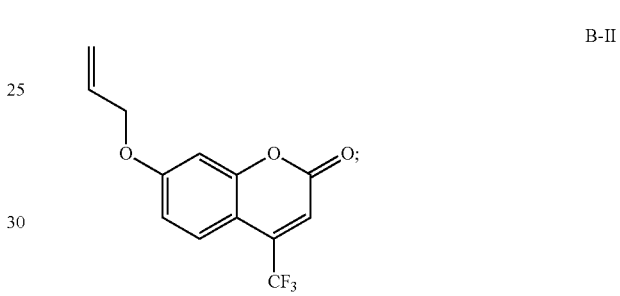

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-III:

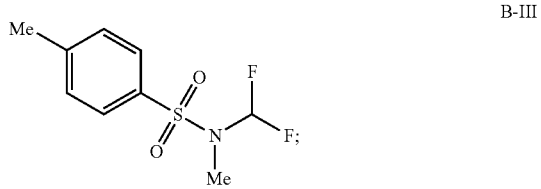 [SMILES: Cc1ccc(S(=O)(=O)N(C)C(F)F)cc1]

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-IV:

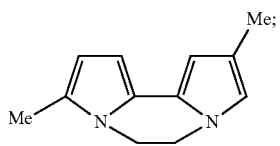

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-V:

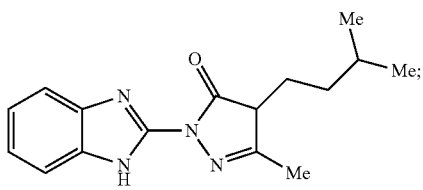

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-VI:

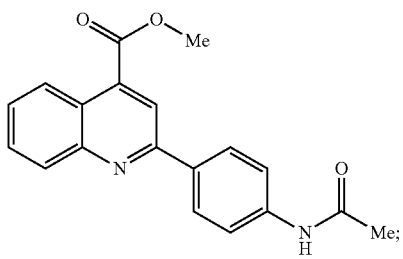

or a pharmaceutically acceptable salt, solvate or prodrug thereof;

or stereoisomers, isotopic variants and tautomers thereof.

In one embodiment, with respect to the compound of formula B-I, the compound is according to formula B-XId:

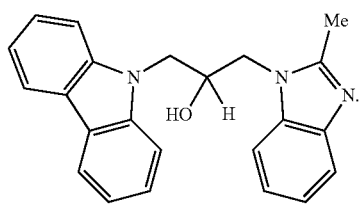

In one embodiment, with respect to the compound of formula B-I, the compound is according to formula B-XIIIa:

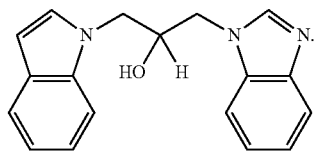

In one particular embodiment, the compound is according to formula B-II, B-III, B-IV, B-V, or B-VI.

In a further aspect, the present invention provides pharmaceutical compositions comprising amide compounds of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein are all pharmaceutically acceptable as prepared and used.

In a further aspect, this invention provides a method of treating a mammal susceptible to or afflicted with a condition from among those listed herein, and particularly, such condition as may be associated with RAGE activity. Such conditions include, without limitation, diabetes and its complications, impaired wound healing, peripheral vascular disease and associated complications, obesity, Alzheimer's disease, cancers, arthritis, nephropathy, acute and chronic inflammation, retinopathy, atherosclerosis, cardiovascular disease, erectile dysfunction, tumor invasion and metastases, neuropathy, cardio- and cerebrovascular ischemia/reperfusion injury, heart attack, stroke, myocardial infarction, ischemic cardiomyopathy, renal ischemia, sepsis, pneumonia, infection, liver injury, liver damage, Amyotrophic lateral sclerosis, neuropathy infection, allergy, asthma, organ damage from pollutants, amyloidoses asthma, pollution-associated tissue damage, skin disorders, colitis, skin aging, and lupus.

Also encompassed herein is a method for inhibiting RAGE activity in a subject (e.g., a mammal) in need thereof, the method comprising administering to the subject an effective RAGE-inhibiting amount of a compound as described herein so as to reduce/inhibit RAGE activity in the subject. Such compounds may be a compound according to formula A-Ia or A-Ib as described herein. In a particular embodiment thereof, with respect to the compound of formula A-Ia, the compound is according to formula A-II, A-III, A-IV, A-V, A-VI, A-VII. In a particular embodiment thereof, with respect to the compound of formula A-Ib, the compound is according to formula A-V. In a particular embodiment, with respect to the compound of formula A-Ia or A-Ib, the compound is according to formula A-XIVa, A-XIVb, A-XIVc, A-XIVd, A-XV, A-XVIb, or A-XXb. In another particular embodiment, with respect to the compound of formula A-Ia or A-Ib, the compound is according to formula A-XIVa, A-XIVb, A-XIVc, A-XIVd, A-XV, A-XVIb, or A-XXb. Such compounds may, furthermore, be a compound according to formula B-I'; a compound according to formula B-I; a compound according to formula B-II; a compound according to formula B-III; a compound according to formula B-IV; a compound according to formula B-V; or a compound according to formula B-VI as described herein. In a particular embodiment, with respect to the compound of formula B-I, the compound is according to formula B-XId. In another particular embodiment, with respect to the compound of formula B-I, the compound is according to formula B-XIIIa. In yet another particular embodiment, the compound is according to formula B-II, B-III, B-IV, B-V, or B-VI.

Other objects and advantages will become apparent to those skilled in the art from a consideration of the ensuing detailed description.

BRIEF DESCRIPTION OF THE DRAWINGS

FIG. 7 presents test compound dissociation constants for CB-1 to CB-14.

FIG. 10 shows the effects of compounds CB-1 to CB-14 on the inflammatory response in the context of delayed type hypersensitivity mediated inflammation in mice.

DETAILED DESCRIPTION OF THE INVENTION

Figure 1:
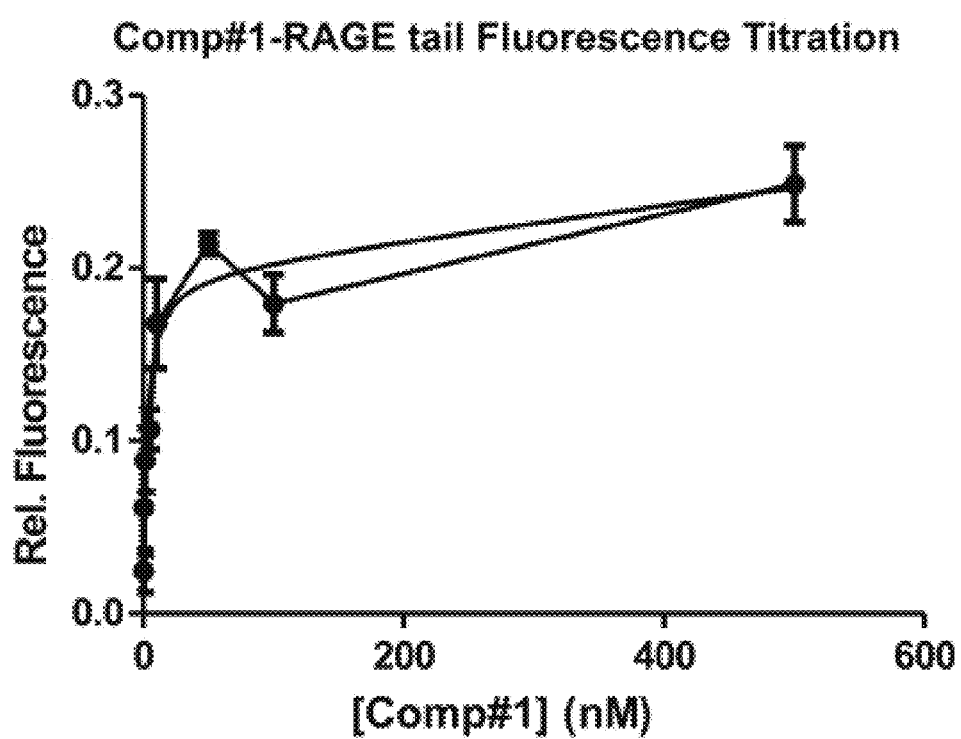
FIG. 1 shows RAGE tail Fluorescence Titration data for Compound CB-1.

In that RAGE and its ligands have been positioned at the center of chronic inflammation and it is, moreover, understood that chronic inflammation contributes significantly to the pathogenesis of diverse disorders, the compounds described herein are envisioned as useful for the treatment of diseases wherein inflammation plays a pathological role and RAGE contributes thereto. Such diseases and disorders include inflammatory bowel disease, delayed-type hypersensitivity, atherosclerosis, the complications of diabetes (including neuropathy and atherosclerosis), asthma, myocardial ischemia, atherosclerosis, aneurysm formation, doxorubicin toxicity, acetaminophen toxicity, neurodegeneration, hyperlipidemia, preeclampsia, rheumatoid arthritis, pulmonary fibrosis, and Alzheimer's Disease. See, for example, Hofmann et al. (1999, Cell 97:889-901); Akirav et al. (2014, PLoS One 9:e95678); Johnson et al. (2014, EJNMMI Res 4:26); Tekabe et al. (2014, Int J Mol Imaging 2014:695391); Song et al. (2014, Diabetes 63:1948-1965); Ullah et al. (2014, J Allergy Clin Immunol 134:440-450); Juranek et al. (2013, Brain Behav 3:701-709); Daffu et al. (2013, Int J Mol Sci 14:19891-19910); Manigrasso et al. (2014, Trends Endocrinol Metab 25:15-22); Tekabe et al. (2013, EJNMMi Res 3:37); Rai et al. (2012, J Exp Med 209:2339-2350); Ramasamy et al. (2012, Vascular Pharmacol 57: 160-167); Arumugam et al. (2012, Clin Canc Res 18:4356-4364); the entire content of each of which is incorporated herein by reference.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)R$^{20}$, where R$^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR$^{21}$C(O)R$^{22}$, where R$^{21}$ is hydrogen, alkyl, cycloalkyl, cycloheteroalkyl, aryl, arylalkyl, heteroalkyl, heteroaryl, heteroarylalkyl and R$^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, iso-propyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —$NO_2$.

"Substituted" refers to a group in which one or more hydrogen atoms are each independently replaced with the same or different substituent(s). Typical substituents include, but are not limited to, —X, —$R^{46}$, —O—, =O, —$OR^{46}$, —$SR^{46}$, —$S^-$, =S, —$NR^{46}R^{47}$, =$NR^{46}$, —$CX_3$, —$CF_3$, —CN, —OCN, —SCN, —NO, —$NO_2$, =$N_2$, —$N_3$, —$S(O)_2O—$, —$S(O)_2OH$, —$S(O)_2R^{46}$, —$OS(O_2)O^-$, —$OS(O)_2R^{46}$, —$P(O)(O^-)_2$, —$P(O)(OR^{46})(O^-)$, —$OP(O)(OR^{46})(OR^{47})$, —$C(O)R^{46}$, —$C(S)R^{46}$, —$C(O)OR^{46}$, —$C(O)NR^{46}R^{47}$, —C(O)O—, —$C(S)OR^{46}$, —$NR^{48}C(O)NR^{46}R^{47}$, —$NR^{48}C(S)NR^{46}R^{47}$, $NR^{49}C(NR^{48})NR^{46}R^{47}$ and —$C(NR^{48})NR^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{50}R^{51}$, —$C(O)R^{50}$ or —$S(O)_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

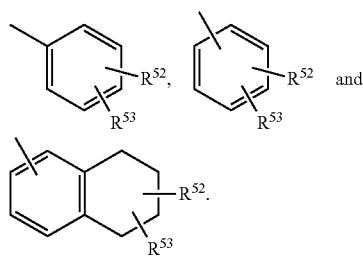

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{54}COR^{55}$, $NR^{54}SOR^{55}$, $NR^{54}SO_2R^{57}$, COOalkyl, COOaryl, $CONR^{54}R^{55}$, $CONR^{54}OR^{55}$, $NR^{54}R^{55}$, $SO_2NR^{54}R^{55}$, S-alkyl, S-alkyl, SOalkyl, $SO_2$alkyl, Saryl, SOaryl, $SO_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

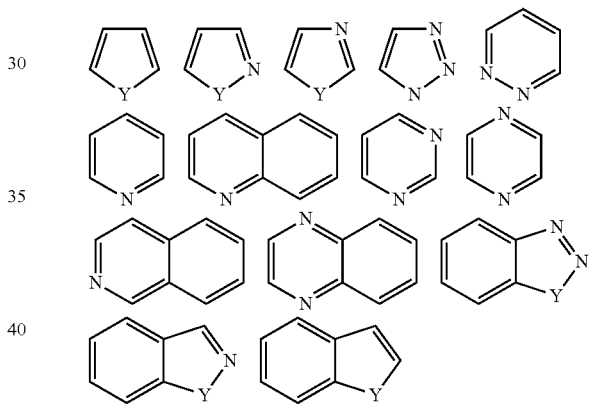

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

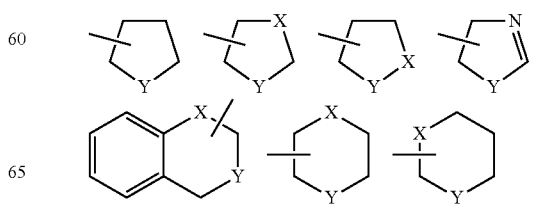

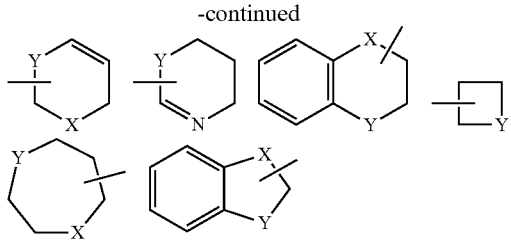

wherein each X is selected from CR$^{58}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

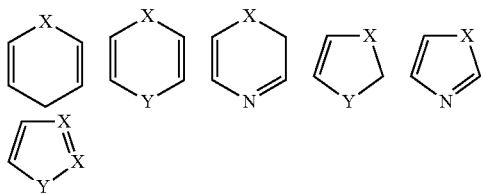

wherein each X is selected from CR$^{58}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

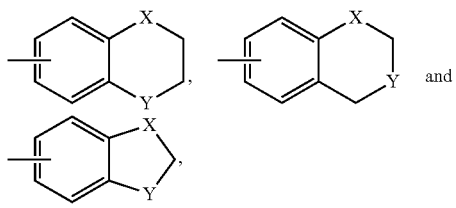

wherein each X is selected from C—R$^{58}_2$, NR$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on A, B, W, Y or Z of the compounds of this invention or may be present as a substituent in the "substituted" aryl and aliphatic groups present in the compounds.

Examples of hetero substituents include:
-halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$) 2, —CONROR$^{59}$,
—SO$_3$H, —R$^{59}$—S, —SO$_2$N(R$^{59}$)$_2$,
—S(O)R$^{59}$, —S(O)$_2$R$^{59}$ wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, or N—H functionality. Examples of "hydrogen bond donor" groups include —OH, —NH$_2$, and —NH—R$^{59a}$ and wherein R$^{59a}$ is alkyl, cycloalkyl, aryl, or heteroaryl.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" or "Pharmaceutically acceptable carrier" refer to a pharmaceutically acceptable diluent, a pharmaceutically acceptable adjuvant, a pharmaceutically acceptable excipient, or a combination of any of the foregoing with which a composition provided by the present disclosure may be administered to a patient and which does not destroy the pharmacological activity thereof and which is non-toxic when administered in doses sufficient to provide a therapeutically effective amount of the composition. In addition to the adjuvants, excipients and diluents known to one skilled in the art, the vehicle or carrier includes nanoparticles of organic and inorganic nature.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", or "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides amino, amido, and heterocyclic compounds capable of modulating the receptor for advanced glycation end products (RAGE) activity.

Specifically, the invention provides amino, amido, and heterocyclic compounds capable of modulating the interaction of RAGE and its ligands, and uses of such compounds to treat diseases or conditions related to RAGE activity.

More specifically, the invention provides amino, amido, and heterocyclic compounds capable of modulating the interaction of RAGE and its ligands binding to the intracellular domain of the RAGE, and uses of such compounds to treat diseases or conditions related to RAGE activity.

In one aspect, the present invention provides a method for preventing, treating or ameliorating in a mammal a disease or condition that is causally related to RAGE activity in vivo, which comprises administering to the mammal an effective disease-treating or condition-treating amount of a compound according to formula A-Ia or A-Ib:

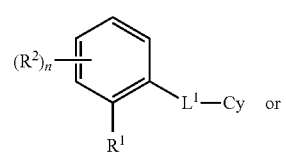

A-Ia

-continued

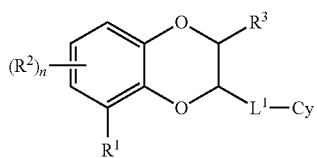
A-Ib wherein
$L^1$ is —NH—, —CH$_2$—NH—, —CH$_2$—CH$_2$—NH—, —CO—NH— or —CO—NH-L$^2$-CO—NH—; and
Cy is substituted or unsubstituted aryl or substituted or unsubstituted heteroaryl; or
$L^1$ is a bond and Cy is

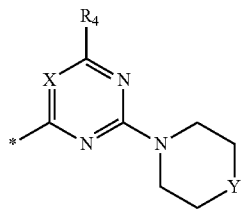

$R^1$ is H, substituted or unsubstituted $C_1$-$C_6$ alkyl, substituted or unsubstituted $C_1$-$C_6$ alkoxy, or halo;
each $R^2$ is independently selected from OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or two adjacent $R^1$ and $R^2$ groups may join together to form a substituted or unsubstituted carbocyclic or heterocyclic ring;
$R^3$ is H, or substituted or unsubstituted $C_1$-$C_6$ alkyl;
the subscript n is 0, 1, 2, or 3;
$L^2$ is $C_1$-$C_3$ alkylene;
X is CH or N; Y is O or NR$^5$;
$R^4$ is substituted or unsubstituted alkyl, substituted or unsubstituted cycloalkyl, substituted or unsubstituted aryl, or substituted or unsubstituted heteroaryl;
$R^5$ is H or substituted or unsubstituted alkyl; and * represents an attachment point;
or a pharmaceutically acceptable salt, solvate or prodrug thereof;
and stereoisomers, isotopic variants and tautomers thereof.

In one embodiment, the conditions associated with RAGE activity include, without limitation, impaired wound healing, peripheral vascular disease, associated complications, obesity, Alzheimer's disease, cancers, arthritis, nephropathy, acute and chronic inflammation, retinopathy, atherosclerosis, erectile dysfunction, tumor invasion and metastasis, neuropathy, cardio- and cerebrovascular ischemia/reperfusion injury, sepsis, pneumonia, infection, liver injury, Amyotrophic lateral sclerosis, neuropathy, allergy, asthma, organ damage from pollutants, amyloidoses, and others.

In one embodiment, with respect to the compound of formula A-Ia or A-Ib, $L^1$ is —NH—. In another embodiment, $L^1$ is —CH$_2$—NH—. In another embodiment, $L^1$ is —CH$_2$—CH$_2$—NH—. In another embodiment, $L^1$ is —CO—NH—. In another embodiment, $L^1$ is —CO—NH-L$^2$-CO—NH—; and $L^2$ is methylene, ethylene, or propylene. In one particular embodiment, $L^1$ is —CH$_2$—.

In another embodiment, with respect to the compound of formula A-Ia or A-Ib, $L^1$ is a bond and Cy is

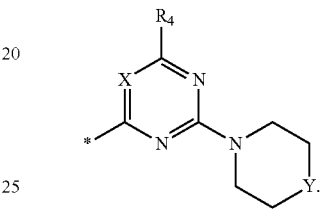

In one embodiment, with respect to the compound of formula A-Ia, the compound is according to formula A-II, A-III, A-IV, A-V, A-VI, A-VII:

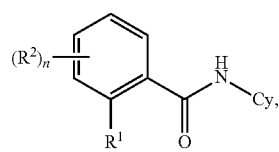
II

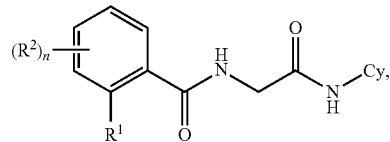
III

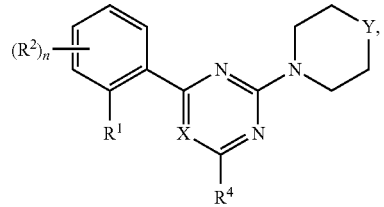
IV

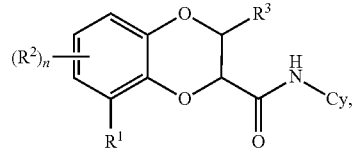
V

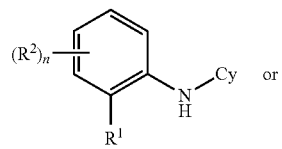
VI

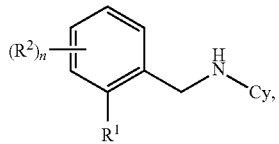

wherein Cy, X, Y, $R^1$, $R^2$, $R^4$, and n are as described for formula A-Ia.

In one embodiment, with respect to the compound of formula A-Ib, the compound is according to formula A-V:

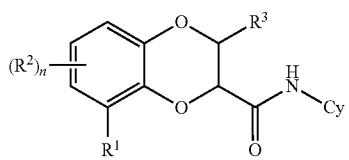

wherein Cy, X, Y, $R^1$, $R^2$, $R^3$, and n are as described for formula A-Ib.

In one embodiment, with respect to the compound of formula A-Ia-A-V, n is 1, 2 or 3. In another embodiment, n is 1 or 2. In yet another embodiment, n is 2. In a further embodiment, n is 0.

In one embodiment, with respect to the compound of formula A-Ia-A-V, each $R^2$ is independently selected from halo, amino, substituted amino, substituted or unsubstituted $C_1$-$C_6$ alkyl, CN, OH, methylthio, and substituted or unsubstituted $C_1$-$C_6$ alkoxy.

In another embodiment, with respect to the compound of formula A-Ia-A-V, each $R^2$ is independently selected from halo, substituted or unsubstituted $C_1$-$C_6$ alkyl, CN, OH, —NHAc, Cl, Br, —SMe, and substituted or unsubstituted $C_1$-$C_6$ alkoxy.

In a particular embodiment, with respect to the compound of formula A-Ia-A-V, n is 1 or 2; and each $R^2$ is independently Cl, Br, F, Me, Et, i-Pr, OMe, $CF_3$, CN, —SMe, —NHAc, or OH. In another particular embodiment, n is 1; and $R^2$ is —SMe. In another particular embodiment, n is 1; and $R^2$ is Br. In another particular embodiment, n is 1; and $R^2$ is —OH. In yet another particular embodiment, n is 2; and one of the $R^2$ is Cl or F; and another $R^2$ is substituted or unsubstituted amino. In a more particular embodiment, n is 2; and one of the $R^2$ is Cl, and another $R^2$ is —NHAc or —NH—C(O)Me.

In one embodiment, with respect to the compound of formula A-Ia, the compound is according to formula A-VIIIa, A-VIIIb, A-VIIIc, or A-VIIId:

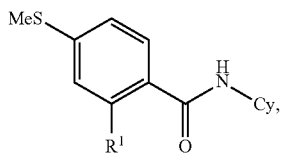

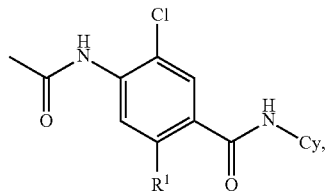

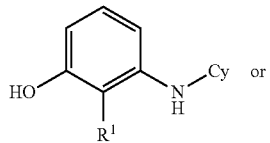

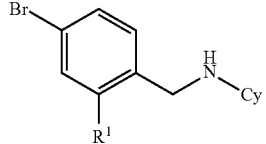

wherein Cy, and $R^1$ are as described for formula A-Ia.

In one embodiment, with respect to the compound of formula A-Ia, the compound is according to A-IX:

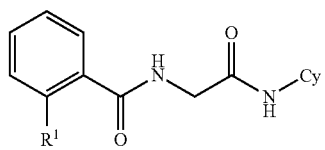

wherein Cy, and $R^1$ are as described for formula A-Ia.

In one embodiment, with respect to the compound of formula A-Ib, the compound is according to formula A-Xa or A-Xb:

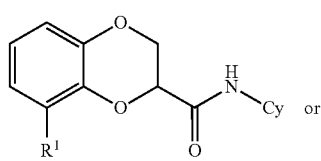

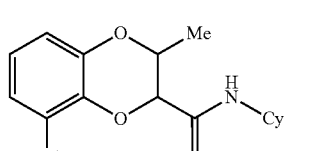

wherein Cy, and $R^1$ are as described for formula A-Ib.

In one embodiment, with respect to the compound of formula A-Ia-A-Xb, $R^1$ is independently selected from H, halo, amino, substituted amino, substituted or unsubstituted $C_1$-$C_6$ alkyl, CN, OH, and substituted or unsubstituted $C_1$-$C_6$ alkoxy. In another embodiment, $R^1$ is independently selected from H, Cl, F, Me, Et, i-Pr, OMe, $CF_3$, CN or OH. In a particular embodiment, $R^1$ is independently selected from H, F, and OMe. In another particular embodiment, $R^1$ is F. In a more particular embodiment, $R^1$ is OMe.

In one embodiment, with respect to the compound of formula A-Ia, the compound is according to formula A-XIa, A-XIb, A-XIc or A-XId:

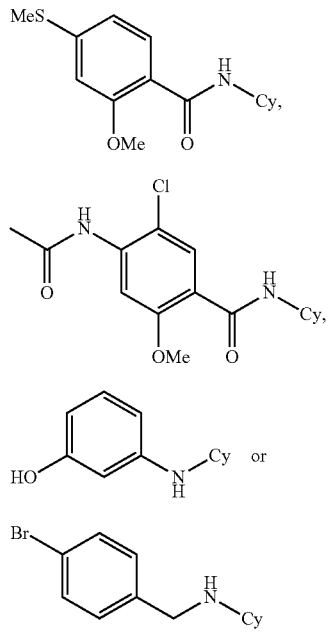

wherein Cy is as described for formula A-Ia.

In one embodiment, with respect to the compound of formula A-Ia, the compound is according to A-XII:

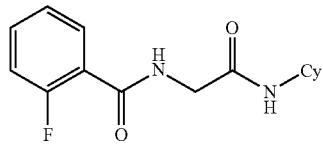

wherein Cy is as described for formula A-Ia.

In one embodiment, with respect to the compound of formula A-Ib, the compound is according to formula A-XIIIa or A-XIIIb:

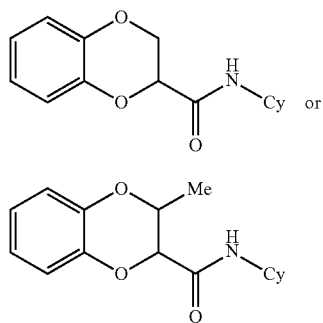

wherein Cy, and R¹ are described for formula A-Ib.

In one embodiment, with respect to the compound of formula A-Ib-A-XIIIb, Cy is substituted or unsubstituted aryl. In another embodiment, Cy is substituted or unsubstituted phenyl. In another embodiment, Cy is phenyl substituted with one or more groups selected from halo, substituted or unsubstituted $C_1$-$C_6$ alkyl, CN, OH, —NHAc, Cl, —SMe, carboxy, carbalkoxy, and substituted or unsubstituted $C_1$-$C_6$ alkoxy. In another embodiment, Cy is phenyl substituted with one or more groups selected from Cl, F, Me, Et, i-Pr, OMe, $CF_3$, CN, —SMe, —NHAc, —COOMe, and OH. In another embodiment, Cy is substituted or unsubstituted heteroaryl. In another embodiment, Cy is substituted or unsubstituted pyridyl. In another embodiment, Cy is pyridyl substituted with one or more groups selected from halo, substituted or unsubstituted $C_1$-$C_6$ alkyl, CN, OH, —NHAc, Cl, —SMe, and substituted or unsubstituted $C_1$-$C_6$ alkoxy. In another embodiment, Cy is pyridyl substituted with one or more groups selected from Cl, F, Me, Et, i-Pr, OMe, $CF_3$, CN, —SMe, —NHAc, and OH. In another embodiment, Cy is substituted or unsubstituted pyrrolyl, imidazolyl, triazolyl, thienyl, furanyl, thiazolyl, or oxazolyl. In a particular embodiment, Cy is substituted or unsubstituted thiazolyl. In a particular embodiment, Cy is unsubstituted thiazolyl.

In one embodiment, with respect to the compound of formula A-Ia, the compound is according to formula A-XIVa, A-XIVb, A-XIVc, or A-XIVd:

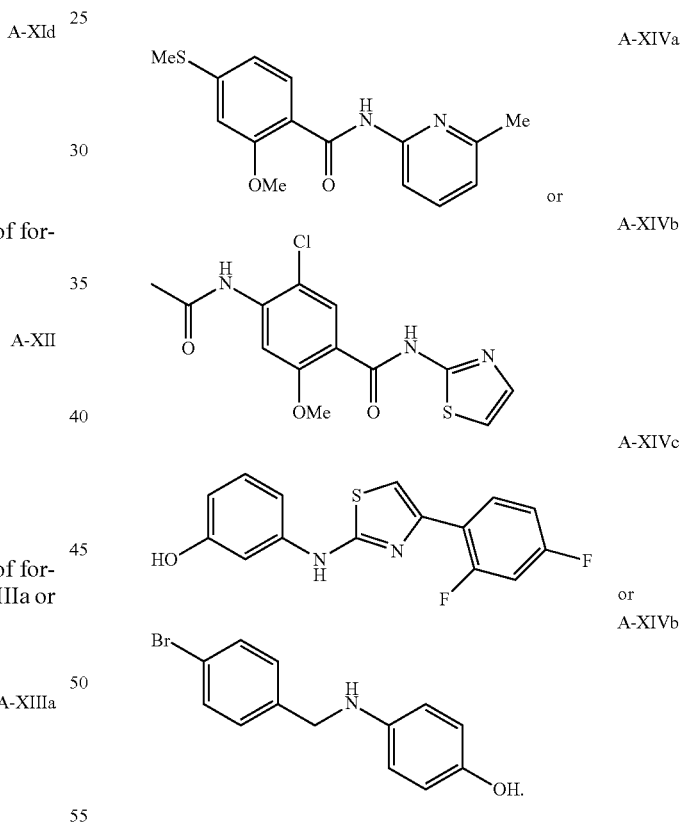

In one embodiment, with respect to the compound of formula A-Ia, the compound is according to A-XV:

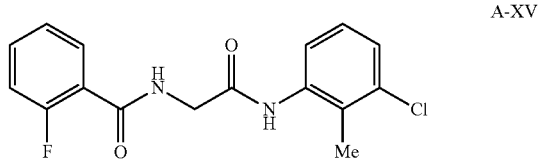 [SMILES: Cc1c(Cl)cccc1NC(=O)CNC(=O)c1ccccc1F]

In one embodiment, with respect to the compound of formula A-Ib, the compound is according to formula A-XVIa or A-XVIb:

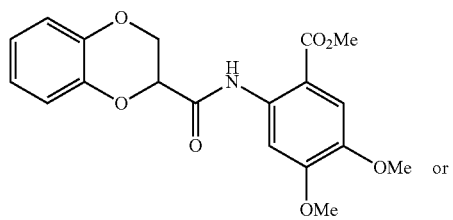

A-XVIa

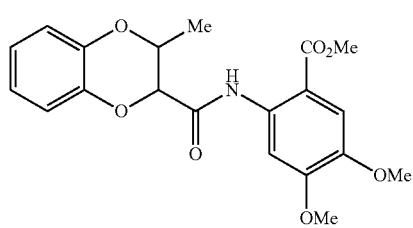

A-XVIb

In one embodiment, with respect to the compound of formula A-Ia, the compound is according to formula A-XVII:

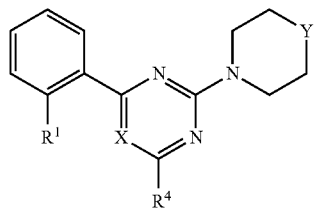

A-XVII wherein X, Y, $R^1$, and $R^4$ are as described for formula A-Ia.

In one embodiment, with respect to the compound of formula A-Ia-A-XVII (when present) X is CH. In another embodiment, X is N.

In one embodiment, with respect to the compound of formula A-Ia, the compound is according to formula A-XVIIIa or A-XVIIIb:

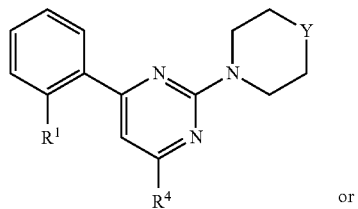

A-XVIIIa or

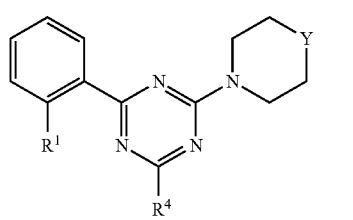

A-XVIIIb wherein $R^1$, and $R^4$ are as described for formula A-Ia.

In one embodiment, with respect to the compound of formula A-Ia-A-XVIIIb (when present) $R^1$ is independently selected from halo, amino, substituted amino, substituted or unsubstituted $C_1$-$C_6$ alkyl, CN, OH, and substituted or unsubstituted $C_1$-$C_6$ alkoxy. In another embodiment, $R^1$ is independently selected from Cl, F, Me, Et, i-Pr, OMe, $CF_3$, CN or OH. In a particular embodiment, $R^1$ is OMe. In one embodiment, Y is NH, or N-Me. In a particular embodiment, Y is O.

In one embodiment, with respect to the compound of formula A-Ia, the compound is according to formula A-XIXa or A-XIXb:

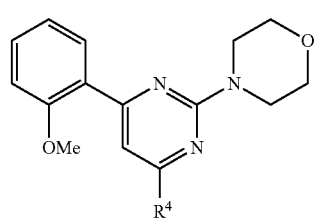

A-XIXa or

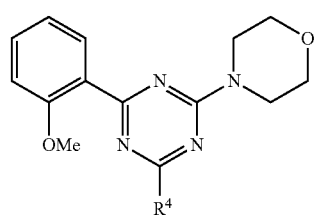

A-XIXb wherein $R^4$ is as described for formula A-Ia.

In one embodiment, with respect to the compound of formula A-Ia-A-XIXb (when present) $R^4$ is substituted or unsubstituted alkyl, substituted or unsubstituted cycloalkyl, substituted or unsubstituted aryl, or substituted or unsubstituted heteroaryl. In another embodiment, $R^4$ is Me, i-Pr, cyclopropyl, $CHF_2$, $CF_3$, Ph, or pyridyl. In a particular embodiment, $R^4$ is $CHF_2$, or $CF_3$. In a more particular embodiment, $R^4$ is $CF_3$.

In one embodiment, with respect to the compound of formula A-Ia, the compound is according to formula A-XXa or A-XXb:

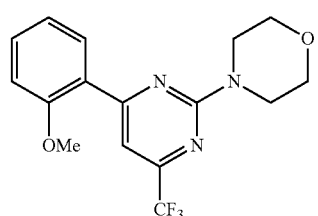

A-XXa or

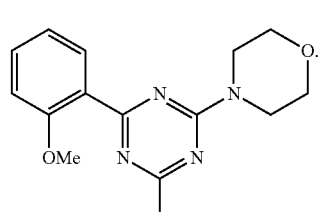

A-XXb

In one embodiment, with respect to the compound of formula A-Ia or A-Ib, the compound is according to formula A-XIVa, A-XIVb, A-XIVc, A-XIVd, A-XV, A-XVIb, or A-XXb.

In another embodiment, with respect to the compound of formula A-Ia, the compound is any one of the compounds listed in Table 2.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-I':

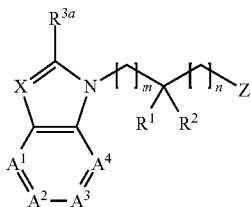

B-I' wherein each $A^1$, $A^2$, $A^3$, and $A^4$ is independently $CR^4$ or N; provided that only 1 or 2 of $A^1$, $A^2$, $A^3$, and $A^4$ are N at any one time;

Z is substituted amino, substituted hydroxyl, substituted or unsubstituted aryl, or substituted or unsubstituted heteroaryl;

X is $CR^{5a}$ or N;

$R^1$ is hydroxy, substituted hydroxyl, amino, or substituted amino;

$R^2$ is H, alkyl or aryl;

$R^{3a}$ is H, substituted or unsubstituted alkyl, substituted or unsubstituted cycloalkyl, substituted or unsubstituted aryl, halo, or cyano;

each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;

$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring; and each of the subscript m and n is independently 1, 2, or 3;

or a pharmaceutically acceptable salt, solvate or prodrug thereof;

or stereoisomers, isotopic variants and tautomers thereof.

In one embodiment, with respect to the compounds of formula B-I', Z is

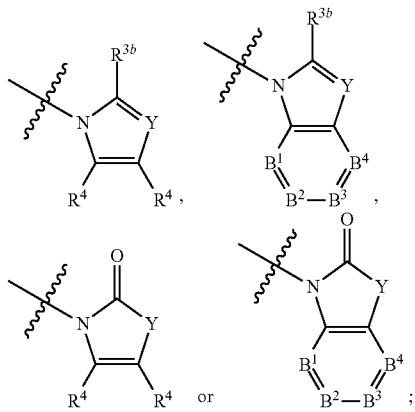

wherein $B^1$, $B^2$, $B^3$, and $B^4$ is independently $CR^4$ or N; Y is $CR^{5b}$ or $NR^{5a}$; $R^{3b}$ is $R^{3a}$; $R^{3a}$ and $R^4$ are as described above; and $R^{5b}$ is independently H, substituted or unsubstituted alkyl, substituted or unsubstituted cycloalkyl, substituted or unsubstituted aryl, halo, or cyano;

or $R^{5b}$ and $R^{3b}$ may join together to form a substituted or unsubstituted carbocyclic or heterocyclic ring In one embodiment, the compound is according to formula B-I'; and each of $A^1$, $A^2$, $A^3$, and $A^4$ is $CR^4$.

In another embodiment, the compound is according to formula B-I'; and one of $A^1$, $A^2$, $A^3$, and $A^4$ is N, and the rest are independently $CR^4$. In one embodiment, each of $R^4$ is H.

In another embodiment, each $R^4$ is independently selected from H, halo, amino, substituted amino, substituted or unsubstituted $C_1$-$C_6$ alkyl, CN, OH, methylthio, and substituted or unsubstituted $C_1$-$C_6$ alkoxy. In another embodiment, each $R^4$ is independently selected from H, halo, substituted or unsubstituted $C_1$-$C_6$ alkyl, CN, OH, —NHAc, Cl, Br, —SMe, and substituted or unsubstituted $C_1$-$C_6$ alkoxy. In another embodiment, each $R^4$ is independently H, Cl, Br, F, Me, Et, i-Pr, OMe, $CF_3$, CN, —SMe, —NHAc, or OH.

In one embodiment, with respect to the compounds of formula B-I', Z is substituted amino. In another embodiment, Z is alkylamino, dialkylamino, phenylamino, diphenylamino, N-alkyl-N-benzylamino, N-alkyl-N-naphthylamino, or N-alkyl-N-phenylamino. In another embodiment, Z is diphenylamino, N-methyl-N-benzylamino, N-ethyl-N-naphthylamino, or N-methyl-N-phenylamino. In another embodiment, Z is substituted hydroxyl. In another embodiment, Z is substituted or unsubstituted phenoxy. In another embodiment, Z is phenoxy or naphthyloxy substituted with alkyl, halo, carboxy, carbalkoxy, or CN. In another embodiment, Z is unsubstituted phenoxy, 4-cyanophenoxy, 2-methylphenoxy, benzyloxy, naphthyloxy, or 2-carboxyphenyloxy. In another embodiment, Z is

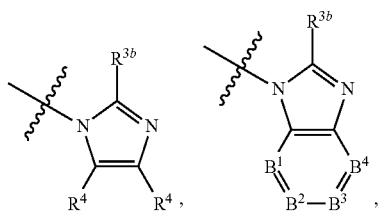

-continued

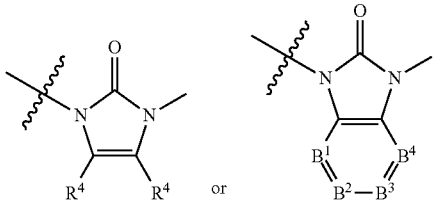

and wherein $B^1$, $B^2$, $B^3$, $B^4$, and $R^{3b}$ are as described herein.

In one embodiment, the compound is according to formula B-I'; Z is as described above; and each of $B^1$, $B^2$, $B^3$, and $B^4$ is $CR^4$. In another embodiment, one of $B^1$, $B^2$, $B^3$, and $B^4$ is N, and the rest are independently $CR^4$. In another embodiment, the compound is according to formula B-I; and two of $B^1$, $B^2$, $B^3$, and $B^4$ is N, and the rest are independently $CR^4$. In one embodiment, each of $R^4$ is H. In another embodiment, each $R^4$ is independently selected from H, halo, amino, substituted amino, substituted or unsubstituted $C_1$-$C_6$ alkyl, CN, OH, methylthio, and substituted or unsubstituted $C_1$-$C_6$ alkoxy. In another embodiment, each $R^4$ is independently selected from H, halo, substituted or unsubstituted $C_1$-$C_6$ alkyl, CN, OH, —NHAc, Cl, Br, —SMe, and substituted or unsubstituted $C_1$-$C_6$ alkoxy. In another embodiment, each $R^4$ is independently H, Cl, Br, F, Me, Et, i-Pr, OMe, $CF_3$, CN, —SMe, —NHAc, or OH.

In another embodiment, the compound is according to formula B-I'; and Z is

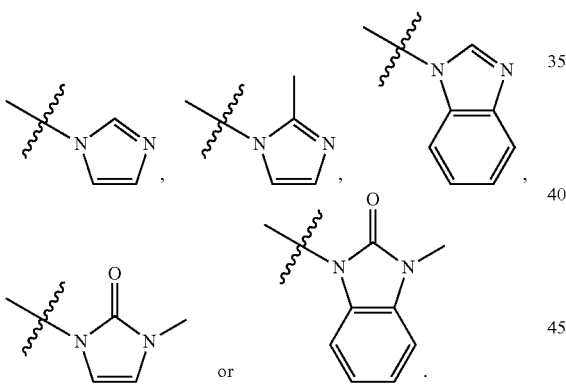

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-I:

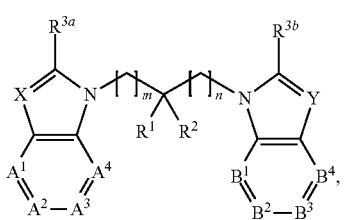

wherein
each $A^1$, $A^2$, $A^3$, $A^4$, $B^1$, $B^2$, $B^3$, and $B^4$, is independently $CR^4$ or N; provided that only 1 or 2 of $A^1$, $A^2$, $A^3$, and $A^4$ are N, and only 1 or 2 of $B^1$, $B^2$, $B^3$, and $B^4$ are N at any one time;
X is $CR^{5a}$ or N; X is $CR^{5b}$ or N;
$R^1$ is hydroxy, substituted hydroxyl, amino, or substituted amino;
$R^2$ is H, alkyl or aryl;
each $R^{3a}$ and $R^{3b}$ is independently H, substituted or unsubstituted alkyl, substituted or unsubstituted cycloalkyl, substituted or unsubstituted aryl, halo, or cyano;
each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;
$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring;
$R^{5b}$ is independently H, substituted or unsubstituted alkyl, substituted or unsubstituted cycloalkyl, substituted or unsubstituted aryl, halo, or cyano; or $R^{5b}$ and $R^{3b}$ may join together to form a substituted or unsubstituted carbocyclic or heterocyclic ring; and each of the subscript m and n is independently 1, 2, or 3;
or a pharmaceutically acceptable salt, solvate or prodrug thereof;
or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-II:

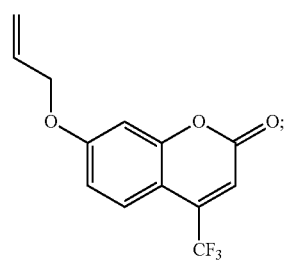

or a pharmaceutically acceptable salt, solvate or prodrug thereof;

or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-III:

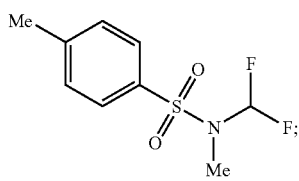

B-III or a pharmaceutically acceptable salt, solvate or prodrug thereof;
or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-IV:

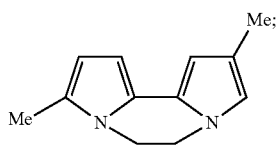

B-IV or a pharmaceutically acceptable salt, solvate or prodrug thereof;
or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-V:

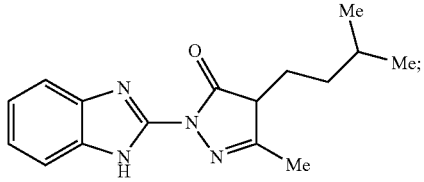

B-V or a pharmaceutically acceptable salt, solvate or prodrug thereof;
or stereoisomers, isotopic variants and tautomers thereof.

In another aspect, the present invention provides a method for preventing, treating or ameliorating in a mammal a disease or condition that is causally related to RAGE activity in vivo, which comprises administering to the mammal an effective disease-treating or condition-treating amount of a compound according to formula B-VI:

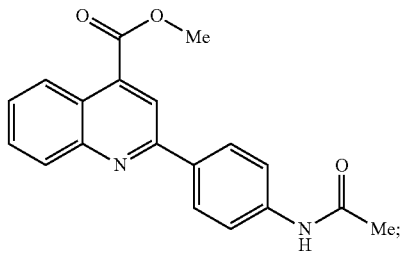

B-VI or a pharmaceutically acceptable salt, solvate or prodrug thereof;
or stereoisomers, isotopic variants and tautomers thereof.

In one embodiment, the compound is according to formula B-I; and each of $A^1$, $A^2$, $A^3$, and $A^4$ is $CR^4$.

In another embodiment, the compound is according to formula B-I; and one of $A^1$, $A^2$, $A^3$, and $A^4$ is N, and the rest are independently $CR^4$.

In another embodiment, the compound is according to formula B-I; and two of $A^1$, $A^2$, $A^3$, and $A^4$ is N, and the rest are independently $CR^4$. In one embodiment, the compound is according to formula B-I; and each of $B^1$, $B^2$, $B^3$, and $B^4$ is $CR^4$. In another embodiment, the compound is according to formula B-I; and one of $B^1$, $B^2$, $B^3$, and $B^4$ is N, and the rest are independently $CR^4$. In another embodiment, the compound is according to formula B-I; and two of $B^1$, $B^2$, $B^3$, and $B^4$ is N, and the rest are independently $CR^4$. In one embodiment, each of $R^4$ is H. In another embodiment, each $R^4$ is independently selected from H, halo, amino, substituted amino, substituted or unsubstituted $C_1$-$C_6$ alkyl, CN, OH, methylthio, and substituted or unsubstituted $C_1$-$C_6$ alkoxy. In another embodiment, each $R^4$ is independently selected from H, halo, substituted or unsubstituted $C_1$-$C_6$ alkyl, CN, OH, —NHAc, Cl, Br, —SMe, and substituted or unsubstituted $C_1$-$C_6$ alkoxy. In another embodiment, each $R^4$ is independently H, Cl, Br, F, Me, Et, i-Pr, OMe, $CF_3$, CN, —SMe, —NHAc, or OH.

In another embodiment, with respect to the compound of formula B-I, the compound is according to formula B-VII:

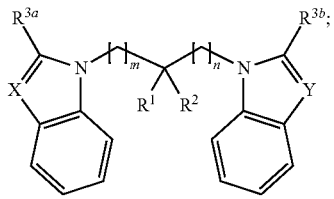

B-VII and wherein X, Y, $R^1$, $R^2$, $R^{3a}$, $R^{3b}$, m, and n are as described for formula B-I;
or a pharmaceutically acceptable salt, solvate or prodrug thereof;
or stereoisomers, isotopic variants and tautomers thereof.

In one embodiment, with respect to the compound of formula B-I', B-I, or B-VII, X is $CR^{5a}$. In another embodiment, X is N. In one embodiment, Y is CR$^{5b}$. In another embodiment, Y is N. In another embodiment, each of X and Y is N.

In another embodiment, with respect to the compound of formula B-I, the compound is according to formula B-VIIIa, B-VIIIb, B-VIIIc, or B-VIIId:

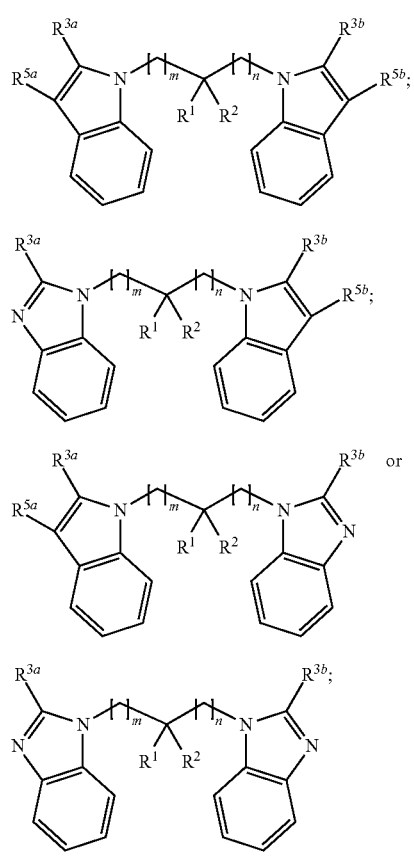

B-VIIIa

B-VIIIb

B-VIIIc or

B-VIIId and wherein R$^1$, R$^2$, R$^{3a}$, R$^{3b}$, R$^{5a}$, R$^{5b}$, m, and n are as described for formula B-I;

or a pharmaceutically acceptable salt, solvate or prodrug thereof;

or stereoisomers, isotopic variants and tautomers thereof.

In one embodiment, with respect to the compound of formula B-I', B-I, B-VII, or B-VIIIa-B-VIIIc, R$^{5a}$ is H, substituted or unsubstituted alkyl, halo, or cyano. In another embodiment, R$^{5a}$ and R$^{3a}$ are joined together to form a substituted or unsubstituted carbocyclic or heterocyclic ring. In another embodiment, R$^{5b}$ is H, substituted or unsubstituted alkyl, halo, or cyano. In another embodiment, R$^{5b}$ and R$^{3b}$ are joined together to form a substituted or unsubstituted carbocyclic or heterocyclic ring.

In another embodiment, with respect to the compound of formula B-I', B-I, B-VII, or B-VIIIa-B-VIIIc, R$^{3a}$ is independently H, substituted or unsubstituted alkyl, substituted or unsubstituted cycloalkyl, substituted or unsubstituted aryl, halo, or cyano. In another embodiment, R$^{3a}$ is H. In another embodiment, R$^{3a}$ is substituted or unsubstituted alkyl. In another embodiment, R$^{3a}$ is Me, Et, i-Pr, CF$_3$, or CHF$_2$.

In another embodiment, with respect to the compound of formula B-I, the compound is according to formula B-IXa, B-IXb, or B-IXc:

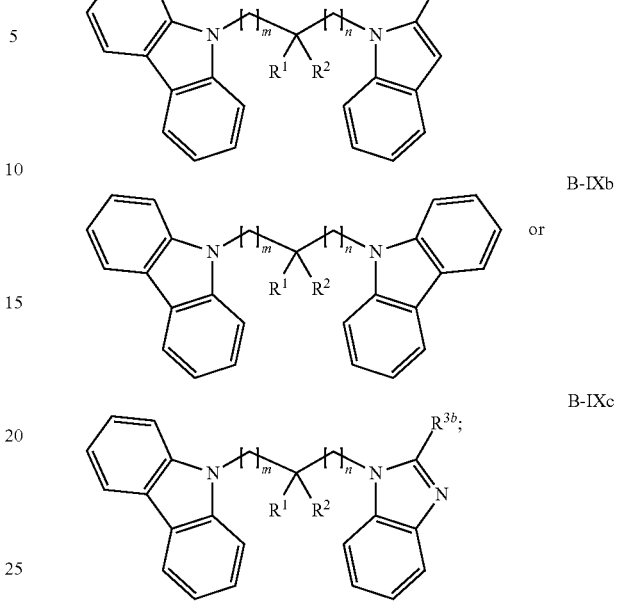

B-IXa

B-IXb or

B-IXc and wherein R$^1$, R$^2$, R$^{3b}$, m, and n are as described for formula B-I;

or a pharmaceutically acceptable salt, solvate or prodrug thereof;

or stereoisomers, isotopic variants and tautomers thereof.

In one embodiment, with respect to the compound of formula B-I', B-I, B-VII, or B-VIIIa-B-IXc, R$^1$ is hydroxy or substituted hydroxy, In another embodiment, R$^1$ is OH, alkoxy, or acyloxy. In another embodiment, R$^1$ is OH. In another embodiment, R$^2$ is substituted or unsubstituted alkyl. In another embodiment, R$^2$ is Me, Et, n-Pr, or i-Pr. In another embodiment, R$^2$ is substituted or unsubstituted aryl. In another embodiment, R$^2$ is Ph. In another embodiment, R$^2$ is H. In one embodiment, m is 1. In another embodiment, n is 1.

In another embodiment, with respect to the compound of formula B-I, the compound is according to formula B-Xa, B-Xb, B-Xc, or B-Xd:

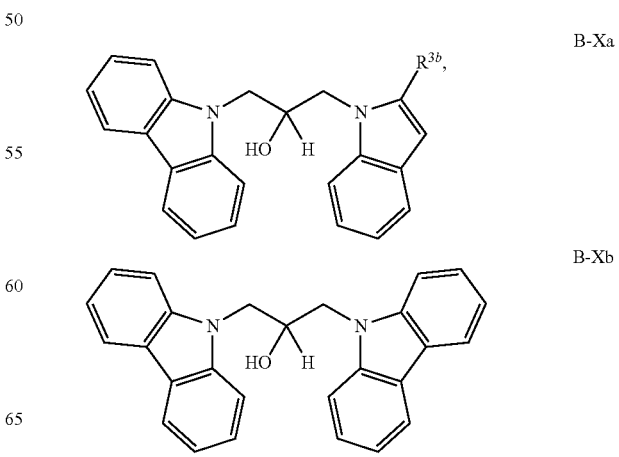

B-Xa

B-Xb

B-Xc

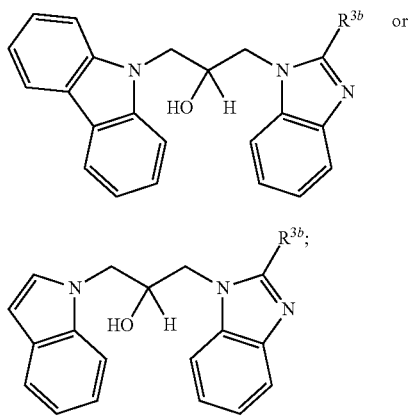

B-Xd and wherein $R^{3b}$ is as described for formula B-I;

or a pharmaceutically acceptable salt, solvate or prodrug thereof;

or stereoisomers, isotopic variants and tautomers thereof.

In another embodiment, with respect to the compound of formula B-I', B-I, B-VII, or B-VIIIa-B-Xd, $R^{3b}$ is independently H, substituted or unsubstituted alkyl, substituted or unsubstituted cycloalkyl, substituted or unsubstituted aryl, halo, or cyano. In another embodiment, $R^{3b}$ is H. In another embodiment, $R^{3b}$ is substituted or unsubstituted alkyl. In another embodiment, $R^{3b}$ is Me, Et, i-Pr, $CF_3$, or $CHF_2$.

In another embodiment, with respect to the compound of formula B-I, the compound is according to formula B-XIa, B-XIb, B-XIc, B-XId, B-XIe, B-XIf, B-XIg, or B-XIh:

B-XIa

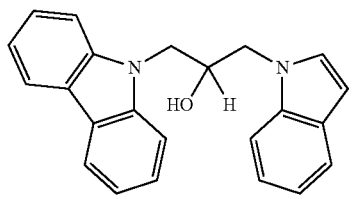

B-XIb

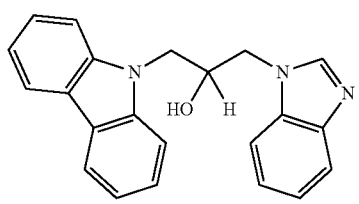

B-XIc

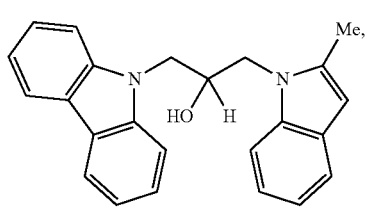

B-XId

B-XIe

B-XIf

B-XIg

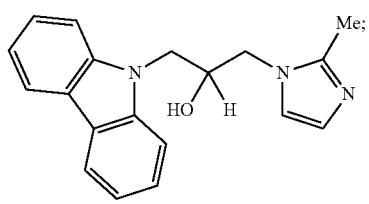

B-XIh or a pharmaceutically acceptable salt, solvate or prodrug thereof;

or stereoisomers, isotopic variants and tautomers thereof.

In another embodiment, with respect to the compound of formula B-I, the compound is according to formula B-XIIa, B-XIIb, XIIc, B-XIId, B-XIIe, or B-XIIf:

B-XIIa

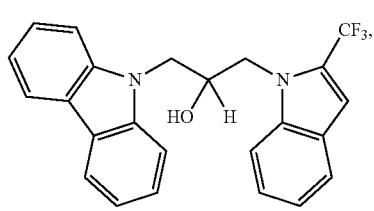

-continued

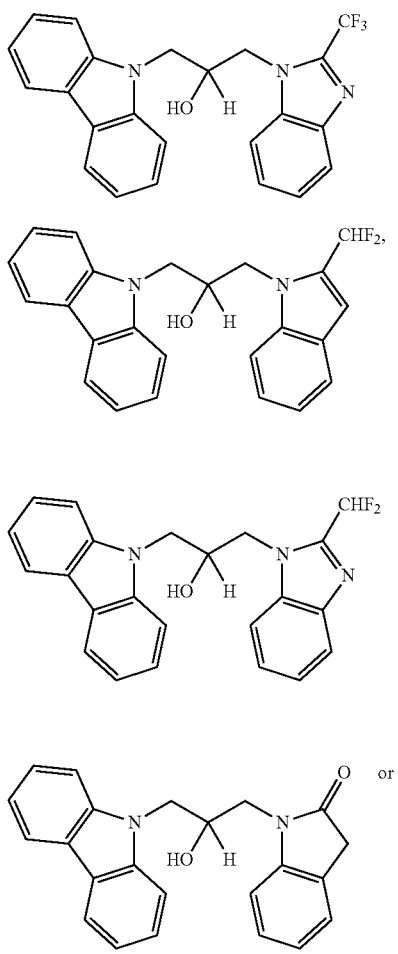

B-XIIb

B-XIIc

B-XIId

B-XIIe

B-XIIf or a pharmaceutically acceptable salt, solvate or prodrug thereof;

or stereoisomers, isotopic variants and tautomers thereof.

In another embodiment, with respect to the compound of formula B-I, the compound is according to formula B-XIIIa, B-XIIIb, B-XIIIc, or B-XIIId:

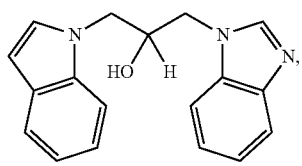

B-XIIIa

-continued

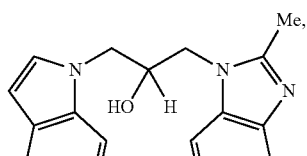

B-XIIIb

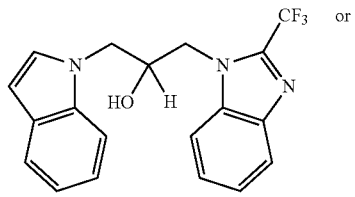

B-XIIIc or

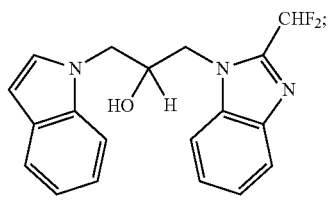

B-XIIId and wherein $R^{3b}$ is as described for formula B-I;

or a pharmaceutically acceptable salt, solvate or prodrug thereof;

or stereoisomers, isotopic variants and tautomers thereof.

In another embodiment, with respect to the compound of formula B-I, the compound is according to formula B-XIVa, or B-XIVb:

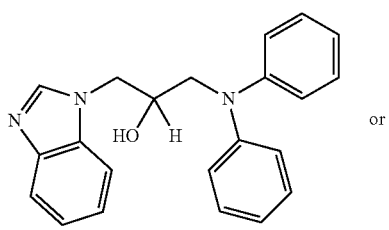

B-XIVa or

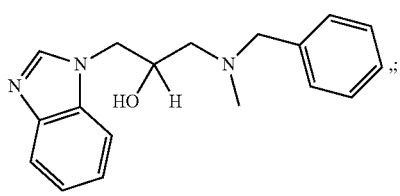

B-XIVb or a pharmaceutically acceptable salt, solvate or prodrug or stereoisomers, isotopic variants and tautomers thereof In another embodiment, with respect to the compound of formula B-I, the compound is according to formula B-XVa, B-XVb, B-XVc, or B-XVd:

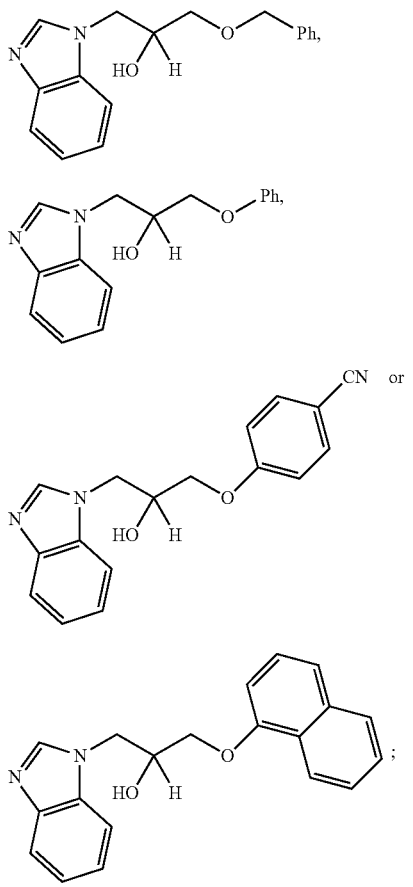

or a pharmaceutically acceptable salt, solvate or prodrug or stereoisomers, isotopic variants and tautomers thereof In another embodiment, with respect to the method, the compound is according to formula B-I'.

In another embodiment, with respect to the method, the compound is according to formula B-I.

In another embodiment, with respect to the method, the compound is according to formula B-II.

In another embodiment, with respect to the method, the compound is according to formula B-III.

In another embodiment, with respect to the method, the compound is according to formula B-IV.

In another embodiment, with respect to the method, the compound is according to formula B-V.

In another embodiment, with respect to the method, the compound is according to formula B-XId.

In another embodiment, with respect to the method, the compound is according to formula B-XIIIa.

In another embodiment, with respect to the method, the compound is any one of the compounds listed in Table 3.

In another embodiment, with respect to the method, the compound is any one of the compounds listed in Table 4.

In a further aspect, this invention provides a method of treating a mammal susceptible to or afflicted with a condition from among those listed herein, and particularly, such conditions as may be associated with RAGE. Such conditions include, without limitation, the disease or condition is selected diabetes and its complications, impaired wound healing, peripheral vascular disease and associated complications, obesity, cancers, arthritis, nephropathy, acute and chronic inflammation, retinopathy, atherosclerosis, cardiovascular disease erectile dysfunction, tumor invasion and metastases, cardio- and cerebrovascular ischemia/reperfusion injury, heart attack, stroke, myocardial infarction, ischemic cardiomyopathy, renal ischemia, sepsis, pneumonia, infection, liver injury, liver damage, neuropathy infection, allergy, asthma, organ damage from pollutants, amyloidoses asthma, pollution-associated tissue damage, skin disorders, colitis, skin aging, lupus, and others.

In a further aspect, the conditions include, Alzheimer's disease, neuropathy, Amyotrophic lateral sclerosis, neuropathy and others.

In one embodiment, with respect to the method of treatment, the disease or condition is a diabetes associated complication.

In one embodiment, with respect to the method of treatment, the disease or condition is atherosclerosis.

In one embodiment, with respect to the method of treatment, the disease or condition is arthritis.

In one embodiment, with respect to the method of treatment, the disease or condition is neurodegeneration.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, intraocular, transdermal, subcutaneous, intravenous, intramuscular, intraperitoneal, interdermal, directly into cerebrospinal fluid, intratracheal, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, a compound as described herein is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered locally to the eye for the treatment of diabetic neuropathy. Suitable compositions include those administrable by eye drops, injections or the like. In the case of eye drops, the composition can also optionally include, for example, ophthalmologically compatible agents such as isotonizing agents, buffering agents, surfactants, stabilization agents, and other ingredients. For injection, the compound can be provided in an injection grade saline solution, in the form of an injectable liposome solution, slow-release polymer system or the like.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

Types 1 and 2 diabetes are on the rise in the United States and world-wide [1-3]. The long-term consequences of diabetes ensue from the direct and indirect effects of hyperglycemia. Diabetes attacks the macro- and microvasculature and is well-established as a leading cause of heart attacks and stroke, blindness, renal failure, amputations, and peripheral neuropathies. The strong epidemiological links between diabetes and Alzheimer's disease raise the possibility that devastating loss of quality and duration of life in the form of irreversible chronic disease often accompany diabetes. Despite significant advances in the treatment of hyperglycemia, definitive means to prevent the complications of diabetes are not yet on the immediate horizon. Indeed, rigorous control of hyperglycemia, particularly in older individuals, may be fraught with significant sequelae, such as striking hypoglycemia, seizures, cardiac ischemia and death [4-6].

The products of nonenzymatic glycation and oxidation of proteins and lipids, the advanced glycation endproducts (AGEs), form and accumulate to accelerated degrees in hyperglycemia [7]. AGEs may be detected in the plasma, urine, skin and other tissues of diabetic subjects and their presence has been linked to the development of complications of diabetes. AGEs impart their effects in part by non-receptor mediated mechanisms, such as by cross-linking of the body's proteins, particularly those that are long-lived such as in basement membranes. AGEs also exert their effects by receptor-dependent mechanisms; the chief receptor for AGE is the receptor for AGE or RAGE. Extensive evidence reveals that expression of RAGE, a member of the immunoglobulin superfamily of cell surface molecules, is increased in animal model and human diabetic tissues, such as in the macro- and microvascular tissues. RAGE is a multi-ligand receptor and the finding that RAGE binds at least certain members of the pro-inflammatory S100/calgranulin family and high mobility group box 1 (HMGB1) indicate that inflammatory mechanisms contribute integrally to the pathogenesis of complications. Indeed, non-AGE RAGE ligands also accumulate in human and animal model diabetic tissues [8-9]. Once thought highly unlikely, the role of inflammation in at least certain forms/stages of diabetic complications is now widely appreciated. Pharmacological and genetic approaches by multiple laboratories, working independently, have provided very strong support for roles for RAGE in the pathogenesis of diabetic complications. For example, administration of antibodies to RAGE or soluble RAGE (the latter the extracellular ligand binding domain of RAGE) or genetic deletion of RAGE significantly reduces accelerated diabetic atherosclerosis in mice; ischemia/reperfusion injury in the diabetic hearts; pathological and functional indices of nephropathy; pathological and functional indices of neuropathy; and improves wound healing in diabetic animals [8-9].

Accumulating evidence reveals that levels of soluble RAGEs (cell surface cleaved RAGE and the endogenous secretory (splice variant)) may be biomarkers of diabetes and its complications in human subjects; levels of soluble RAGEs appear to be modulated by therapeutic interventions, thereby raising the significance of measuring these forms of circulating RAGE.

In this direct context, the inventors and others demonstrated that the cytoplasmic domain of RAGE is essential for the impact of RAGE ligand-RAGE interaction in modulation of gene expression and generation of vascular and inflammatory cell dysfunction. The cytoplasmic domain of RAGE does not appear to exert its downstream signaling impact simply by endogenous phosphorylation; hence, the inventors sought to test the premise that intracellular binding effectors were essential to bind to the RAGE tail and thus facilitate engagement of intracellular signaling pathways. Toward that end, the inventors performed a yeast-two-hybrid assay using the RAGE tail as "bait." From this experimental work, the inventors discovered and published in 2008 that the cytoplasmic domain of RAGE interacts with the formin molecule, mDia1 (diaphanous 1) and that mDia1 is required for the impact of RAGE signaling in multiple cell types such as smooth muscle cells, macrophages, cardiomyocytes and endothelial cells [10-13].

Fundamental observations link mDia1 to the pathological indices of RAGE signal transduction directly relevant to diabetic complications. Thus, modulating the interaction between RAGE and mDia1 is desirable for treating diseases and conditions where RAGE is implicated.

Further to the above, it will be appreciated that the compounds described herein act as modulators of RAGE binding to its intracellular ligands (e.g., mDia1) and thereby reduce or prevent the activation of NF-κB regulated genes, such as the cytokines IL-1, and TNF-α, and minimize the generation of oxidative stress. The ability of the compounds described herein to antagonize or inhibit the binding of physiological ligands to the intracellular tail of RAGE renders them well suited to use as therapeutic agents for treating or managing diseases or conditions related to RAGE activity. More particularly, the amino, amido, and heterocyclic compounds described herein may be used to treat, for example, diabetes complications, inflammation, neurodegeneration, obesity, cancer, ischemia/reperfusion injury, cardiovascular disease, Alzheimer's Disease, and other diseases understood to be related to RAGE activity. Such compounds may be used to impair downstream signaling events resulting from, for example, AGE-RAGE interaction, which contributes to diabetic complications, S100/EN-RAGE/calgranulin-RAGE interaction, which contributes to inflammatory diseases, β-amyloid-RAGE interaction, which contributes to Alzheimer's Disease, and high mobility group box 1 (HMGB1)-RAGE interaction, which contributes to, e.g., inflammation and cancer.

Diabetes and Diabetes Complications

Further to the above, the amino, amido, and heterocyclic compounds described herein are useful for managing and/or treating complications associated with diabetes. Nonenzymatic glycoxidation of macromolecules results in the formation of advanced glycation endproducts (AGEs). The term AGEs refers to a heterogeneous group of compounds generated through the non-enzymatic glycation or glycoxidation of proteins, lipids, and nucleic acids. More particularly, AGEs are the result of a series of complex biochemical reactions that involve the formation of Amadori products, glyceraldehyde-3-phosphate, and the reactive carbonyl methylglyoxal (MG). See, for example, Manigrasso et al. (2014, Trends in Endocrin Metab 25:15-22); the entire content of which, including references cited therein, is incorporated herein by reference. Nonenzymatic glycoxidation of macromolecules is known to be enhanced in the presence of hyperglycemia and other conditions associated with systemic or local oxidant stress. It is also known to be enhanced in renal failure and at sites of inflammation, and amongst other locales associated with neurodegeneration, obesity, and cancer. Schmidt et al. (1995, Nature Med. 1:1002-1004), for example, have shown that AGEs accumulate generally in the vasculature and tissues of patients with diabetes. Other research has demonstrated that AGEs also accumulate in the vasculature focally, as observed in the joint amyloid composed of AGE-β2-microglobulin found in patients with dialysis-related amyloidosis (Abedini et al. 2013, FEBS Lett 587:1119-1127; Miyata et al. 1993, J. Clin. Invest. 92:1243-1252; Miyata et al. 1996, J. Clin. Invest. 98:1088-1094). AGE production is also directly accelerated by hyperglycemia. AGE formation is also frequently associated with an increase in reactive oxygen species (ROS) (Fu et al. 1994, Diabetes 43:676-683). Although AGEs accumulate slowly in both plasma and tissues during aging (Brownlee et al. 1988, N Engl J Med 318:1315-1321; Hallam et al. 2010, Aging Cell 9:776-784; Schleicher et al. 1997, J Clin Inv 99:457-468), they are markedly increased in patients with diabetes (Makita et al. 1991, N Engl J Med 325:836-842).

Suitable animal models in which to study diabetes complications are known in the art and are described in, for example, Manigrasso et al. (2014, Trends in Endocrin Metab 25:15-22); Stirban et al. (2014, Molecular Metabolism 3:94-108); Johnson et al. (2014, EJNMMI Res 4:26); Tekabe et al. (2014, Int J Mol Imaging Article Id 695391); Kaida et al. (2013, Diabetes 62:3241-3250); Tekabe et al. (2013, EJNMMi Res 3:37); Calcutt et al. (2009, Nat Rev Drug Discov 8:417-429); Dauch et al. (2013, J Neuroinflammation 10:64); Juranek et al. (2013, Diabetes 62:931-943); Singh et al. (2014, Korean J Physiol Pharmacol 18:1-14); Ramasamy et al. (2012, Vascular Pharmacol 57: 160-167); Montagnani (2008, Br J Pharmacol 154:725-726); Nakamura et al. (1993, Am J Pathol 143:1649-1656); Lin et al. (2003, Atherosclerosis 168:213-220); Hofmann et al. (2002, Diabetes 51:2082-2089); Lin et al. (2002, Atherosclerosis 163:303-311); Vlassara et al. (1992, Proc Natl Acad Sci 89:12043-12047); Brownlee et al. (1986, Science 232:1629-1632); Li et al. (1996, Proc Natl Acad Sci 93:3902-3907); Park et al. (1998, Nature Med 4:1025-1031); Kislinger et al. (2001, Arteriosclerosis, Thrombosis, and Vascular Biology 21:905-910); Bucciarelli et al. (2002, Circulation 106:2827-2835); Wendt et al. (2006, Atherosclerosis 185:70-77); the entire content of each of which is incorporated herein by reference.

Diabetic Complications—Heart

More particularly, animal models of human diabetes involving diabetic complications of the heart include ex vivo isolated perfused heart ischemia/reperfusion, left anterior descending coronary artery ligation, and cardiac autonomic neuropathy. References describing such models are known in the art and described in, for example, Stables et al. (2014, Autonom Neurosci 177: 746-80), Bucciarelli et al. (2000, Circulation (Supplement) 102: #563, II-117), and Aleshin et al. (2008, Am J Physiol Heart Circ Physiol 294: H1823-H1832); the entire content of each of which is incorporated herein by reference.

Diabetic Complications—Kidney

More particularly, animal models of human diabetes involving diabetic complications of the kidney include OVE26 mice, streptozotocin induced animals, Db/db mice, and nephrectomy. References describing such models are known in the art and described in, for example, Kaur et al. (2014, Inflammopharmacology 22:279-293), Reiniger et al. (2010, Diabetes 59: 2043-2054), and Wendt et al. (2003, American Journal of Pathology 162:1123-1137); the entire content of each of which is incorporated herein by reference.

Diabetic Complications—Retinopathy

More particularly, animal models of human diabetes involving diabetic complications leading to retinopathy include streptozotocin induced animals, Db/db mice, and Akita mice. References describing such models are known in the art and described in, for example, Lai et al. (2013, J Diabetes Res 013:106594) and Barile et al. (2005, Invest Ophthalmol Vis Sci 46:2916-2924); the entire content of each of which is incorporated herein by reference.

Diabetic Complications—Neuropathy

More particularly, animal models of human diabetes involving diabetic complications leading to neuropathy include Swiss Webster mice, Db/db mice, and Sciatic nerve transection/crush. References describing such models are known in the art and described in, for example, Juranek et al. (2010, Biochem Insights 2010:47-59), Juranek et al. (2013, Diabetes 62: 931-943), Islam (2013, J Diabetes Res 2013: 149452); the entire content of each of which is incorporated herein by reference.

Animal models of diabetes in general include streptozotocin induced animals, Akita mice, Db/db mice, and Ob/ob mice. These animal models are known in the art and described in, for example, Park et al. (1998, Nature Medicine 4:1025-1031), Wendt et al. (2006, Atherosclerosis 185:70-77), Wang et al. (2014, Curr Diabetes Rev 10: 131-145), and Acharjee et al. (2013, Can J Diabetes 37: 269-276); the entire content of each of which is incorporated herein by reference.

Immune/Inflammatory Responses

As described herein and demonstrated in, for example, FIG. 10, Example 4, and Table 5, the compounds described herein are useful in treating inflammation. In that inflammation is a common feature underlying all of the diseases and conditions described herein, the utility of the compounds described herein in reducing inflammation in the animal model of inflammation underscores the reasonable expectation that these compounds will also be efficacious in the context of, for example, diabetes complications, obesity, cancer, ischemia/reperfusion injury, cardiovascular disease, neurodegeneration, Alzheimer's Disease, cystic fibrosis, multiple sclerosis, rheumatoid arthritis, psoriasis, atopic dermatitis, and eczema.

As alluded to above, RAGE is a receptor for many members of the S100/calgranulins, a family of closely related calcium-binding polypeptides that accumulate at sites of chronic immune/inflammatory responses, such as those observed in cystic fibrosis and rheumatoid arthritis. RAGE, moreover, is known to mediate the proinflammatory effects of S100/calgranulins on a variety of cells, including lymphocytes and mononuclear phagocytes. Indeed, RAGE-ligand interactions with, e.g., proinflammatory S100/calgranulins, high mobility group box 1 (HMGB1), and/or AGEs are implicated as having a pivotal role in the inflammatory cascade in general. See, for example, Ramasamy et al. (2012, Vascular Pharmacol 57: 160-167); Andersson et al. (2011, Annu Rev Immunol 29:139-162); the entire content of each of which, including references cited therein, is incorporated herein by reference. Studies using in vitro models and in animal models of the delayed-type hypersensitivity (DTH) response, colitis in IL-10 null mice, collagen-induced arthritis, and experimental autoimmune encephalitis models further underscore the fundamental role of RAGE-ligand interactions in various inflammatory diseases including rheumatoid arthritis and multiple sclerosis.

RAGE is also been implicated in inflammatory diseases of the skin such as but not limited to psoriasis, atopic dermatitis, and eczema. Psoriasis may, moreover, be accompanied by arthropathic symptoms that are similar to those seen in rheumatoid arthritis. High levels of pro-inflammatory cytokines, particularly IL-1 and IL-8, are detected in psoriatic lesions. IL-8 is a chemotactic factor for neutrophils, which are known to synthesize and secrete S100 proteins. As indicated herein above, S100 proteins are RAGE ligands, which interaction leads to the propagation of immune and inflammatory responses that contribute and lead to a variety of diseases/conditions described herein. Psoriasin (S100A7), a member of the S100 gene family, is a secreted protein isolated from psoriatic skin. Linkage of psoriasis genetic susceptibility to distinct overexpression of S100 proteins in the skin has, furthermore, been demonstrated (Semprini et. al. 2002, Hum. Genet. 111:310-3). The compounds described herein are therefore envisioned as therapeutic agents for psoriasis in light of their ability to inhibit RAGE mediated downstream signaling.

High Mobility Group Box 1 (HMGB1)

HMGB1, which is also known as amphoterin, has dual activities. It was originally characterized as a structural protein localized to the nucleus where it functions to stabilize DNA structure and modulate transcriptional activity (Stros et al. 2010, Biochem Biophys Acta 1799:101-113). HMGB1 was also later discovered to be an actively secreted cytokine, produced by macrophages and other inflammatory cells during the innate immune response to invasion (Wang et al. 1999, Science 285:248-251). Like other members of the proinflammatory cytokine family, biologically active HMGB1 can be expressed on the plasma membrane or released by activated inflammatory cells to accumulate in vivo during infection and injury. HMGB1 acts as an effector molecule capable of altering the metabolic and immunological activities of hematopoietic, epithelial, and neuronal cells. The breadth of its effector functions is reflected in its known activities, which include significant roles in fever, anorexia, acute-phase responses, and vascular leakage syndrome. HMGB1 acts in synergy with other cytokines and pathogen-derived molecules in these diseases/conditions. The contribution of HMGB1 to these and other pathological conditions is underscored by the numerous demonstrations that administration of agents that specifically inhibit HMGB1 activity (antibodies, antagonist proteins, release inhibitors) to animals with ischemia and inflammatory diseases interrupts the progression of tissue injury and suppresses inflammatory responses in treated animals. See, Andersson et al. (2011, Annu Rev Immunol 29:139-162) for a review.

The available evidence thus demonstrates that HMGB1 is a general mediator of inflammation, implicated in a plethora of inflammatory and autoimmune diseases. In that HMGB1 is a ligand for RAGE, these findings underscore the role of RAGE as a general mediator of inflammation and render apparent that targeting RAGE activity with the intent to inhibit downstream signaling therefrom has significant promise and use of the compounds described herein for the treatment of subjects afflicted with diseases/conditions characterized by inflammation and/or autoimmunity would attenuate clinical signs and symptoms of inflammation in such subjects.

Animal models of autoimmunity/inflammation include those involving delayed type hypersensitivity, Rheumatoid arthritis, Systemic lupus erythematosis, Ulcerative colitis, Crohn's disease, Psoriasis, Behcet's syndrome, Type 1 diabetes, Vasculitis, Glomerulonephritis, Sarcoidosis. Such animal models are known in the art and described in, for example, Hofmann et al. (1999, Cell 97:889-901), Hofmann et al. (2002, Genes and Immunity 3:123-135), Webb et al. (2014, Biochem Pharmacol 87:121-130), Sakata et al. (2012, Exp Diabetes Res 2012:256707), Goyal et al. (2014, Inflammopharmacology 22:219-233), Lu et al. (2014, Life Sci 108 (1):1-6), Starr et al. (2014, Aging Dis 5: 126-136); the entire content of each of which is incorporated herein by reference.

Obesity

Animal models of human obesity are known in the art and involve feeding mice a 45% high fat diet or a 60% high fat diet. Such models are described in, for example, Song et al. (2014, Diabetes 63(6): 1948-1965) and Aydin et al. (2014, Nutrition 30: 1-9); the entire content of each of which is incorporated herein by reference.

Cancer

Abnormal expression of RAGE and its ligands has been reported in a number of cancers, including prostatic, colorectal, pancreatic, lung, and oral squamous cell cancers. It is, moreover, thought that the interaction of RAGE with its ligands contributes to cancer invasion and metastasis. The interaction between RAGE and HMGB1 triggers the activation of key cell signaling pathways, such as NF-κB, p38, p44/42 MAPKs, and activation of these pathways contributes to cancer progression and metastasis (Sims et al. 2010, Annu Rev Immunol 28:367-388; Sparvero et al. 2009, J Transl Med 7:17; Lodgson et al. 2007, Curr Mol Med 7:777-789; Kuniyasu et al. 2003, Oncol Rep 10:445-448; Kuniyasu et al. 2003, Int J Cancer 104:722-727; Sasahira et al. 2005, Virchows Arch 446:411-415; Kuniyasu et al. 2005, Am J Pathol 166: 751-760; Kuniyasu et al. 2004, Pathobiology 71:129-136; Sasahira et al. 2007, Virchows Arch 450:287-295; Kuniyasu et al. 2002, J Pathol 196:163-170; the entire content of each of which is incorporated herein by reference). Further to the above, Rai et al. (2012, J Exp Med 209:2339-2350) and Arumugam et al. (2012, Clin Canc Res 18:4356-4364), for example, describe animal model systems in which the contribution of RAGE to various cancers has been investigated and validated.

Further to the above, RAGE and its ligand HMGB1 are believed to play an important role in prostate cancer. Indeed, Zhao et al. (2014, Am J Cancer Res 4:369-377) addressed the significance of these effector molecules in a retrospective study designed to investigate the expression of RAGE and HMGB1 and their clinical impact on prostate cancer progression and prognosis. The expression of RAGE and HMGB1 was assessed by immunohistochemistry in cancer lesions from 85 confirmed prostate cancer cases. Zhao et al. demonstrated that there is a strong correlation between RAGE and HMGB1 expression (P<0.001) and the expression of RAGE, HMGB1 and their co-expression were all associated with advanced tumor clinical stage (P<0.05 for all). RAGE expression was also associated with the prostate specific antigen (PSA) level (P=0.014). Co-expression of RAGE and HMGB1 was also associated with poor overall survival in patients with stage III and IV prostate cancer (P=0.047). These results suggest that the expression of RAGE and HMGB1 is associated with progression and poor prognosis of prostate cancer. RAGE and HMGB1 are, therefore, proposed to be molecular targets for novel forms of therapy for prostate cancer.

Tumors/Tumorigenesis

Animal models for various forms of human cancers are known in the art and include those recapitulating aspects of human lung cancer, melanoma, colon cancer, pancreatic cancer, and breast cancer and bio-models of cancer for in silico screening. Such animal models are known in the art and are described in, for example, Taguchi et al. (2000, Nature 405: 354-360), Arumugam et al. (2004, Journal of Biological Chemistry 279:5059-5065), Huang et al. (2006, Surgery 139: 782-788), Huang et al. (2006, Surgery 139:782-788), Fuentes et al. (2007, Dis Colon Rectum 50:1230-1240), Arumugam et al. (2012, Clin Cancer Res 18: 4356-4364), Yu et al. (2014, J Gastric Cancer 14:67-86), Fleet (2014, Am J Physiol Gastrointest Liver Physiol. 307(3):G249-59), Lindner (2014, Semin Oncol 41: 146-155), Wang et al. (2014, Biofabrication 6(2):022001), Budhu et al. (2014, Curr Opin Genet Dev 24: 46-51, 2014); the entire content of each of which is incorporated herein by reference.

Ischemia/Reperfusion Injury

In, for example, animal models of hind limb ischemia in mice with or without diabetes, suppressing RAGE ligands has led to improvement of angiogenic response to limb ischemia. See, for example, Tamarat et al. (2003, Proc Natl Acad Sci 100:14); Goova et al. (2001, Am J Pathol 159:513-525); Tekabe et al. (2010, J Nuc Med 51:92-97); Tekabe et al. (2013, EJNMMi Res 3:37); Bucciarelli et al. (2008, Diabetes 57:1941-1951); Shang et al. (2010, PLoS 5:e10092); Ma et al. (2009, J Cell Mol Med 13:1751-1764); the entire content of each of which is incorporated herein by reference.

Erectile Dysfunction

Relaxation of the smooth muscle cells in the cavernosal arterioles and sinuses results in increased blood flow into the penis, raising corpus cavernosum pressure to culminate in penile erection. Nitric oxide is considered the principle stimulator of cavernosal smooth muscle relaxation (See Wingard et al. (2001, Nature Medicine 7:119-122). In that RAGE activation produces oxidants via an NADH oxidase-like enzyme (Yan et al. 1994, J. Biol. Chem. 269:9889-9887), it is thought to suppress nitric oxide circulation. Inhibiting activation of RAGE signaling pathways is, therefore, predicted to attenuate oxidant generation. Inhibition of RAGE-mediated activation of Rho-kinases is also predicted to enhance and stimulate penile erection independently of nitric oxide. Accordingly, compounds such as those described herein that act to inhibit downstream RAGE signaling may be used to advantage to promote and facilitate penile erection.

Respiratory Diseases

Patients with chronic obstructive pulmonary disease exhibit increased RAGE expression in the lung and elevated soluble RAGE levels in the bronchial alveolar fluid (Yan et al. 2003, Nature Med 9:287-293; Miniati et al. 2011, Respir Res 12:37). Increased RAGE receptor and ligand levels have also been detected in asthmatic patients (Watanabe et al. 2010, Respir Med 105:519-525), indicating an active role for RAGE in lung inflammation. See also Wu et al. (2013, Mol Cell Biochem 380:249-257); Sukkar et al. (2012, Br J Pharmacol 167:1161-1176).

Furthermore, in severe exacerbations of asthma there is an intense, mechanistically heterogeneous inflammatory response involving neutrophil and eosinophil accumulation and activation. Neutrophils are, moreover, a significant source of S100 proteins, key ligands for RAGE implicated in the propogation of the immune response and inflammation as described herein above. Accordingly, inhibitors of RAGE downstream signaling would be expected to be efficacious in the treatment of asthma. In that the propagation step in the immune response in the lung driven by S100-RAGE interaction is thought to lead to the activation and/or recruitment of inflammatory cells, such as neutrophils, which are significant sources of damaging proteases in chronic obstructive pulmonary diseases such as emphysema, the compounds described herein that act as RAGE inhibitors can be used to treat chronic obstructive pulmonary diseases.

Animal models for assessing the therapeutic potential of compounds described herein are presented in, for example, Akirav et al. (2014, PLoS One 9:e95678); and Constant et al. (2002, J Clin Invest 110:1441-1448); the entire content of each of which is incorporated herein by reference.

Amyloidoses

Compounds described herein are also envisioned as useful for treating amyloidoses and Alzheimer's Disease (AD). RAGE is known to bind β-sheet fibrillar material and deposition of amyloid has been shown to enhance expression of RAGE. The brains of AD patients exhibit increased expression of RAGE in neurons and glia (Yan et al. 1996, Nature 382:685-691). Binding of Aβ-RAGE on microglia activates these cells, as reflected by increased motility and expression of cytokines, whereas binding of Aβ-RAGE on neurons initially activates the cells, but ultimately leads to cytotoxicity. Inhibition of RAGE-amyloid interaction decreases expression of cellular RAGE and cell stress markers (as well as NF-κB activation) and diminishes amyloid deposition (Yan et al. 2000, Nat. Med. 6:643-651). These findings suggest that a role for RAGE-amyloid interaction exists, both with respect to perturbation of cellular properties in an environment enriched for amyloid at early stages of disease and progressively during the course of disease as amyloid accumulates.

Neurodegeneration

Animal models of human neurodegenerative diseases are known and include mouse models of Alzheimer's Disease, humanized mouse models of Amyotrophic lateral sclerosis, and mouse models of Huntington's disease. Such animal models are described in, for example, Millington et al. (2014, Biomed Res Inst 2014:309129), Yan et al. (1996, Nature 382:685-691), Yan et al. (1997, Proc. Natl. Acad. Sci. 94:5296-5301), Bard et al. (2014, J Biomol Screen 19: 191-204), Neha et al. (2014, Life Sci 109(2):73-86), and Turner et al. (2013, Amyotroph Lateral Scler Frontotemporal Degener. 14 Suppl 1:19-32); the entire content of each of which is incorporated herein by reference.

Atherosclerosis

Examples of animal models of human atherosclerotic disease include apolipoprotein E null mice and Low Density Lipoprotein Receptor null mice. See, for example, Kapourchali et al. (2014, World J Clin Cases 2: 126-132), Harja et al. (2008, J. Clin. Invest. 1118: 183-194), Nagareddy et al. (2013, Cell Metab 17: 695-708); the entire content of each of which is incorporated herein by reference.

In light of that which is understood in the art and described herein regarding the prominent role of RAGE in diseases/conditions characterized by acute and chronic inflammation, methods are presented herein for treating such diseases/conditions, including but not limited to diabetic complications, ischemia, skin inflammation (e.g., psoriasis and atopic dermatitis), lung inflammation (e.g., asthma and chronic obstructive pulmonary disease), vascular permeability, nephropathy, atherosclerosis, retinopathy, Alzheimer's Disease, erectile dysfunction, and tumor invasion and/or metastasis, which methods comprise administering to a subject in need thereof a compound described herein in a therapeutically effective amount. In a particular embodiment, at least one compound described herein is utilized, either alone or in combination with one or more known therapeutic agents. In a further particular embodiment, the present invention provides a method for treating RAGE mediated human diseases, wherein treatment alleviates one or more symptoms resulting from that disorder, the method comprising administration to a human in need thereof a therapeutically effective amount of a compound described herein.

In vitro assays relating to RAGE-mediated diseases and animal model systems thereof are described in US2012/0088778, US2010/0254983, US2010/0119512, U.S. Pat. No. 7,361,678, WO2007/089616, and US2010/0249038, the entire content of each of which is incorporated herein by reference.

Further to the above, the present compounds are modulators of interaction between RAGE and RAGE ligands and are used as therapeutic agents for the treatment of conditions in mammals that are causally related or attributable to RAGE activity. Accordingly, the compounds and pharmaceutical compositions of this invention find use as therapeutics for preventing and/or treating a variety of conditions related to, for example, diabetes complications in mammals, including humans.

In a method of treatment aspect, this invention provides a method of treating a mammal susceptible to or afflicted with a condition associated with diabetes complications, Alzheimer's disease, cancers, arthritis, nephropathy, acute and chronic inflammation, retinopathy, atherosclerosis, erectile dysfunction, tumor invasion and metastasis, and others, which method comprises administering an effective amount of one or more of the pharmaceutical compositions just described.

In additional method of treatment aspects, this invention provides methods of treating a mammal susceptible to or afflicted with an inflammatory condition causally related or attributable to RAGE activity. Such condition and disorders include, without limitation, diabetes and its complications, impaired wound healing, peripheral vascular disease and associated complications, obesity, Alzheimer's disease, cancers, arthritis, nephropathy, acute and chronic inflammation, retinopathy, atherosclerosis, cardiovascular disease, erectile dysfunction, tumor invasion and metastases, neuropathy, cardio- and cerebrovascular ischemia/reperfusion injury, heart attack, stroke, myocardial infarction, ischemic cardiomyopathy, renal ischemia, sepsis, pneumonia, infection, liver injury, liver damage, Amyotrophic lateral sclerosis, neuropathy infection, allergy, asthma, organ damage from pollutants, amyloidoses asthma, pollution-associated tissue damage, skin disorders, colitis, skin aging, lupus, and others. Such methods comprise administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases. Also provided herein are the present compounds for use in treating or preventing one of the aforementioned conditions and diseases, wherein at least one of the compounds described herein is administered to a subject in need thereof in a therapeutically effective amount sufficient to antagonize/reduce RAGE activity and thereby treat the condition or disease.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., arthritis, diabetes, or asthma, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery models based on a variety of parameters, including the organ or tissue site in a patient with a disease or condition that is most severely affected by the disease or condition.

When used to prevent the onset of an inflammatory condition or autoimmune disorder, the compounds of this invention will be administered to a patient at risk for developing the condition or disorder, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

General Synthetic Procedures

The amino, amido, and heterocyclic compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of the invention may be prepared from known or commercially available starting materials and reagents by one skilled in the art of organic synthesis.

For example, exemplary compounds of formula B-I' and B-I can be prepared following the methods described in Schemes 1 and 2.

Scheme 1

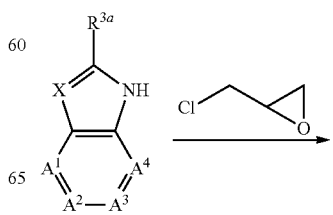

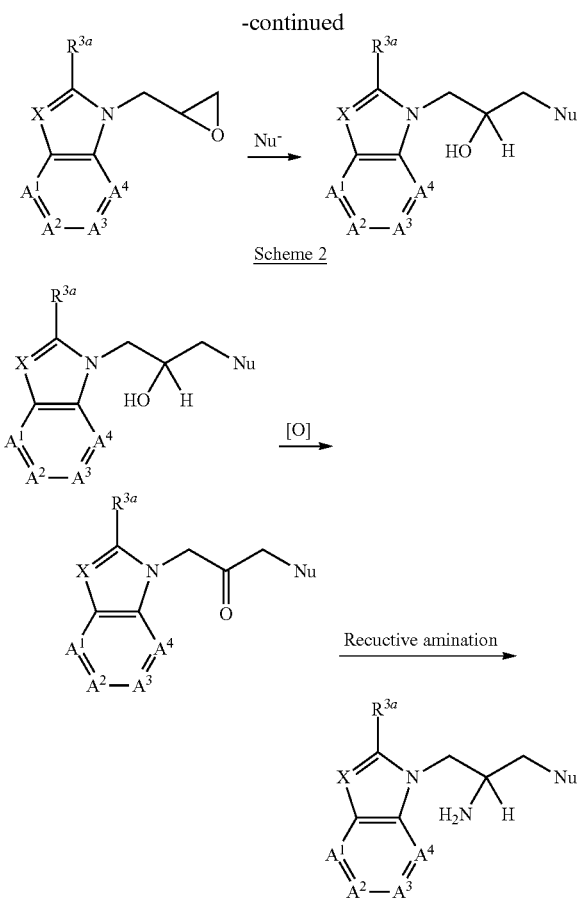

Assay Methods

Primary Screen (High-Throughput Screening Assay)

Figure 4:
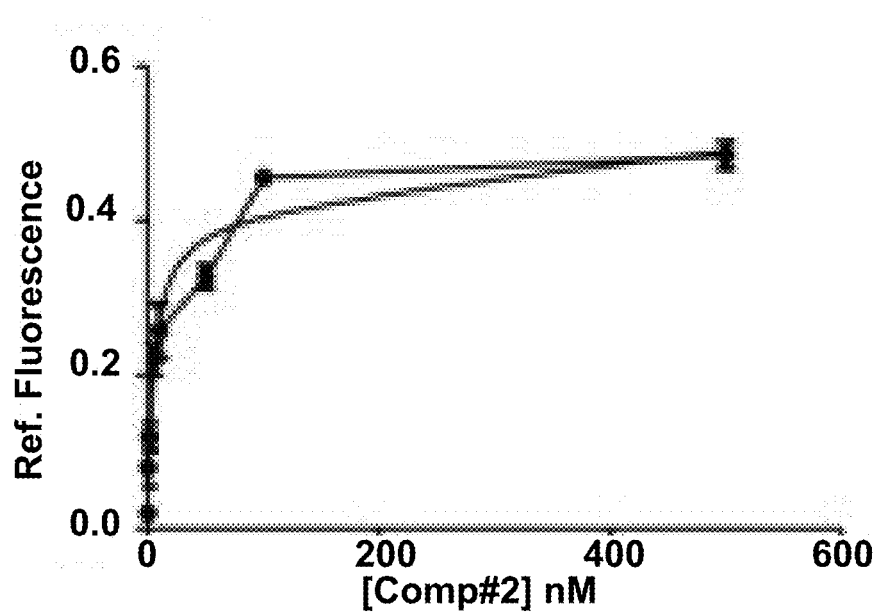
FIG. 4 shows RAGE tail Fluorescence Titration data for Compound CB-2 (formula B-II).
Figure 5:
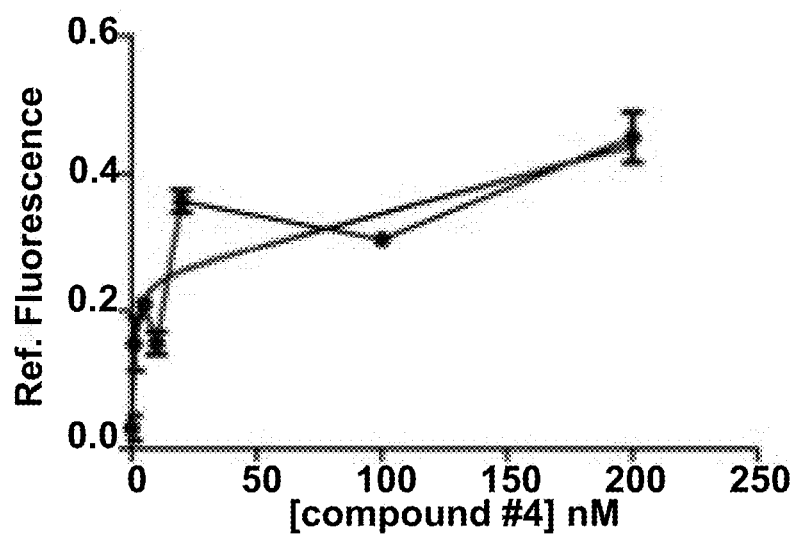
FIG. 5 shows RAGE tail Fluorescence Titration data for Compound CB-4 (formula B-XIIIa).

Primary screening was a two-step process in which compounds were first tested in a high throughput assay at one concentration (10 uM). Compounds that reduced binding of RAGE tail (ctRAGE) by at least 50% were then selected and subjected to 4-point dose response (10 uM, 1 uM, 0.1 uM and 0.01 uM) (FIGS. 1, 4, and 5). Compounds that demonstrated a clear dose dependence were then selected for secondary screening.

Secondary Screen

The goal of the secondary screening was to observe direct binding of compounds to ctRAGE. To form a compound-RAGE tail complex, the inventors added 5 uM of each compound dissolved in DMSO to 500 uL of 5 uM uniformly $^{15}$N-labeled RAGE tail in 10 mM potassium phosphate buffer, pH 6.5. The changes caused by compound binding to RAGE tail were monitored by using heteronuclear NMR experiment, $^{15}$N-HSQC. This experiment facilitates monitoring chemical changes of backbone amide protons and nitrogens of RAGE tail due to compound binding (See below) [11].

The method used herein has been described by Rai et al. (*J Biol Chem* 287, 5133-5144), the entire content of which is incorporated herein by reference.

High resolution NMR spectroscopy is widely used to screen small molecule libraries. By using a technique called chemical shift perturbation, NMR spectroscopy provides a relatively fast and direct way to observe/identify the binding epitopes of a protein for a small molecule. Each NMR active nucleus, $^1$H, $^{13}$C and $^{15}$N, in a $^{13}$C and/or $^{15}$N-labeled protein, exhibits a unique chemical shift that reflects its chemical environment in the molecular structure, and is exquisitely sensitive to changes in that environment caused by small molecule binding to the protein. Standard NMR assignment procedures the inventors to determine the chemical shifts for all NMR active nuclei in the protein of interest. Since changes in these chemical shifts reflect structural changes in the immediate vicinity of the small molecule binding site on the protein, quantifying the changes and mapping affected amino acids on the 3D protein structure unambiguously confirm the binding event and also define the small molecule-protein interaction surface at atomic resolution.

NMR spectroscopy allows the inventors to estimate binding affinities depending on the magnitude of the chemical shift change $\Delta\Omega$ and the rate constant, $k_{off}$, between bound and free states. Chemical exchange can result in gradual changes of chemical shifts when $\Delta\Omega<<k_{off}$ (fast exchange), line broadening when $\Delta\Omega\leq k_{off}$ (intermediate exchange) or the appearance of new peaks when $\Delta\Omega>>k_{off}$ (slow exchange). Assuming that the binding reaction is diffusion limited and the average change of the $^1$H chemical shift is ~0.1 ppm, the fast exchange regime will occur when the dissociation constant, $K_d$, is larger than 100 uM and intermediate or slow exchange will occur when the dissociation constant is less than or equal to 10 uM. Binding stoichiometry can be established when no further changes in the chemical shifts or differential broadening of specific peaks in the NMR spectra occur as the molar ratio of small molecule to protein increases. The binding affinities can be estimated by using the complementary method of surface plasmon resonance (SPR) and/or fluorescence titration.

To distinguish $^{15}$N- and/or $^{13}$C-labeled protein NMR signals from those originating from a small molecule, the chemical shift perturbation technique employs a $^{15}$N and/or $^{13}$C edited experiment known as heteronuclear single quantum coherence (HSQC). Each peak in the HSQC spectrum corresponds to a $^1$H—$^{15}$N and/or $^1$H—$^{13}$C bond in the protein. A 700 MHz NMR spectrometer equipped with an ultrasensitive cryoprobe is used to conduct the assays; the combination of high magnetic field and a cryoprobe significantly improves the sensitivity of NMR experiments.

Procedure

Figure 2:
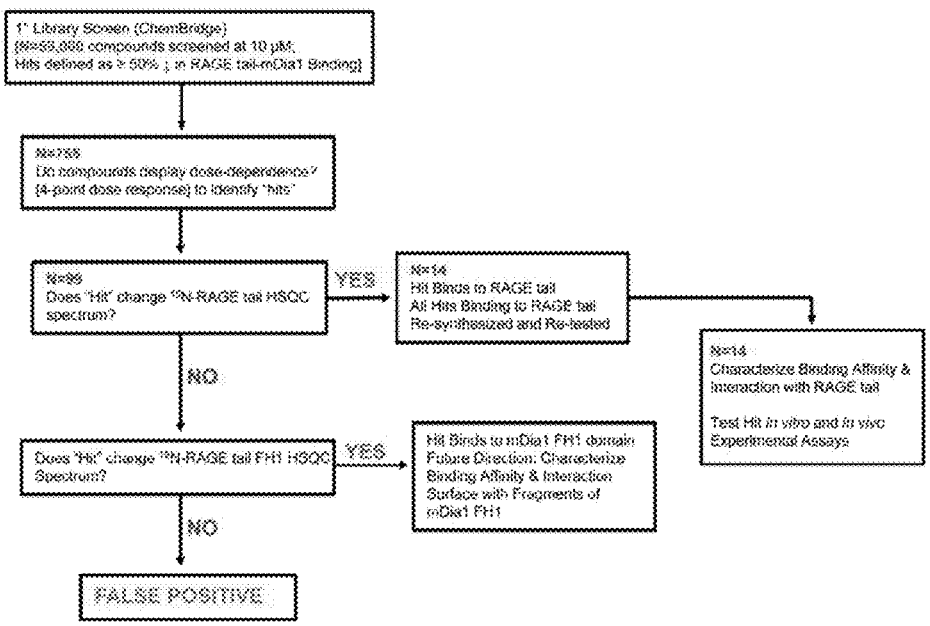
FIG. 2 shows a flow chart for Secondary screening using NMR spectroscopy.

There are two possible modes of blocking complex formation between RAGE tail and the FH1 domain of Dia-1: A small molecule binds either to RAGE tail or the FH1 domain and obstructs the RAGE tail-FH1 interaction surface. RAGE tail is a small, 43 amino acid peptide. It is only partially folded. A solution structure of a N-terminal fragment of RAGE tail is determined by the inventors. The FH1 domain is a 260 amino acid fragment of Dia-1 containing multiple polyproline stretches. According to the preliminary results, FH1 does not have a well-defined tertiary structure. Based on our preliminary results, the $^{15}$N-HSQC spectra of both free $^{15}$N-CT-RAGE and the $^{15}$N-CT-RAGE-FH1 complex contain well resolved peaks that have been assigned to facilitate chemical shift perturbation screening. Thus, for the first round of the screen (FIG. 2), the $^{15}$N-HSQC spectral changes of either free $^{15}$N-CT-RAGE or a $^{15}$N-CT-RAGE-FH1 complex induced by small molecule binding are observed. The screenings are conducted by titrating up to 10 μM of a small molecule to 10 μM of the protein sample; small molecules that bind to CT-RAGE or FH1 with affinities weaker than 10 μM are unlikely be of interest for biological studies and are not pursued.

In general, if a small molecule binds to CT-RAGE then corresponding changes in the $^{15}$N-HSQC spectrum of free $^{15}$N-CT-RAGE will be observed.

If a small molecule binds to the FH1 domain then no changes will be observed in the $^{15}$N-HSQC spectrum of free $^{15}$N-CT-RAGE. However, specific changes in the $^{15}$N-HSQC spectrum of $^{15}$N-CT-RAGE-FH1 will be observed.

At the titration endpoint, the $^{15}$N-HSQC spectrum of $^{15}$N-CT-RAGE-FH1 will be similar to the spectrum of free $^{15}$N-CT-RAGE.

Binding affinities of small molecules for either CT-RAGE or FH1 are determined by performing fluorescence titrations to generate binding isotherms and standard SPR experiments.

EXAMPLES

As detailed above, in order to identify small molecules to antagonize RAGE activity, the present inventors developed primary screening assay.

From screening a chemical compounds library consisting of 59,000 compounds, a number of compounds were identified as small molecule inhibitors for the RAGE activity.

Example 1

Representative Method and Protocol for Primary Screening

Day 1

Step 1. Add 50 µl anti-mDia1 (1:160 dilution in 0.1M NaHCO$_3$ pH 9.6)/well. Incubate overnight at 4° C.

Day 2

Step 2. Use the plate washer to aspirate anti-mDia1 and wash plates 4× with PBS 100 µl per well per wash.

Step 3. Add 180 µl 3% BSA in 1×PBS. Incubate for 1.5 hrs at room temperature

Step 4. Use the plate washer to aspirate the blocking solution and wash 5× with PBS 300 µl per well.

Step 5. Add 50 µl of mDia1 containing lysate (85 µg) and incubate at RT for 3 hours.

Step 6. Aspirate the lysate and wash the plate 5× (100 µl) on the plate washer.

Step 7. Add 25 µl PBS to the wells.

Step 8. Add 0.5 µL compound per well.

Step 9. Add 24.5 µL GFP RAGE tail (125 nM) into each well for 2 hrs at room temperature.

Step 10. Aspirate and wash 5× with PBS (100 µL) on the plate washer.

Step 11. Add 100 ul PBS in each well.

Step 12. Detection: Read on fluorescence plate reader excitation 435 nm and 485 nm emission Compounds that blocked the binding of RAGE tail to mDia1 by 50% or more were subjected to 4 point dose response: 10 µM, 1 µM, 0.1 µM and 0.01 µM.

Compounds that showed dose dependence were then subjected to secondary screen:

K$_d$ Determinations

A number of representative amino and amido compounds of this invention were or can be tested for their inhibitory activity. The amino and amido compounds of the invention along with their available K$_d$ values, as determined using conventional methods to those skilled in the art, are listed below in Table 1.

TABLE 1

Exemplary Amino, amido, and heterocyclic Compounds and available K$_d$ Values

| Compd # | Structure | MW (Calcd) | K$_d$ (nM) |
|---|---|---|---|
| CB-1 | MeS-phenyl(OMe)-C(O)NH-pyridine-Me | 288.37 | 4 ± 1 |
| CB-5 | HO-phenyl-NH-thiazole-phenyl(F)(F) | 304.32 | 1.1 ± 0.2 |
| CB-6 | Ac-NH-phenyl(Cl)(OMe)-C(O)NH-thiazole | 325.78 | 0.1 ± 0.05 |

TABLE 1-continued

Exemplary Amino, amido, and heterocyclic Compounds and available $K_d$ Values

| Compd # | Structure | MW (Calcd) | $K_d$ (nM) |
|---|---|---|---|
| CB-7 | 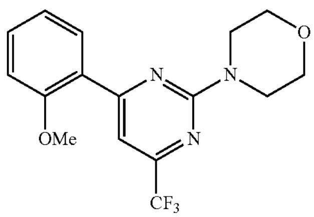 [SMILES: COc1ccccc1-c1cc(C(F)(F)F)nc(N2CCOCC2)n1] | 339.32 | 0.55 ± 0.05 |
| CB-8 | 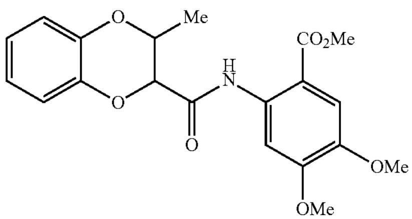 [SMILES: COC(=O)c1cc(OC)c(OC)cc1NC(=O)C1Oc2ccccc2OC1C] | 387.39 | 2.0 ± 0.5 |
| CB-13 | 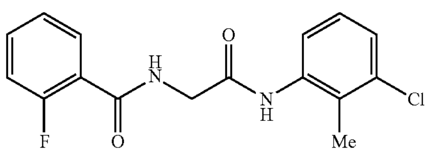 [SMILES: Cc1c(Cl)cccc1NC(=O)CNC(=O)c1ccccc1F] | 320.75 | 123 ± 1 |
| CB-14 | 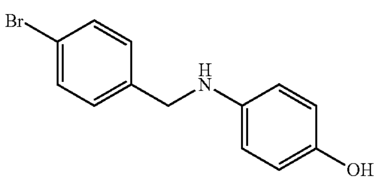 [SMILES: Oc1ccc(NCc2ccc(Br)cc2)cc1] | 278.15 | 1.4 ± 0.3 |
| CD-1 | 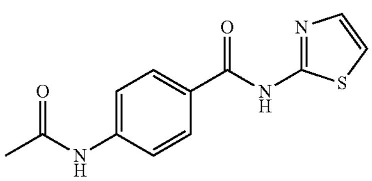 [SMILES: CC(=O)Nc1ccc(C(=O)Nc2nccs2)cc1] | | 31% Inhibition @ 10 μM |
| CD-21 | 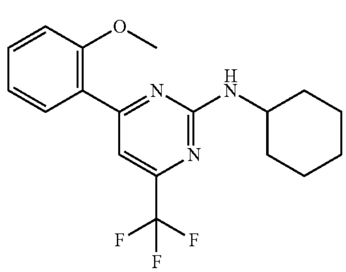 [SMILES: COc1ccccc1-c1cc(C(F)(F)F)nc(NC2CCCCC2)n1] | | 18% Inhibition @ 10 μM |

TABLE 1-continued

Exemplary Amino, amido, and heterocyclic Compounds and available $K_d$ Values

| Compd # | Structure | MW (Calcd) | $K_d$ (nM) |
|---|---|---|---|
| CD-42 | 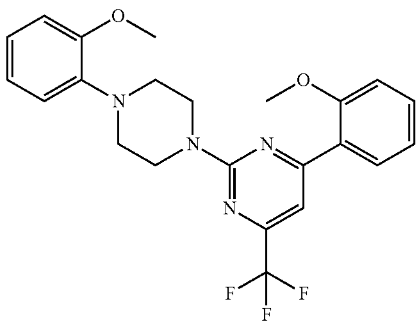 [SMILES: COc1ccccc1-c1cc(C(F)(F)F)nc(N2CCN(c3ccccc3OC)CC2)n1] | | 42% Inhibition @ 10 μM |

Compound#CB-1 was titrated into 100 nM solution of RAGE tail. Fluorescence quenching was used to determine binding. R2 quality factor of the fitting was 0.86 (FIG. 1).

Additional representative amido compounds according to formula A-I are listed below in Table 2.

TABLE 2

Additional Representative Compounds

| ID | STRUCTURE | MW |
|---|---|---|
| 201 | 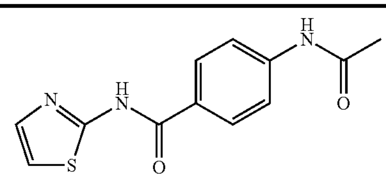 | 261.30 |
| 202 | 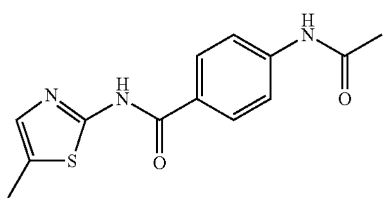 [SMILES: CC(=O)Nc1ccc(C(=O)Nc2ncc(C)s2)cc1] | 275.33 |
| 203 | 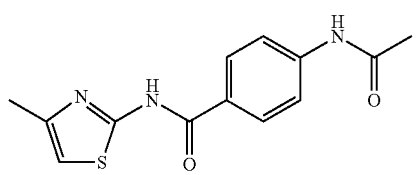 [SMILES: CC(=O)Nc1ccc(C(=O)Nc2nc(C)cs2)cc1] | 275.33 |
| 204 | 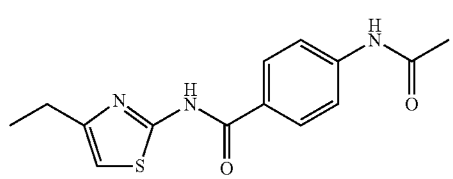 [SMILES: CCc1csc(NC(=O)c2ccc(NC(C)=O)cc2)n1] | 289.36 |
| 205 | 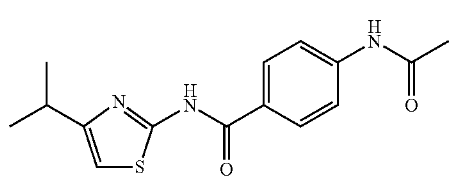 [SMILES: CC(=O)Nc1ccc(C(=O)Nc2nc(C(C)C)cs2)cc1] | 303.39 |

US 9,353,078 B2
TABLE 2-continued
Additional Representative Compounds
| ID | STRUCTURE | MW |
|---|---|---|
| 206 | 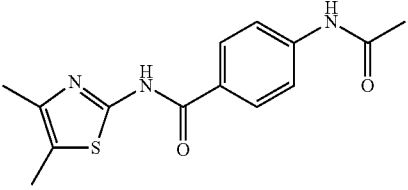 [SMILES: CC(=O)Nc1ccc(C(=O)Nc2nc(C)c(C)s2)cc1] | 289.36 |
| 207 | 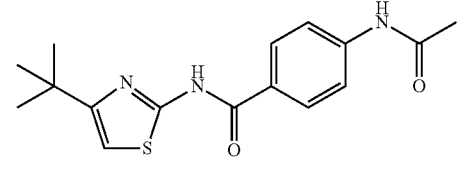 [SMILES: CC(=O)Nc1ccc(C(=O)Nc2nc(C(C)(C)C)cs2)cc1] | 317.41 |
| 208 | 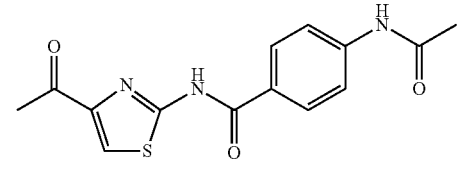 [SMILES: CC(=O)Nc1ccc(C(=O)Nc2nc(C(C)=O)cs2)cc1] | 303.34 |
| 209 | 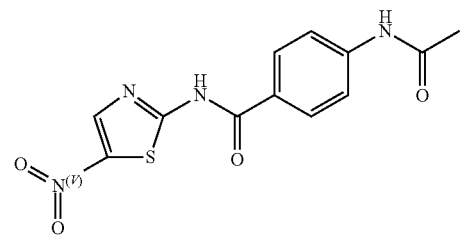 [SMILES: CC(=O)Nc1ccc(C(=O)Nc2ncc([N+](=O)[O-])s2)cc1] | 306.30 |
| 210 | 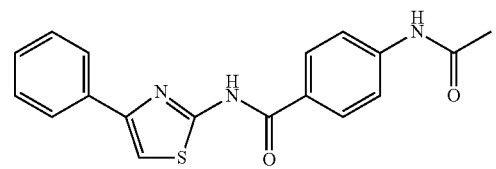 [SMILES: CC(=O)Nc1ccc(C(=O)Nc2nc(-c3ccccc3)cs2)cc1] | 337.40 |
| 211 | 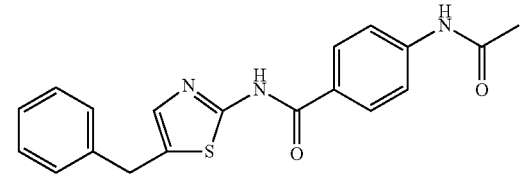 [SMILES: CC(=O)Nc1ccc(C(=O)Nc2ncc(Cc3ccccc3)s2)cc1] | 351.43 |
| 212 | 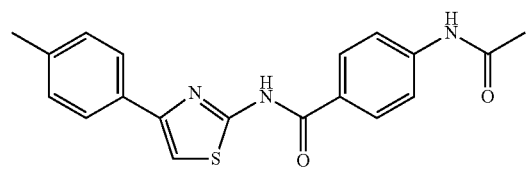 [SMILES: CC(=O)Nc1ccc(C(=O)Nc2nc(-c3ccc(C)cc3)cs2)cc1] | 351.43 |

TABLE 2-continued

Additional Representative Compounds

| ID | STRUCTURE | MW |
|----|-----------|-----|
| 213 | 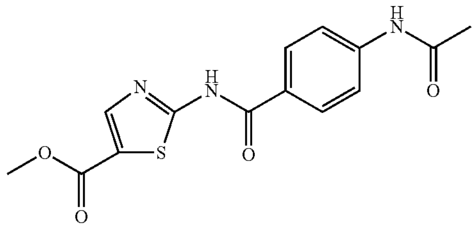 [SMILES: COC(=O)c1cnc(NC(=O)c2ccc(NC(C)=O)cc2)s1] | 319.34 |
| 214 | 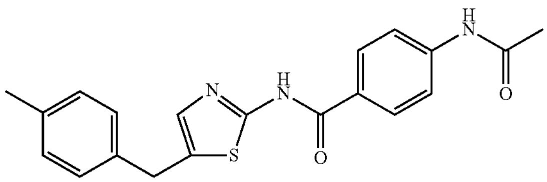 [SMILES: CC(=O)Nc1ccc(C(=O)Nc2ncc(Cc3ccc(C)cc3)s2)cc1] | 365.46 |
| 215 | 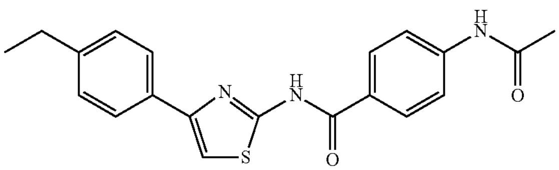 [SMILES: CCc1ccc(-c2csc(NC(=O)c3ccc(NC(C)=O)cc3)n2)cc1] | 365.46 |
| 216 | 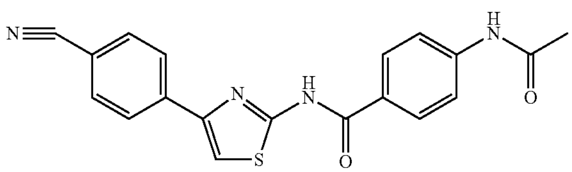 [SMILES: CC(=O)Nc1ccc(C(=O)Nc2nc(-c3ccc(C#N)cc3)cs2)cc1] | 362.41 |
| 217 | 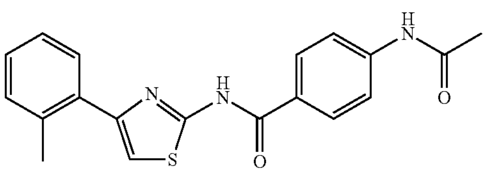 [SMILES: CC(=O)Nc1ccc(C(=O)Nc2nc(-c3ccccc3C)cs2)cc1] | 351.43 |
| 218 | 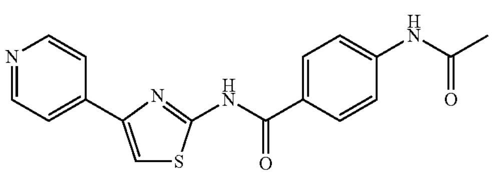 [SMILES: CC(=O)Nc1ccc(C(=O)Nc2nc(-c3ccncc3)cs2)cc1] | 338.39 |
| 219 | 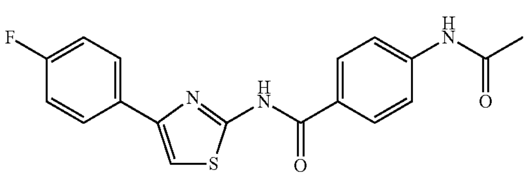 [SMILES: CC(=O)Nc1ccc(C(=O)Nc2nc(-c3ccc(F)cc3)cs2)cc1] | 355.39 |
| 220 | 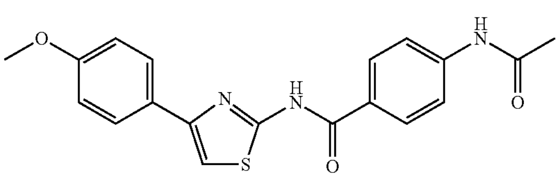 | 367.43 |

TABLE 2-continued
Additional Representative Compounds
| ID | STRUCTURE | MW |
|---|---|---|
| 221 | 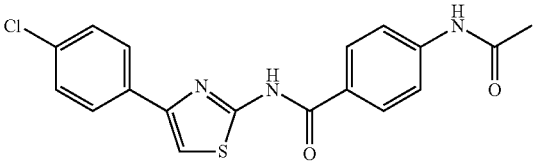 [SMILES: CC(=O)Nc1ccc(C(=O)Nc2nc(-c3ccc(Cl)cc3)cs2)cc1] | 371.85 |
| 222 | 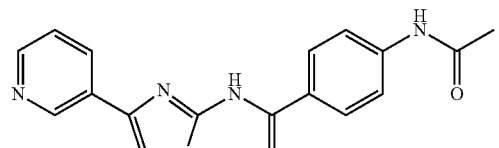 | 338.39 |
| 223 | 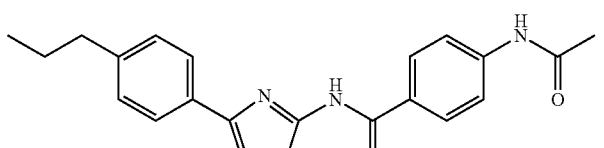 | 379.48 |
| 224 | 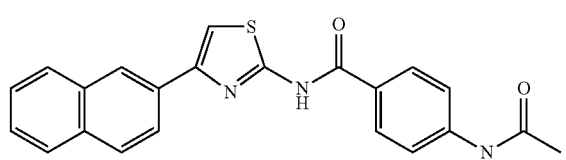 | 387.46 |
| 225 | 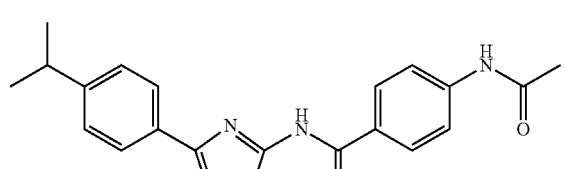 | 379.48 |
| 226 | 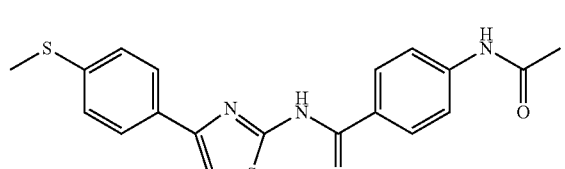 | 383.49 |
| 227 | 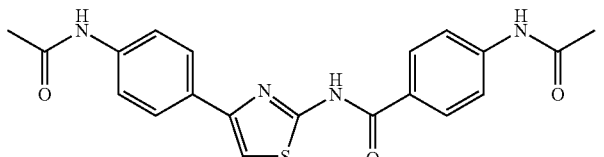 | 394.46 |
| 228 | 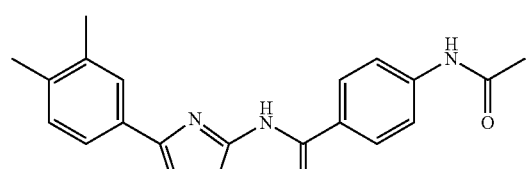 | 365.46 |

TABLE 2-continued
Additional Representative Compounds
| ID | STRUCTURE | MW |
|---|---|---|
| 229 | 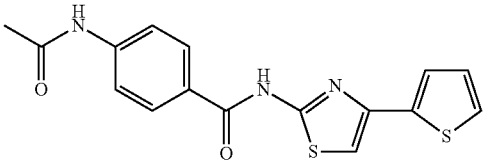 [SMILES: CC(=O)Nc1ccc(C(=O)Nc2nc(-c3cccs3)cs2)cc1] | 343.43 |
| 230 | 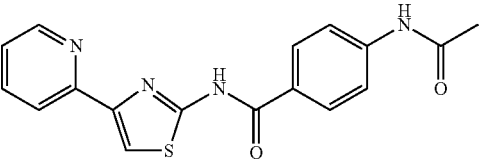 [SMILES: CC(=O)Nc1ccc(C(=O)Nc2nc(-c3ccccn3)cs2)cc1] | 338.39 |
| 231 | 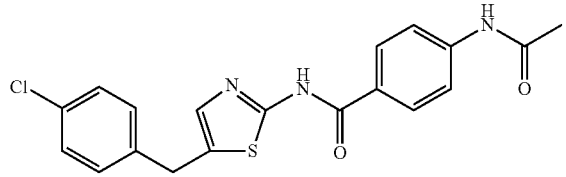 [SMILES: CC(=O)Nc1ccc(C(=O)Nc2ncc(Cc3ccc(Cl)cc3)s2)cc1] | 385.88 |
| 232 | 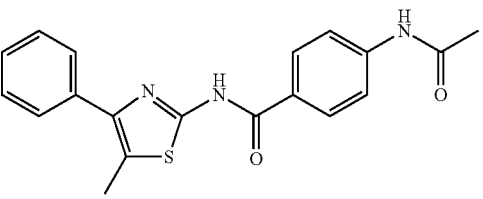 [SMILES: CC(=O)Nc1ccc(C(=O)Nc2nc(-c3ccccc3)c(C)s2)cc1] | 351.43 |
| 233 | 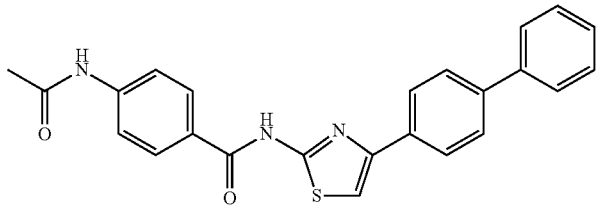 [SMILES: CC(=O)Nc1ccc(C(=O)Nc2nc(-c3ccc(-c4ccccc4)cc3)cs2)cc1] | 413.50 |
| 234 | 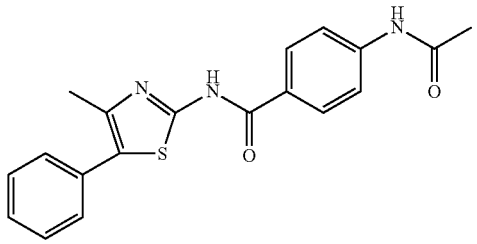 [SMILES: CC(=O)Nc1ccc(C(=O)Nc2nc(C)c(-c3ccccc3)s2)cc1] | 351.43 |
| 235 | 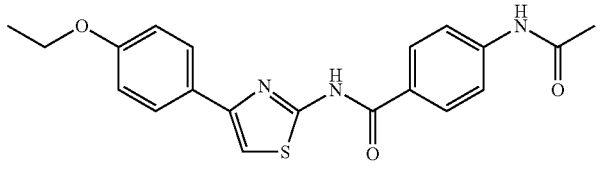 [SMILES: CCOc1ccc(-c2csc(NC(=O)c3ccc(NC(C)=O)cc3)n2)cc1] | 381.46 |
| 236 | 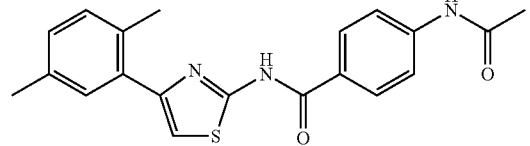 | 365.46 |

TABLE 2-continued

Additional Representative Compounds

| ID | STRUCTURE | MW |
|---|---|---|
| 237 | 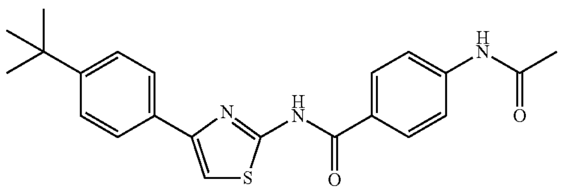 [SMILES: CC(=O)Nc1ccc(C(=O)Nc2nc(-c3ccc(C(C)(C)C)cc3)cs2)cc1] | 393.51 |
| 238 | 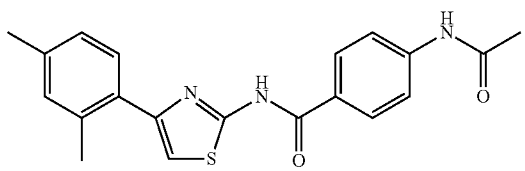 [SMILES: CC(=O)Nc1ccc(C(=O)Nc2nc(-c3ccc(C)cc3C)cs2)cc1] | 365.46 |
| 239 | 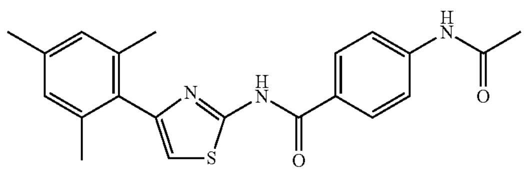 [SMILES: CC(=O)Nc1ccc(C(=O)Nc2nc(-c3c(C)cc(C)cc3C)cs2)cc1] | 379.48 |
| 240 | 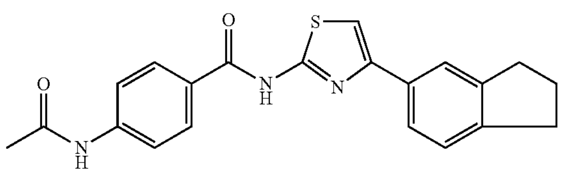 [SMILES: CC(=O)Nc1ccc(C(=O)Nc2nc(-c3ccc4c(c3)CCC4)cs2)cc1] | 377.47 |
| 241 | 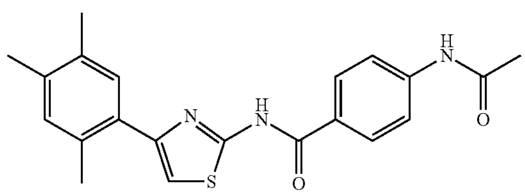 [SMILES: CC(=O)Nc1ccc(C(=O)Nc2nc(-c3cc(C)c(C)cc3C)cs2)cc1] | 379.48 |
| 242 | 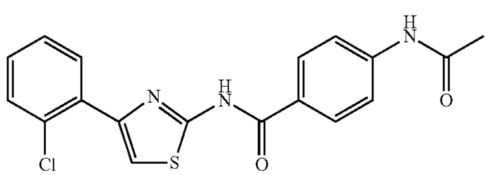 [SMILES: CC(=O)Nc1ccc(C(=O)Nc2nc(-c3ccccc3Cl)cs2)cc1] | 371.85 |
| 243 | 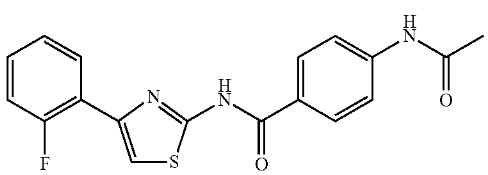 [SMILES: CC(=O)Nc1ccc(C(=O)Nc2nc(-c3ccccc3F)cs2)cc1] | 355.39 |
| 244 | 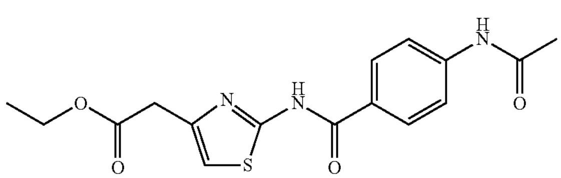 [SMILES: CCOC(=O)Cc1csc(NC(=O)c2ccc(NC(C)=O)cc2)n1] | 347.40 |

TABLE 2-continued

Additional Representative Compounds

| ID | STRUCTURE | MW |
|---|---|---|
| 245 | 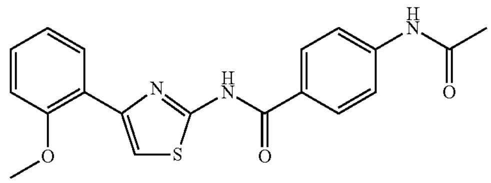 [SMILES: COc1ccccc1-c1csc(NC(=O)c2ccc(NC(C)=O)cc2)n1] | 367.43 |
| 246 | 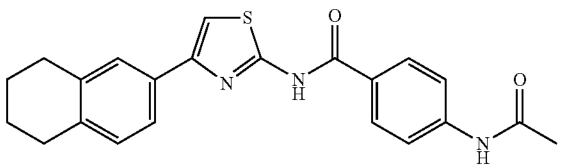 [SMILES: CC(=O)Nc1ccc(C(=O)Nc2nc(-c3ccc4c(c3)CCCC4)cs2)cc1] | 391.50 |
| 247 | 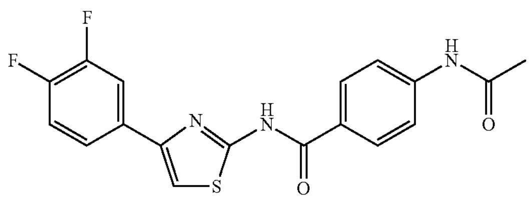 [SMILES: CC(=O)Nc1ccc(C(=O)Nc2nc(-c3ccc(F)c(F)c3)cs2)cc1] | 373.38 |
| 248 | 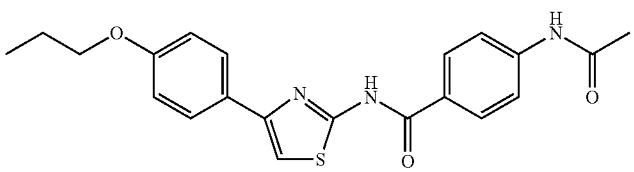 [SMILES: CCCOc1ccc(-c2csc(NC(=O)c3ccc(NC(C)=O)cc3)n2)cc1] | 395.48 |
| 249 | 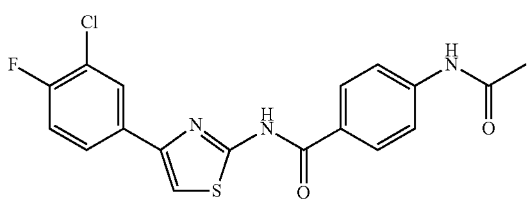 [SMILES: CC(=O)Nc1ccc(C(=O)Nc2nc(-c3ccc(F)c(Cl)c3)cs2)cc1] | 389.84 |
| 250 | 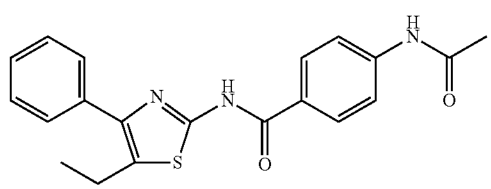 [SMILES: CCc1sc(NC(=O)c2ccc(NC(C)=O)cc2)nc1-c1ccccc1] | 365.46 |
| 251 | 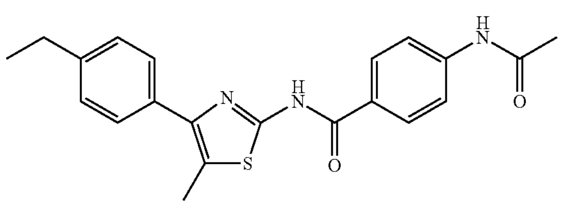 | 379.48 |
| 252 | 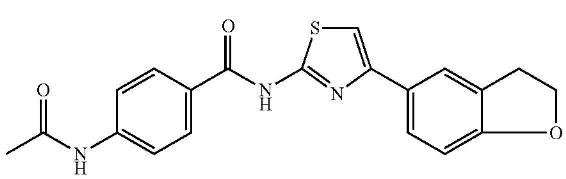 [SMILES: CC(=O)Nc1ccc(C(=O)Nc2nc(-c3ccc4c(c3)CCO4)cs2)cc1] | 379.44 |

TABLE 2-continued

Additional Representative Compounds

| ID | STRUCTURE | MW |
|---|---|---|
| 253 | 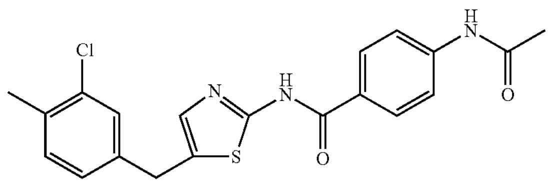 [SMILES: CC(=O)Nc1ccc(C(=O)Nc2ncc(Cc3ccc(C)c(Cl)c3)s2)cc1] | 399.90 |
| 254 | 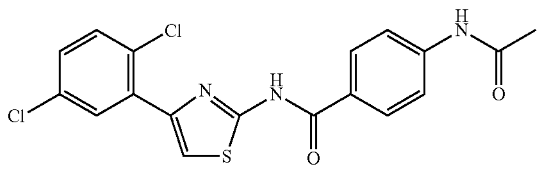 [SMILES: CC(=O)Nc1ccc(C(=O)Nc2nc(-c3cc(Cl)ccc3Cl)cs2)cc1] | 406.29 |
| 255 | 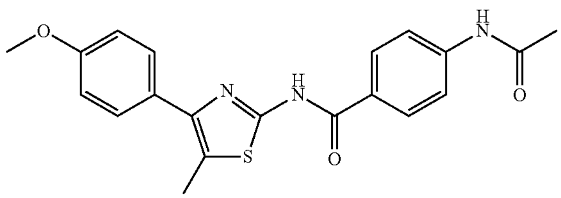 [SMILES: COc1ccc(-c2nc(NC(=O)c3ccc(NC(C)=O)cc3)sc2C)cc1] | 381.46 |
| 256 | 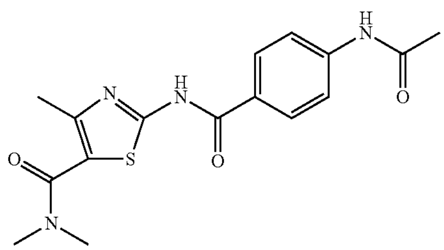 [SMILES: CC(=O)Nc1ccc(C(=O)Nc2nc(C)c(C(=O)N(C)C)s2)cc1] | 346.41 |
| 257 | 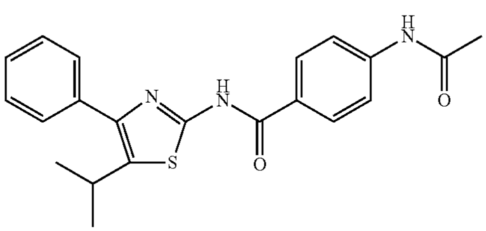 [SMILES: CC(=O)Nc1ccc(C(=O)Nc2nc(-c3ccccc3)c(C(C)C)s2)cc1] | 379.48 |
| 258 | 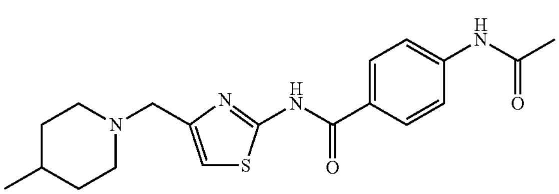 [SMILES: CC(=O)Nc1ccc(C(=O)Nc2nc(CN3CCC(C)CC3)cs2)cc1] | 372.49 |
| 259 | 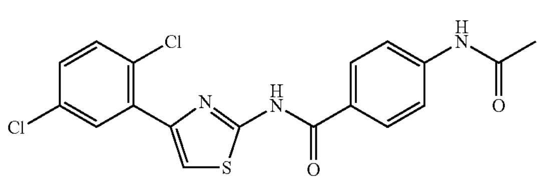 [SMILES: CC(=O)Nc1ccc(C(=O)Nc2nc(-c3cc(Cl)ccc3Cl)cs2)cc1] | 406.29 |

TABLE 2-continued

Additional Representative Compounds

| ID | STRUCTURE | MW |
|---|---|---|
| 260 | 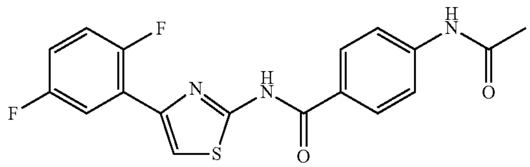 [SMILES: CC(=O)Nc1ccc(C(=O)Nc2nc(-c3cc(F)ccc3F)cs2)cc1] | 373.38 |
| 261 | 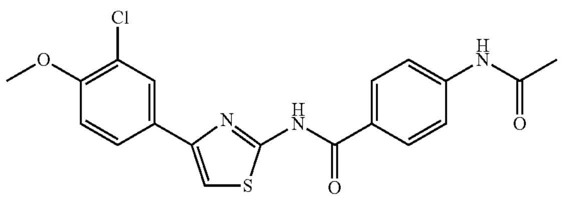 [SMILES: COc1ccc(-c2csc(NC(=O)c3ccc(NC(C)=O)cc3)n2)cc1Cl] | 401.87 |
| 262 | 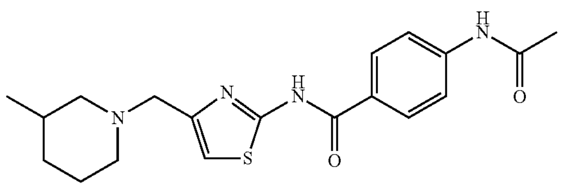 [SMILES: CC(=O)Nc1ccc(C(=O)Nc2nc(CN3CCCC(C)C3)cs2)cc1] | 372.49 |
| 263 | 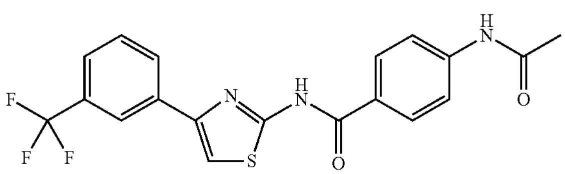 [SMILES: CC(=O)Nc1ccc(C(=O)Nc2nc(-c3cccc(C(F)(F)F)c3)cs2)cc1] | 405.40 |
| 264 | 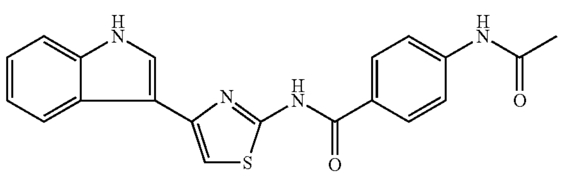 [SMILES: CC(=O)Nc1ccc(C(=O)Nc2nc(-c3c[nH]c4ccccc34)cs2)cc1] | 376.44 |
| 265 | 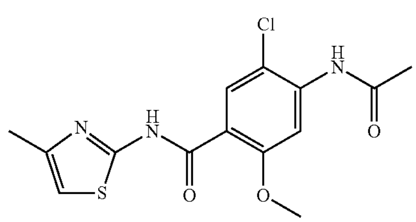 [SMILES: COc1cc(NC(C)=O)c(Cl)cc1C(=O)Nc1nc(C)cs1] | 339.80 |
| 266 | 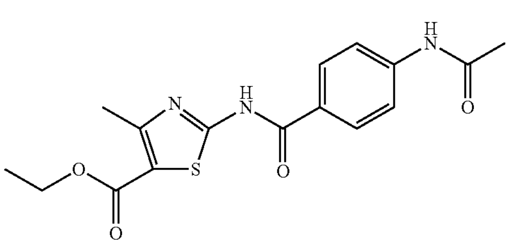 [SMILES: CCOC(=O)c1sc(NC(=O)c2ccc(NC(C)=O)cc2)nc1C] | 347.40 |

TABLE 2-continued
Additional Representative Compounds
| ID | STRUCTURE | MW |
|---|---|---|
| 267 | 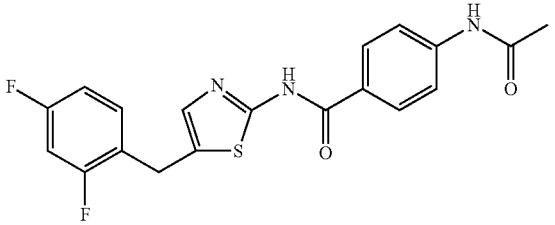 [SMILES: CC(=O)Nc1ccc(C(=O)Nc2ncc(Cc3ccc(F)cc3F)s2)cc1] | 387.41 |
| 268 | 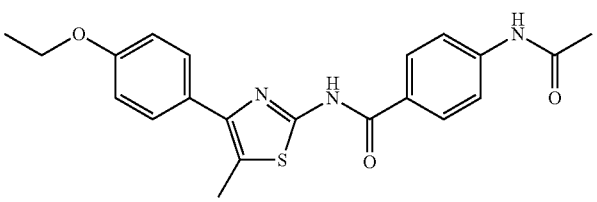 [SMILES: CCOc1ccc(-c2nc(NC(=O)c3ccc(NC(C)=O)cc3)sc2C)cc1] | 395.48 |
| 269 | 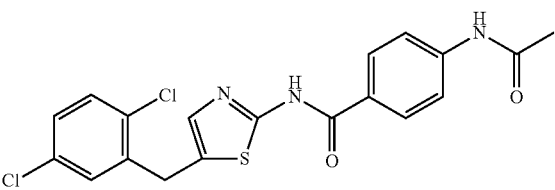 [SMILES: CC(=O)Nc1ccc(C(=O)Nc2ncc(Cc3cc(Cl)ccc3Cl)s2)cc1] | 420.32 |
| 270 | 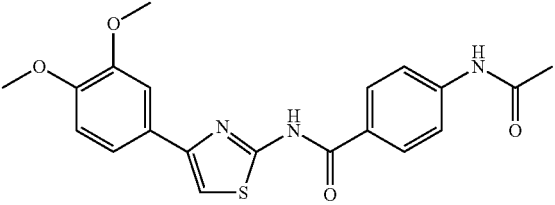 [SMILES: COc1ccc(-c2csc(NC(=O)c3ccc(NC(C)=O)cc3)n2)cc1OC] | 397.46 |
| 271 | 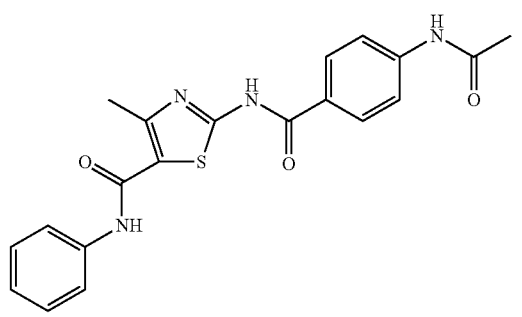 [SMILES: CC(=O)Nc1ccc(C(=O)Nc2nc(C)c(C(=O)Nc3ccccc3)s2)cc1] | 394.46 |
| 272 | 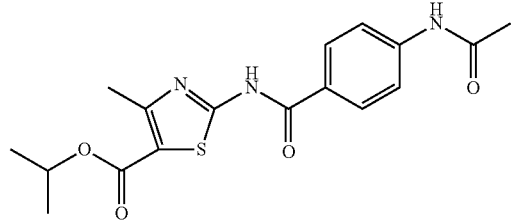 [SMILES: CC(=O)Nc1ccc(C(=O)Nc2nc(C)c(C(=O)OC(C)C)s2)cc1] | 361.42 |

TABLE 2-continued

Additional Representative Compounds

| ID | STRUCTURE | MW |
|---|---|---|
| 273 | 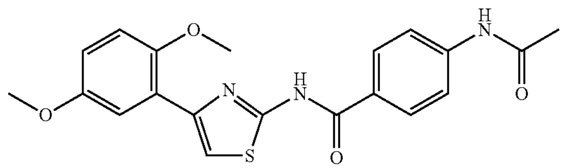 [SMILES: COc1ccc(OC)c(-c2csc(NC(=O)c3ccc(NC(C)=O)cc3)n2)c1] | 397.46 |
| 274 | 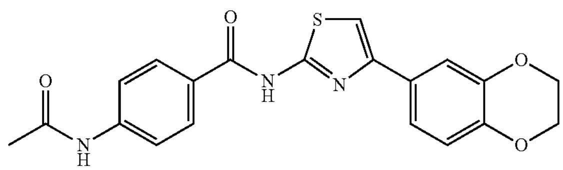 [SMILES: CC(=O)Nc1ccc(C(=O)Nc2nc(-c3ccc4c(c3)OCCO4)cs2)cc1] | 395.44 |
| 275 | 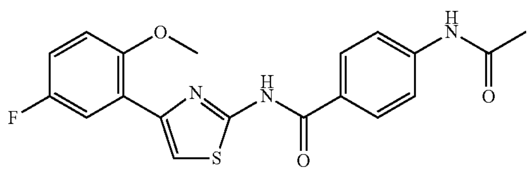 [SMILES: COc1ccc(F)cc1-c1csc(NC(=O)c2ccc(NC(C)=O)cc2)n1] | 385.42 |
| 276 | 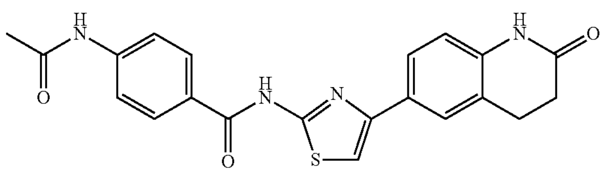 [SMILES: CC(=O)Nc1ccc(C(=O)Nc2nc(-c3ccc4c(c3)CCC(=O)N4)cs2)cc1] | 406.47 |
| 277 | 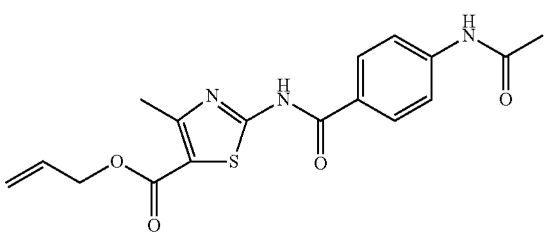 [SMILES: C=CCOC(=O)c1sc(NC(=O)c2ccc(NC(C)=O)cc2)nc1C] | 359.41 |
| 278 | 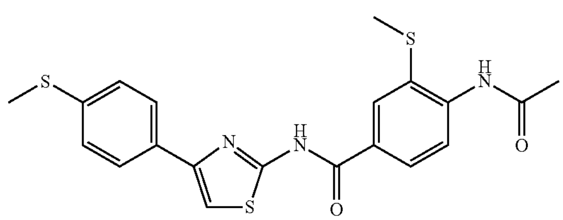 [SMILES: CSc1ccc(-c2csc(NC(=O)c3ccc(NC(C)=O)c(SC)c3)n2)cc1] | 429.59 |
| 279 | 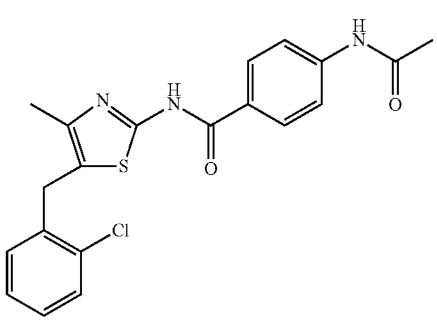 [SMILES: CC(=O)Nc1ccc(C(=O)Nc2nc(C)c(Cc3ccccc3Cl)s2)cc1] | 399.90 |

TABLE 2-continued

Additional Representative Compounds

| ID | STRUCTURE | MW |
|---|---|---|
| 280 | 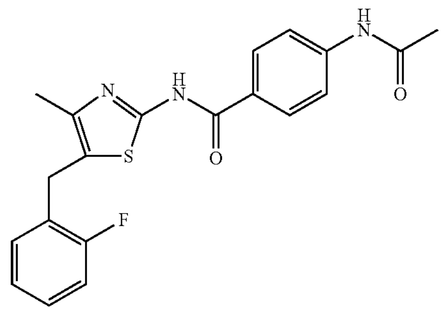 [SMILES: CC(=O)Nc1ccc(C(=O)Nc2nc(C)c(Cc3ccccc3F)s2)cc1] | 383.45 |
| 281 | 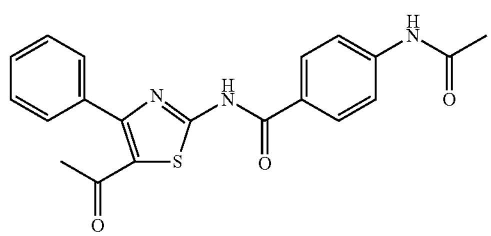 [SMILES: CC(=O)Nc1ccc(C(=O)Nc2nc(-c3ccccc3)c(C(C)=O)s2)cc1] | 379.44 |
| 282 | 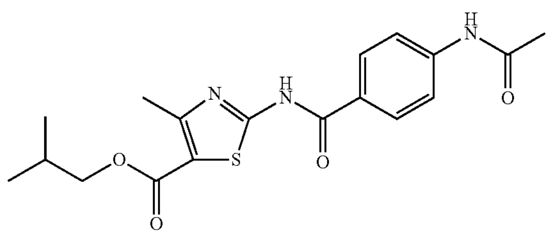 [SMILES: CC(=O)Nc1ccc(C(=O)Nc2nc(C)c(C(=O)OCC(C)C)s2)cc1] | 375.45 |
| 283 | 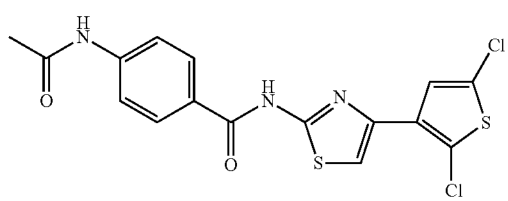 [SMILES: CC(=O)Nc1ccc(C(=O)Nc2nc(-c3cc(Cl)sc3Cl)cs2)cc1] | 412.32 |
| 284 | 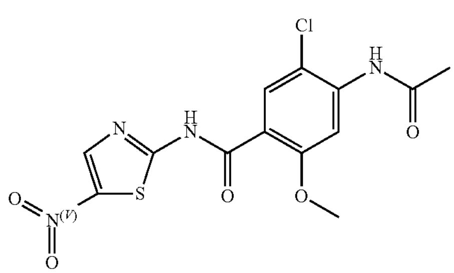 [SMILES: COc1cc(NC(C)=O)c(Cl)cc1C(=O)Nc1ncc([N+](=O)[O-])s1] | 370.77 |
| 285 | 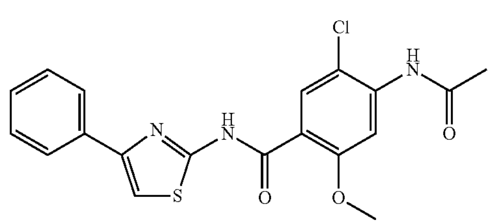 [SMILES: COc1cc(NC(C)=O)c(Cl)cc1C(=O)Nc1nc(-c2ccccc2)cs1] | 401.87 |

TABLE 2-continued

Additional Representative Compounds

| ID | STRUCTURE | MW |
|---|---|---|
| 286 | 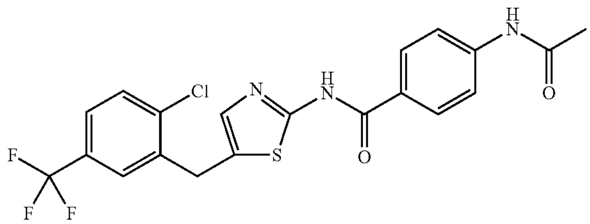 [SMILES: CC(=O)Nc1ccc(C(=O)Nc2ncc(Cc3cc(C(F)(F)F)ccc3Cl)s2)cc1] | 453.87 |
| 287 | 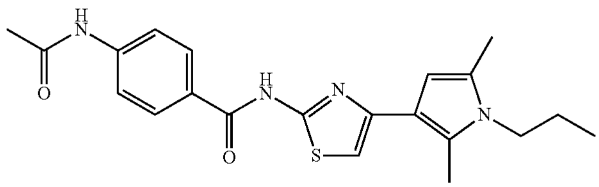 [SMILES: CCCn1c(C)cc(-c2csc(NC(=O)c3ccc(NC(C)=O)cc3)n2)c1C] | 396.52 |
| 288 | 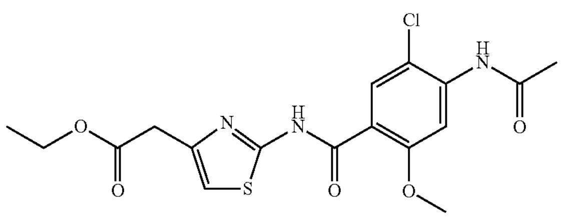 [SMILES: CCOC(=O)Cc1csc(NC(=O)c2cc(Cl)c(NC(C)=O)cc2OC)n1] | 411.87 |
| 289 | 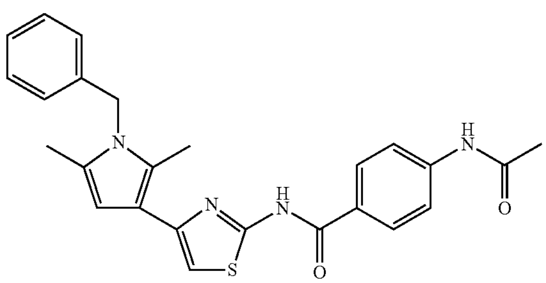 [SMILES: CC(=O)Nc1ccc(C(=O)Nc2nc(-c3cc(C)n(Cc4ccccc4)c3C)cs2)cc1] | 444.56 |
| 290 | 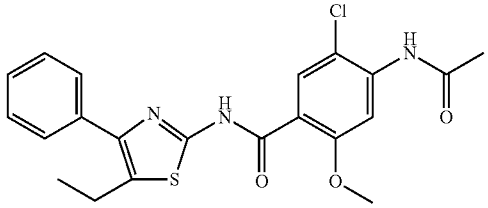 [SMILES: CCc1sc(NC(=O)c2cc(Cl)c(NC(C)=O)cc2OC)nc1-c1ccccc1] | 429.93 |
| 291 | 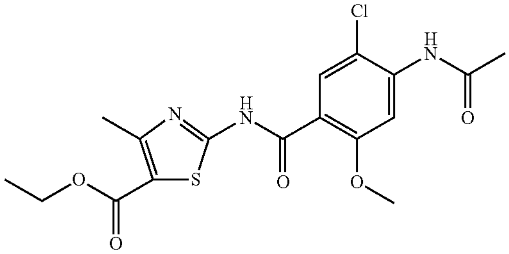 [SMILES: CCOC(=O)c1sc(NC(=O)c2cc(Cl)c(NC(C)=O)cc2OC)nc1C] | 411.87 |

$K_d$ Determinations

A number of representative heterocylic compounds of this invention were or can be tested for their inhibitory activity. The heterocylic compounds of the invention along with their available $K_d$ values, as determined using conventional methods to those skilled in the art, are listed below in Table 3.

TABLE 3

Exemplary Heterocylic compounds and available $K_d$ Values

| Compd # | Structure | MW (Calcd) | $K_d$ (nM) |
|---|---|---|---|
| CB-2 | 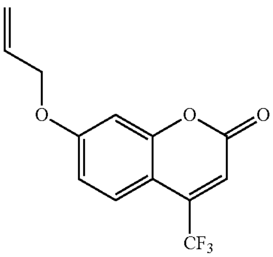 [SMILES: C=CCOc1ccc2c(C(F)(F)F)cc(=O)oc2c1] | 270.2 | 6.5 ± 1 |
| CB-3 | 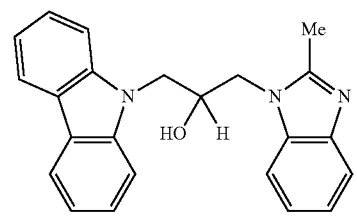 [SMILES: Cc1nc2ccccc2n1CC(O)Cn1c2ccccc2c2ccccc21] | 355.44 | 18 ± 1 |
| CB-4 | 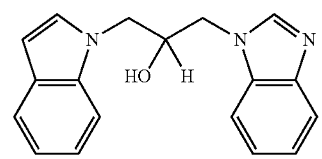 [SMILES: OC(Cn1ccc2ccccc21)Cn1cnc2ccccc21] | 291.36 | 2 ± 1 |
| CB-9 | 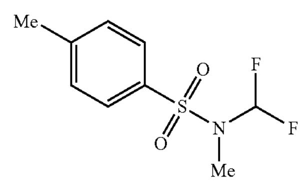 [SMILES: Cc1ccc(S(=O)(=O)N(C)C(F)F)cc1] | 235.25 | 17.3 ± 0.5 μM |
| CB-10 | 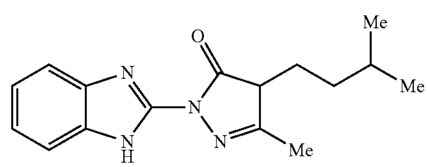 [SMILES: CC1=NN(c2nc3ccccc3[nH]2)C(=O)C1CCC(C)C] | 284.36 | 3.1 ± 0.3 |
| CB-11 | 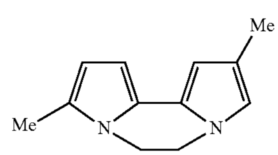 [SMILES: Cc1cc2n(c1)CCn1c(C)ccc1-2] | 186.26 | 1.2 ± 0.5 |
| CB-12 | 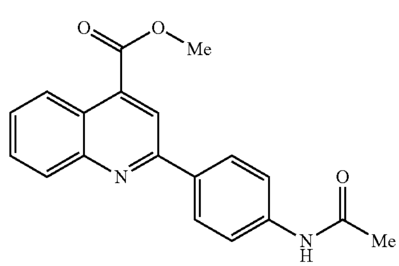 [SMILES: COC(=O)c1cc(-c2ccc(NC(C)=O)cc2)nc2ccccc12] | 320.35 | >100 μM |

TABLE 3-continued

Exemplary Heterocylic compounds and available $K_d$ Values

| Compd # | Structure | MW (Calcd) | $K_d$ (nM) |
|---|---|---|---|
| CD-4 | 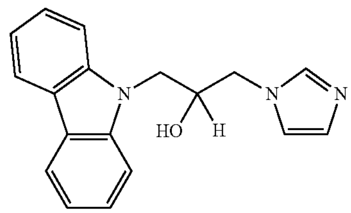 [SMILES: OC(Cn1ccnc1)Cn1c2ccccc2c2ccccc21] | 291.36 | 75 +/− 20 |
| CD-6 | 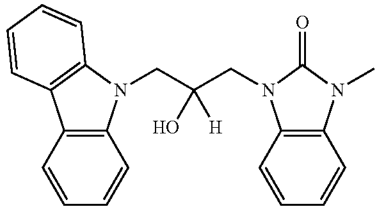 [SMILES: Cn1c(=O)n(CC(O)Cn2c3ccccc3c3ccccc32)c2ccccc21] | 371.44 | 4 +/− 2 |
| CD-7 | 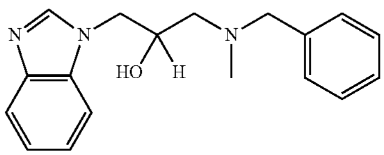 [SMILES: CN(Cc1ccccc1)CC(O)Cn1cnc2ccccc21] | 295.39 | 31% Inhibition @ 10 μM |
| CD-8 | 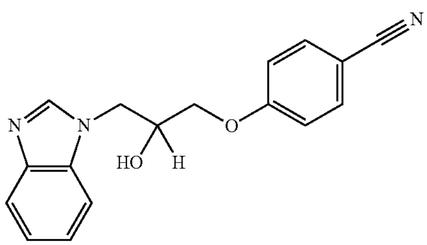 [SMILES: N#Cc1ccc(OCC(O)Cn2cnc3ccccc32)cc1] | 293.33 | 27% Inhibition @ 10 μM |
| CD-12 | 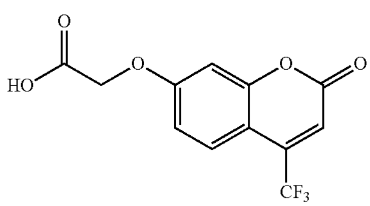 [SMILES: O=C(O)COc1ccc2c(C(F)(F)F)cc(=O)oc2c1] | 288.18 | 11% Inhibition @ 10 μM |
| CD-14 | 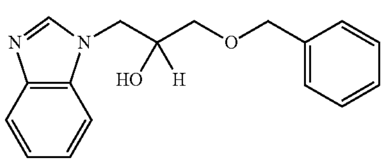 | 282.35 | 26% Inhibition @ 10 μM |
| CD-16 | 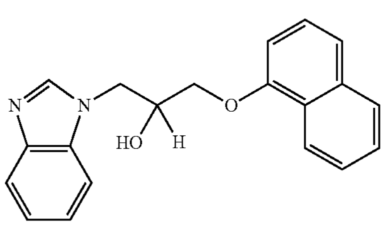 [SMILES: OC(COc1cccc2ccccc12)Cn1cnc2ccccc21] | 318.38 | 69% Inhibition @ 10 μM |

TABLE 3-continued

Exemplary Heterocylic compounds and available $K_d$ Values

| Compd # | Structure | MW (Calcd) | $K_d$ (nM) |
|---|---|---|---|
| CD-18 | 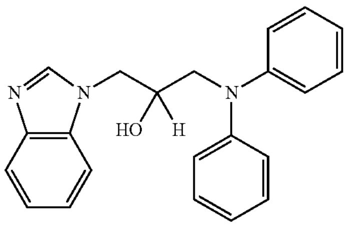 [SMILES: OC(CN(c1ccccc1)c1ccccc1)Cn1cnc2ccccc21] | 343.43 | 45% Inhibition @ 10 μM |
| CD-19 | 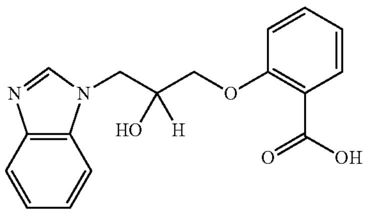 [SMILES: O=C(O)c1ccccc1OCC(O)Cn1cnc2ccccc21] | 312.33 | 24% Inhibition @ 10 μM |
| CD-20 | 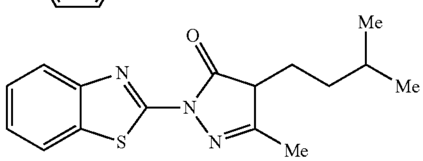 | 301.41 | 48% Inhibition @ 10 μM |
| CD-28 | 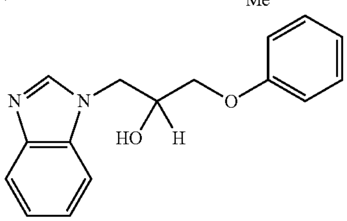 | 268.32 | 37% Inhibition @ 10 μM |
| CD-29 | 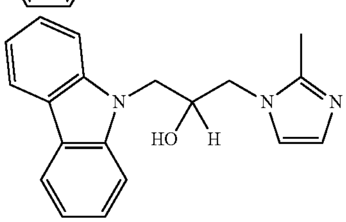 | 305.38 | 78 +/− 50 |

Compound#CB-4 was titrated into 100 nM solution of RAGE tail. Fluorescence quenching was used to determine binding. R2 quality factor of the fitting was 0.87 (FIG. 5).

Additional representative heterocyclic compounds according to formula B-I are listed below in Table 4.

TABLE 4

Additional Representative Compounds

| ID | STRUCTURE | MW |
|---|---|---|
| 101 | 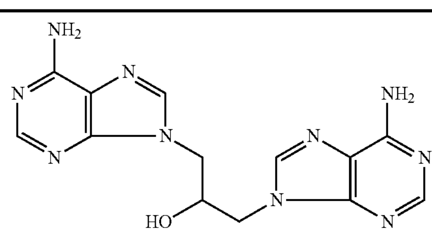 | 362.78 |
| 102 | | 291.36 |

TABLE 4-continued

Additional Representative Compounds

| ID | STRUCTURE | MW |
|---|---|---|
| 103 | 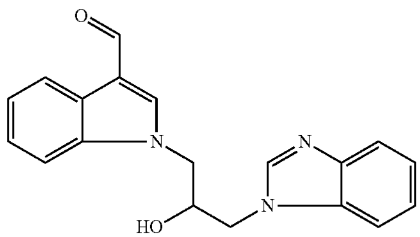 [SMILES: O=Cc1cn(CC(O)Cn2cnc3ccccc32)c2ccccc12] | 319.37 |
| 104 | 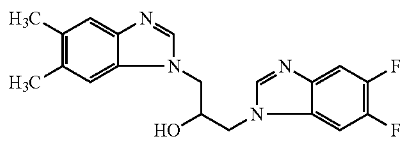 [SMILES: Cc1cc2ncn(CC(O)Cn3cnc4cc(F)c(F)cc43)c2cc1C] | 356.38 |
| 105 | 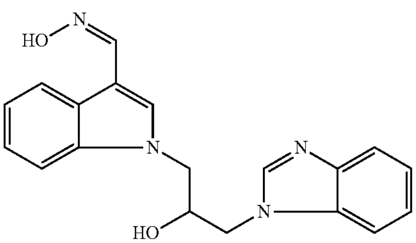 [SMILES: O/N=C\c1cn(CC(O)Cn2cnc3ccccc32)c2ccccc12] | 334.38 |
| 106 | 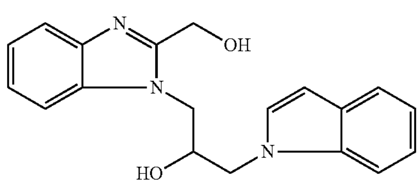 [SMILES: OCc1nc2ccccc2n1CC(O)Cn1ccc2ccccc21] | 321.38 |
| 107 | 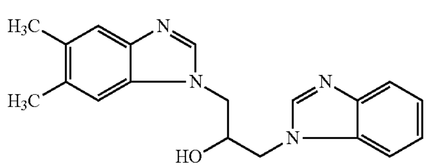 [SMILES: Cc1cc2ncn(CC(O)Cn3cnc4ccccc43)c2cc1C] | 320.40 |
| 108 | 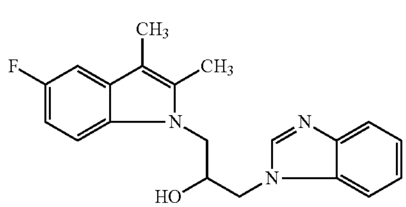 [SMILES: Cc1c(C)n(CC(O)Cn2cnc3ccccc32)c2ccc(F)cc12] | 337.40 |
| 109 | 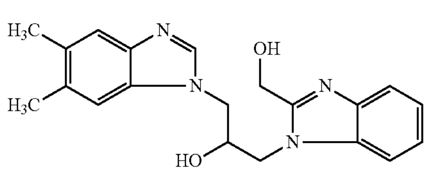 [SMILES: Cc1cc2ncn(CC(O)Cn3c(CO)nc4ccccc43)c2cc1C] | 350.42 |
| 110 | 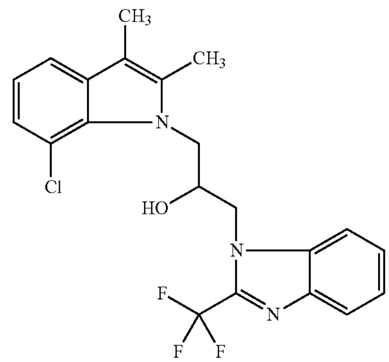 [SMILES: Cc1c(C)n(CC(O)Cn2c(C(F)(F)F)nc3ccccc32)c2c(Cl)cccc12] | 421.85 |
| 111 | 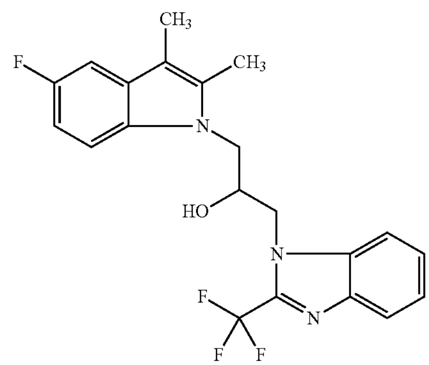 [SMILES: Cc1c(C)n(CC(O)Cn2c(C(F)(F)F)nc3ccccc32)c2ccc(F)cc12] | 405.40 |
| 112 | 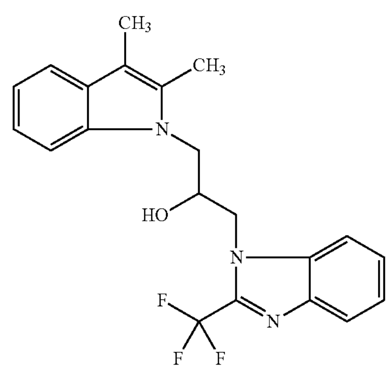 [SMILES: Cc1c(C)n(CC(O)Cn2c(C(F)(F)F)nc3ccccc32)c2ccccc12] | 387.41 |
| 113 | 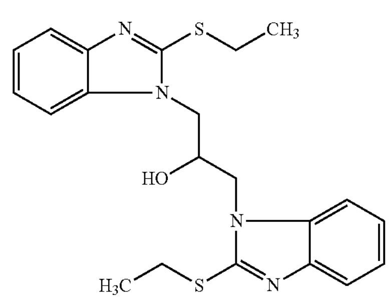 [SMILES: CCSc1nc2ccccc2n1CC(O)Cn1c(SCC)nc2ccccc21] | 412.58 |

TABLE 4-continued
Additional Representative Compounds
| ID | STRUCTURE | MW |
|----|-----------|-----|
| 114 | 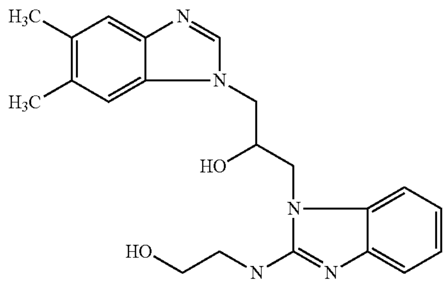 [SMILES: Cc1cc2ncn(CC(O)Cn3c(NCCO)nc4ccccc43)c2cc1C] | 379.47 |
| 115 | 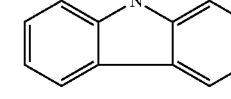 | 499.21 |
| 116 | 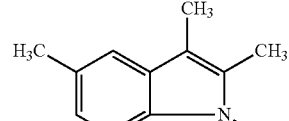 | 410.31 |
| 117 | 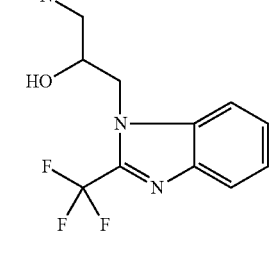 | 593.21 |
| 118 | 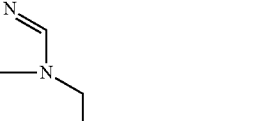 | 375.86 |
| 119 | 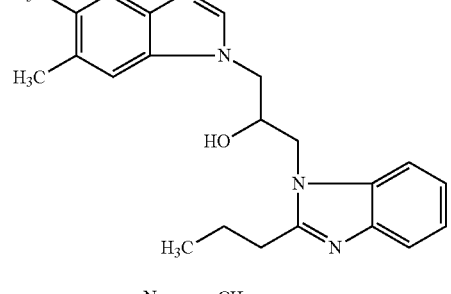 | 341.42 |
| 120 | 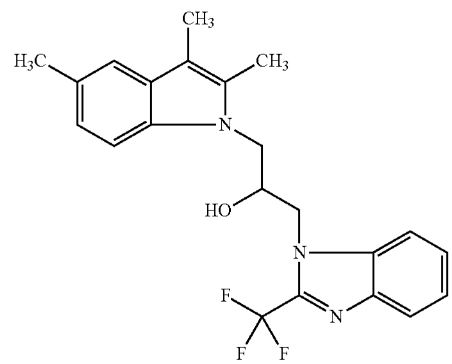 [SMILES: Cc1ccc2c(c1)c(C)c(C)n2CC(O)Cn1c(C(F)(F)F)nc2ccccc21] | 401.44 |
| 121 | 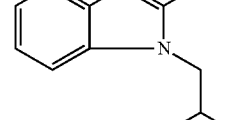 | 362.48 |
| 122 | 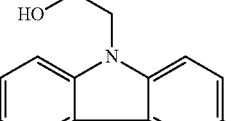 | 513.24 |
| 123 | 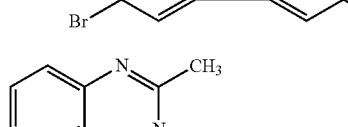 | 424.33 |

TABLE 4-continued

Additional Representative Compounds

| ID | STRUCTURE | MW |
|---|---|---|
| 124 | 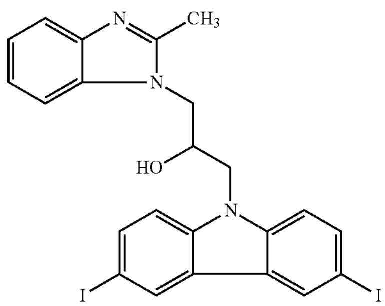 [SMILES: Cc1nc2ccccc2n1CC(O)Cn1c2ccc(I)cc2c2cc(I)ccc21] | 607.24 |
| 125 | 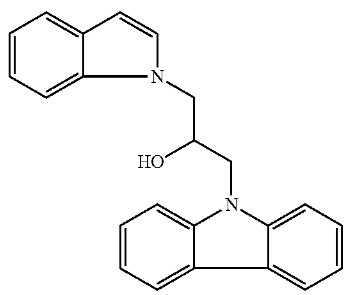 [SMILES: OC(Cn1ccc2ccccc21)Cn1c2ccccc2c2ccccc21] | 340.43 |
| 126 | 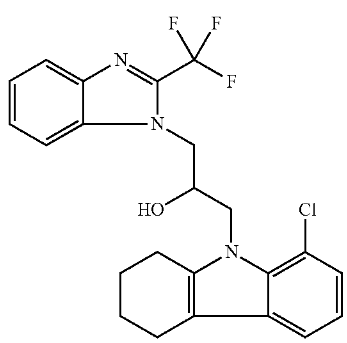 [SMILES: OC(Cn1c(C(F)(F)F)nc2ccccc21)Cn1c2c(c3cccc(Cl)c31)CCCC2] | 447.89 |
| 127 | 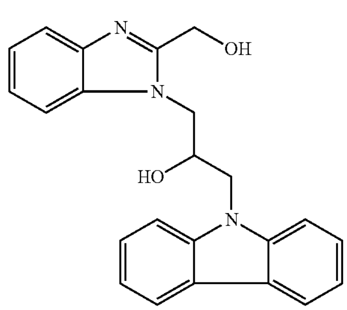 [SMILES: OCc1nc2ccccc2n1CC(O)Cn1c2ccccc2c2ccccc21] | 371.44 |
| 128 | 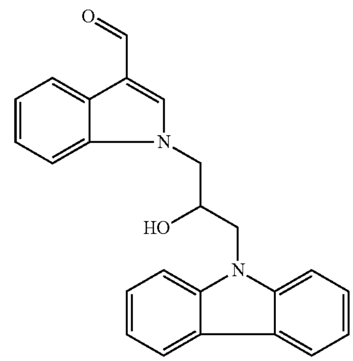 [SMILES: O=Cc1cn(CC(O)Cn2c3ccccc3c3ccccc32)c2ccccc12] | 368.44 |
| 129 | 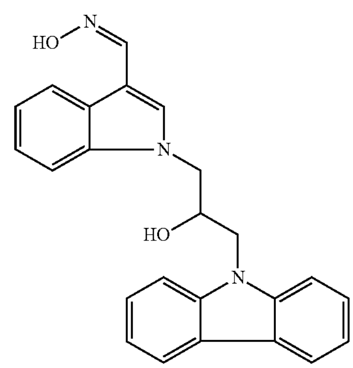 [SMILES: O/N=C\c1cn(CC(O)Cn2c3ccccc3c3ccccc32)c2ccccc12] | 383.45 |
| 130 | 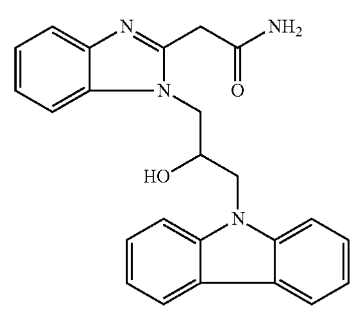 [SMILES: NC(=O)Cc1nc2ccccc2n1CC(O)Cn1c2ccccc2c2ccccc21] | 398.47 |
| 131 | 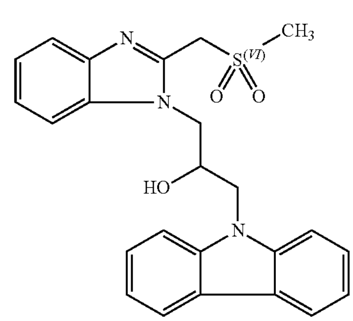 [SMILES: CS(=O)(=O)Cc1nc2ccccc2n1CC(O)Cn1c2ccccc2c2ccccc21] | 433.53 |

TABLE 4-continued
Additional Representative Compounds
| ID | STRUCTURE | MW |
|----|-----------|-----|
| 132 | 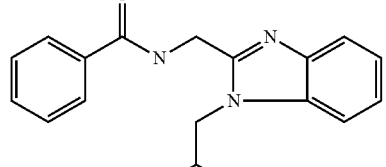 | 381.48 |
| 133 | 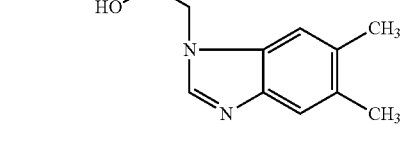 | 474.59 |
| 134 | 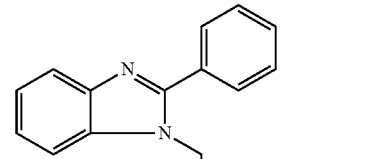 | 528.27 |
| 135 | 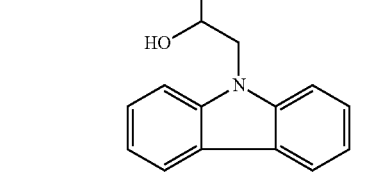 | 418.50 |
| 136 | 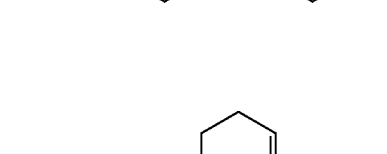 | 443.98 |
| 137 | 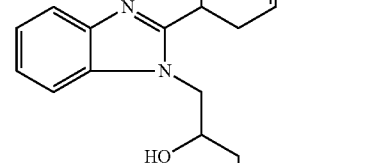 | 453.55 |
| 138 | 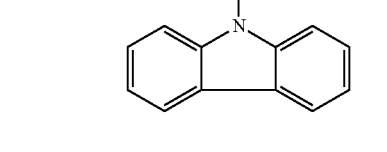 | 417.52 |
| 139 | 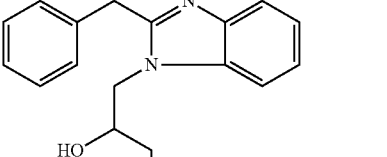 | 458.01 |
| 140 | 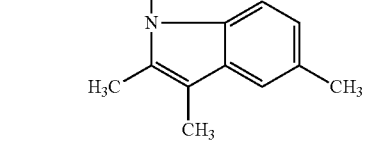 | 423.56 |

TABLE 4-continued

Additional Representative Compounds

| ID | STRUCTURE | MW |
|---|---|---|
| 141 | 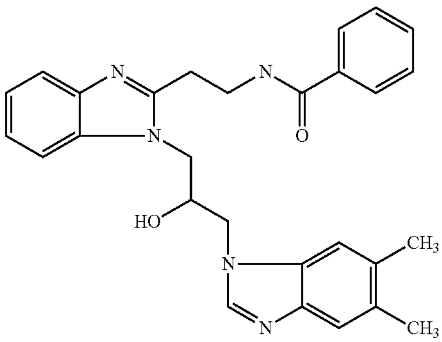 [SMILES: Cc1cc2ncn(CC(O)Cn3c(CCNC(=O)c4ccccc4)nc4ccccc43)c2cc1C] | 467.58 |
| 142 | 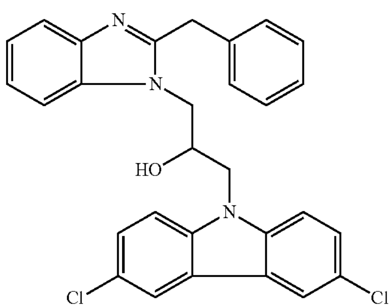 [SMILES: OC(Cn1c(Cc2ccccc2)nc2ccccc21)Cn1c2ccc(Cl)cc2c2cc(Cl)ccc21] | 500.43 |
| 143 | 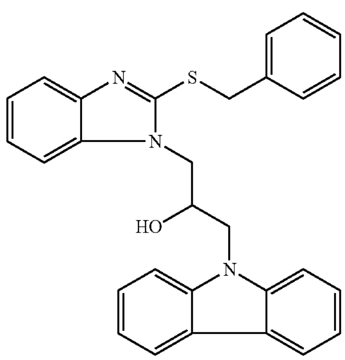 [SMILES: OC(Cn1c(SCc2ccccc2)nc2ccccc21)Cn1c2ccccc2c2ccccc21] | 463.61 |
| 144 | 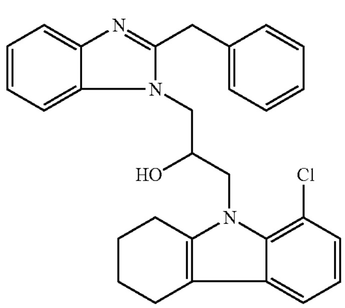 [SMILES: OC(Cn1c(Cc2ccccc2)nc2ccccc21)Cn1c2c(c3cccc(Cl)c31)CCCC2] | 470.02 |
| 145 | 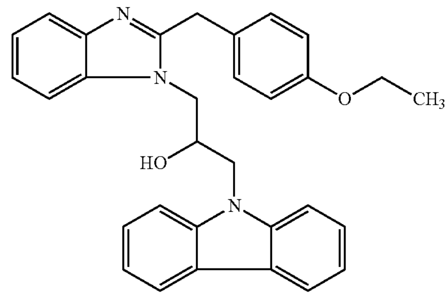 [SMILES: CCOc1ccc(Cc2nc3ccccc3n2CC(O)Cn2c3ccccc3c3ccccc32)cc1] | 475.60 |
| 146 | 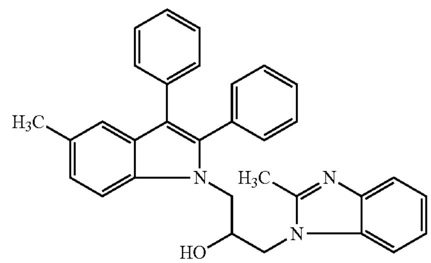 [SMILES: Cc1ccc2c(c1)c(-c1ccccc1)c(-c1ccccc1)n2CC(O)Cn1c(C)nc2ccccc21] | 508.07 |
| 147 | 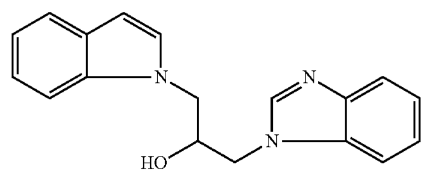 [SMILES: OC(Cn1ccc2ccccc21)Cn1cnc2ccccc21] | 291.36 |
| 148 | 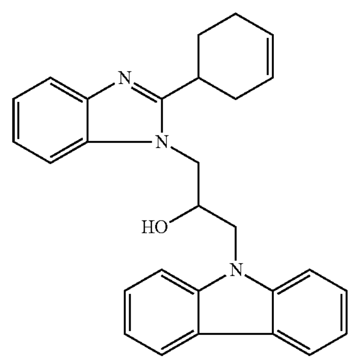 [SMILES: OC(Cn1c(C2CC=CCC2)nc2ccccc21)Cn1c2ccccc2c2ccccc21] | 421.55 |
| 149 | 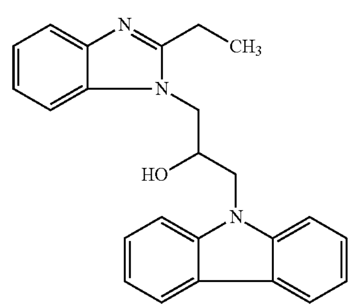 | 369.47 |

TABLE 4-continued

Additional Representative Compounds

| ID | STRUCTURE | MW |
|----|-----------|-----|
| 150 | 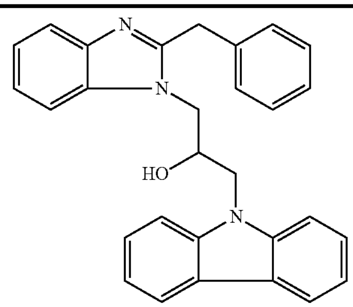 | 431.54 |
| 151 | 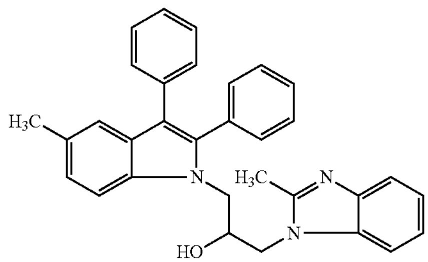 [SMILES: Cc1ccc2c(c1)c(-c1ccccc1)c(-c1ccccc1)n2CC(O)Cn1c(C)nc2ccccc21] | 471.61 |
| 152 | 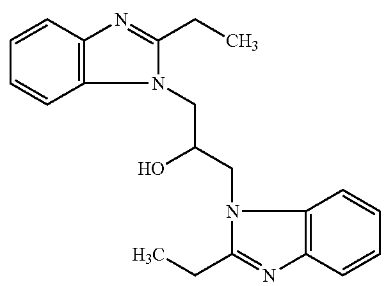 [SMILES: CCc1nc2ccccc2n1CC(O)Cn1c(CC)nc2ccccc21] | 348.45 |

Example 2

Representative Method and Protocol for Secondary Screening

Figure 3:
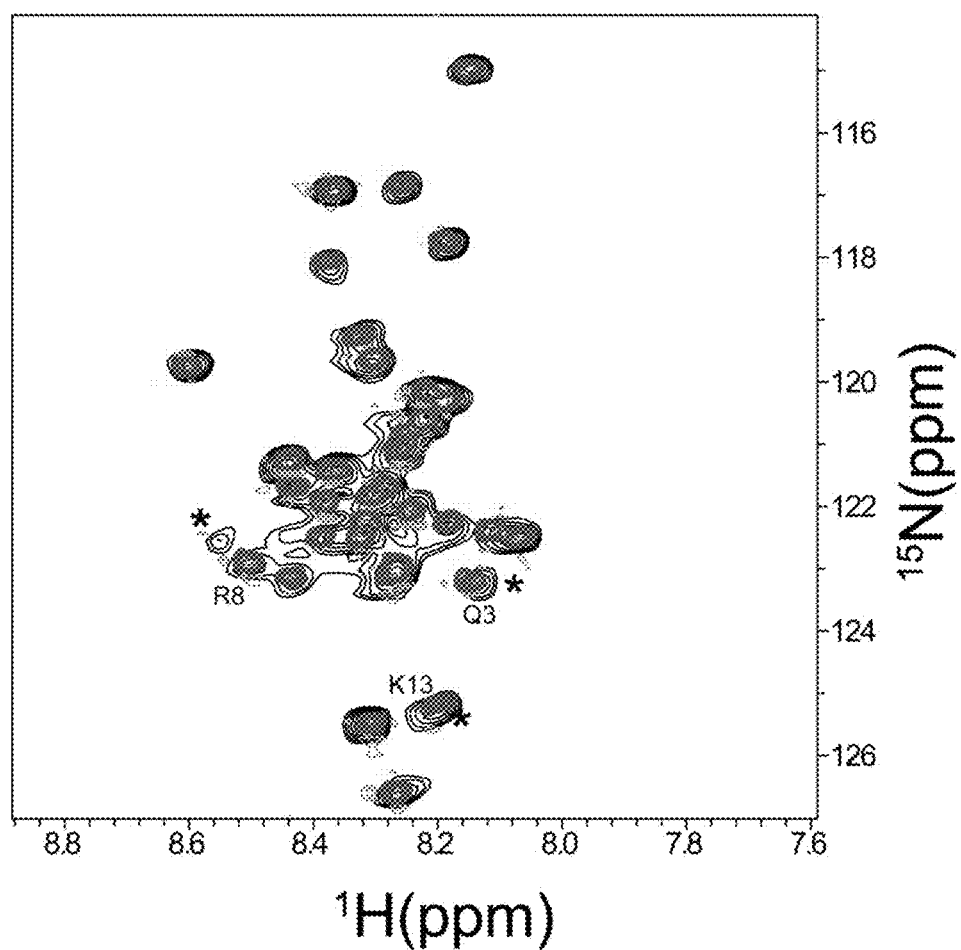
FIG. 3 shows NMR spectrum of RAGE tail in complex with compound CB-6. Red—overlay of $^{15}$N-HSQC spectra of free (red). Black—CB-6 bound [U—$^{15}$N] RAGE tail. Asteric—New peaks or peaks that undergo significant shifts or peak broadening (labeled by corresponding amino acid residue numbers).

A complex of RAGE tail and a representative compound, CB-6, was prepared by adding 10 μM of CB-6 to a solution of 10 μM of [U—$^{15}$N] RAGE tail in 10 mM potassium phosphate buffer, pH 6.0. The NMR spectrum of the complex was acquired following the method described herein (FIG. 3). The FIG. 3 shows overlay of $^{15}$N-HSQC spectra of free (red) and CB-6 bound [U—$^{15}$N] RAGE tail (black). New peaks or peaks that undergo significant shifts are indicated by asteric and labeled by corresponding amino acid residue numbers.

Figure 6:
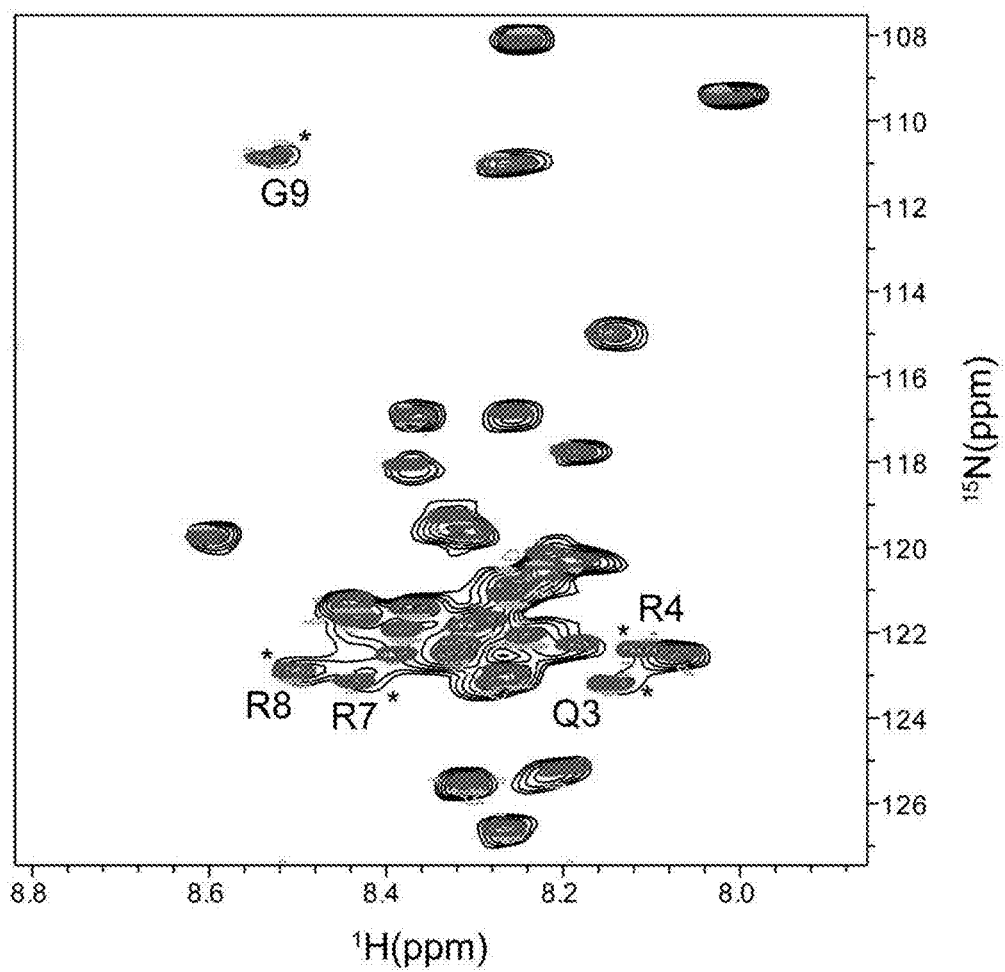
FIG. 6 shows the NMR spectrum of RAGE tail in complex with compound CB-3. Red—overlay of $^{15}$N-HSQC spectra of free (red). Black—CB-3 bound [U—$^{15}$N] RAGE tail. Asteric—New peaks or peaks that undergo significant shifts or peak broadening (labeled by corresponding amino acid residue numbers).

A complex of RAGE tail and a representative compound, CB-3, was prepared by adding 10 μM of CB-3 to a solution of 10 μM of [U—$^{15}$N] RAGE tail in 10 mM potassium phosphate buffer, pH 6.0. The NMR spectrum of the complex was acquired following the method described herein (FIG. 6). The FIG. 6 shows overlay of $^{15}$N-HSQC spectra of free (red) and CB-3 bound [U—$^{15}$N] RAGE tail (black). New peaks or peaks that undergo significant shifts or peak broadening are indicated by asteric and labeled by corresponding amino acid residue numbers.

FIG. 7 presents a table that lists the dissociation constants determined for CB-1 to CB-14 binding to the RAGE tail.

Example 3

Representative In Vitro Assays

Methods and Materials

Effects of CB-1 to CB-14 on Murine Smooth Muscle Cell Migration. Primary murine aortic smooth muscles retrieved from wild type C57BL/6 mice were grown to 90% confluency in medium containing 10% fetal bovine serum. Cells were serum starved for 16 hrs during which time fetal bovine serum was replaced with 0.1% bovine serum albumin. Following this period of serum starvation, cells were pre-treated for 1.5 hours with the indicated Chembridge library hit denoted #1-14 at a concentration of 1 μM. At the end of that time, compounds were removed and cell monolayers were vertically scratched with a pipet tip to create a "wound" and then RAGE ligand carboxy methyl lysine human serum albumin (CML AGE), 100 μg/ml, was added for 7 hrs. Photographs of the monolayer were taken at time 0 (time of scratch/CML AGE) and at 7 hrs. The ingrowth of the cells was then noted and % area ingrowth was calculated comparing ingrowth at baseline to that at 7 hrs. N-triplicate experiments. * indicates p<0.05

Effects of CB-1 to CB-14 on Human Smooth Muscle Cell Migration. Primary human aortic smooth muscles were purchased from Lonza and were grown to 90% confluency in medium containing 10% fetal bovine serum. Cells were serum starved for 16 hrs during which time fetal bovine serum was replaced with 0.1% bovine serum albumin. Following this period of serum starvation, cells were pre-treated for 1.5 hours with the indicated Chembridge library hit denoted #1-14 at a concentration of 1 μM. At the end of that time, compounds were removed and cell monolayers were vertically scratched with a pipet tip to create a "wound" and then RAGE ligand carboxy methyl lysine human serum albumin (CML AGE), 100 μg/ml, was added for 7 hrs. Photographs of the monolayer were taken at time 0 (time of scratch/CML AGE) and at 7 hrs. The ingrowth of the cells was then noted and % area ingrowth was calculated comparing ingrowth at baseline to that at 7 hrs. N=triplicate experiments. * indicates p<0.05 (FIG. 8)

Figure 8:
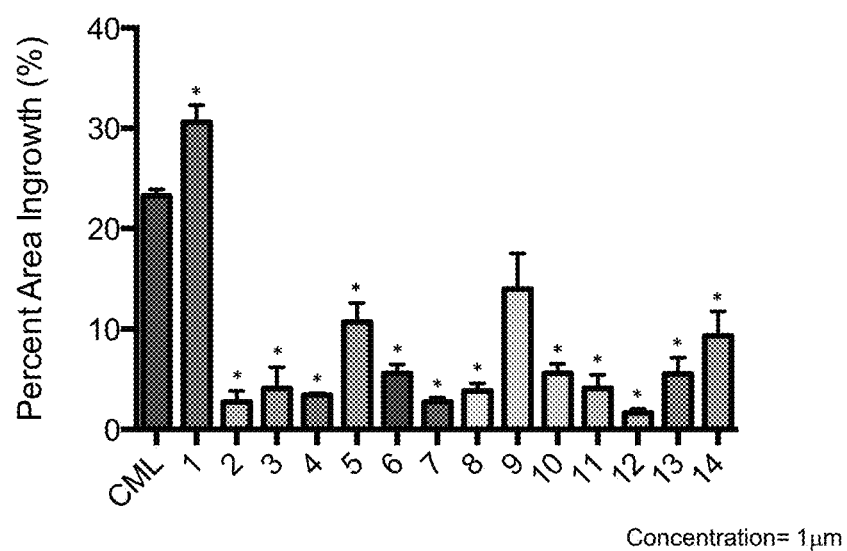
FIG. 8 shows the effects of CB-1 to CB-14 on murine smooth muscle cell migration.

FIG. 8 shows that CB-2, CB-3, CB-4, CB-5, CB-6, CB-7, CB-8, CB-9, CB-10, CB-11, CB-12, CB-13, and CB-14 prevent RAGE ligand CML AGE-mediated ingrowth (migration) of primary murine aortic smooth muscle cells. In contrast, CB-1 had no inhibitory effect. Rather, significantly higher ingrowth in response to CML AGE was noted in the presence of CB-1. These results indicate that CB compounds 2-14 suppress RAGE ligand-mediated migration/ingrowth of primary murine aortic smooth muscle cells.

Figure 9:
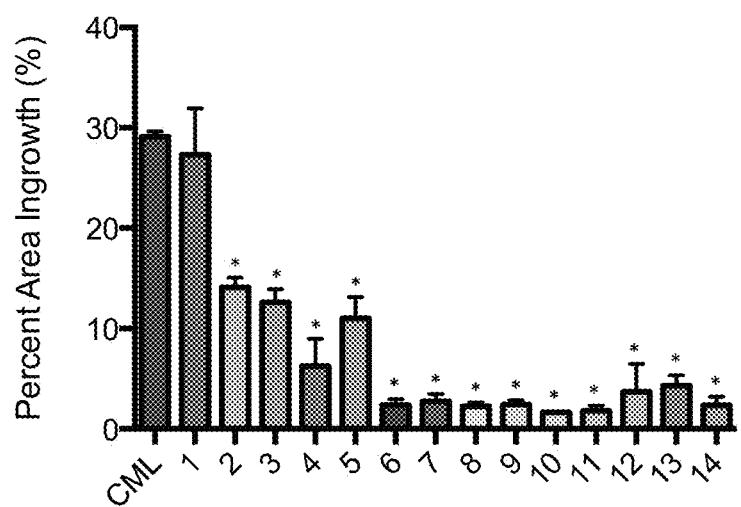
FIG. 9 shows the effects of CB-1 to CB-14 on human smooth muscle cell migration.

FIG. 9 shows that CB-2, CB-3, CB-4, CB-5, CB-6, CB-7, CB-8, CB-9, CB-10, CB-11, CB-12, CB-13, and CB-14 prevent RAGE ligand CML AGE-mediated ingrowth (migration) of primary human aortic smooth muscle cells. In contrast, CB-1 had no inhibitory effect on RAGE ligand-mediated migration/ingrowth of these cells. These results indicate that CB compounds 2-14 suppress RAGE ligand-mediated migration/ingrowth of primary murine aortic smooth muscle cells.

Example 4

Representative In Vivo Assays

Methods and Materials

Effects of CB Compounds 1-14 on an in vivo model of delayed type hypersensitivity (DTH). Female CF-1 mice were purchased from the Jackson Laboratories (Bar Harbor Me.) and after a period of at least 3 days acclimation in the animal facility, mice were sensitized over the left inguinal lymph node with an emulsion (0.1 ml) containing methylated bovine serum albumin (mBSA, Sigma, 25 mg/ml), NaCl (0.9%), dextran 5-40×10$^6$ MW; 50 mg/ml (Sigma), and Freunds' incomplete adjuvant (50%). On day 19 and 20 after sensitization, mice received an intraperitoneal dose of one of CB compounds 1-14 at 5 mg/kg/body weight mouse for a total of four doses. Control animals received equal volumes of compound diluent, DMSO. Immediately following the final compound injection (4$^{th}$ dose), mBSA (0.4 mg/ml; 0.050 ml) was injected into the left plantar hind paw. The paw was scored 16 hrs later by 2 investigators naive to the experimental condition and according to the following criteria: 1=absence of any inflammation; 2=slight rubor and edema; 3=moderate rubor and edema with skin wrinkles; 4=severe rubor and edema without skin wrinkles and 5=severe rubor and edema with toe spreading. See also Hofmann et al. (1999, Cell 97:889-901), the entire content of which is incorporated herein in its entirety. In these experiments, n=5 mice/group.

As shown in FIG. 10 and in Table 5 (below), in a murine model of delayed type hypersensitivity in which the pro-inflammatory ligands of RAGE accumulate, CB compounds denoted as CB-3 and CB-12 impact a statistically significant reduction in inflammation score in the paw after injection of methylated BSA compared to mice treated with vehicle, DMSO, and equal amounts of methylated BSA.

TABLE 5

| Compound # | Inflammation Score Compound/Vehicle ± SEM | P Value Vs. Vehicle |
|---|---|---|
| CB-1 | 3.4 ± 0.55/3.4 ± 0.55 | Not Significant |
| CB-2 | 3.2 ± 0.45/3.4 ± 0.55 | Not Significant |
| CB-3 | 2.2 ± 0.45/3.4 ± 0.55 | p = 0.0053 |
| CB-4 | 3.0 ± 0.71/3.4 ± 0.55 | Not Significant |
| CB-5 | 3.6 ± 0.55/3.4 ± 0.55 | Not Significant |
| CB-6 | 3.0 ± 0.71/3.6 ± 0.55 | Not Significant |
| CB-7 | 3.4 ± 0.55/3.6 ± 0.55 | Not Significant |
| CB-8 | 3.4 ± 0.55/3.6 ± 0.55 | Not Significant |
| CB-9 | 3.6 ± 0.55/3.6 ± 0.55 | Not Significant |
| CB-10 | 3.2 ± 0.84/3.6 ± 0.55 | Not Significant |
| CB-11 | 3.2 ± 0.45/3.4 ± 0.55 | Not Significant |
| CB-12 | 2.4 ± 0.55/3.4 ± 0.55 | p = 0.0203 |
| CB-13 | 3.4 ± 0.55/3.4 ± 0.55 | Not Significant |
| CB-14 | 3.2 ± 0.45/3.4 ± 0.55 | Not Significant |

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using Open Eye Software's Lexichem naming tool, Symyx Renassance Software's Reaction Planner or MDL's ISIS Draw Autonom Software tool and not verified. Preferably, in the event of inconsistency, the depicted structure governs.

REFERENCES

1) International Diabetes Federation. (2012) IDF Diabetes Atlas (5th edn), International Diabetes Federation; Brussels, Belgium
2) Patterson, C. C., et al. (2012) Trends in childhood type 1 diabetes incidence in Europe during 1989-2008: evidence of non-uniformity over time in rates of increase. *Diabetologia* 55, 2142-2147
3) Lipman, T. H., et al. (2013) Increasing Incidence of Type 1 Diabetes in Youth: Twenty years of the Philadelphia Pediatric Diabetes Registry. *Diabetes Care* 36, 1597-1603
4) Nathan D M, et al. (2009) Medical management of hyperglycemia in type 2 diabetes: a consensus algorithm for the initiation and adjustment of therapy: a consensus statement of the American Diabetes Association and the European Association for the Study of Diabetes. *Diabetes Care* 3: 193-203.
5) (UKPDS), U.P.D.S.G. (1998) Intensive blood-glucose control with sulphonylureas or insulin compared with conventional treatment and risk of complications in patients with type 2 diabetes (UKPDS 33). UK Prospective Diabetes Study (UKPDS) Group. *Lancet*, pp. 837-853
6) The Diabetes Control and Complications Trial Research Group (1993) The effect of intensive treatment of diabetes on the development and progression of long-term complications in insulin-dependent diabetes mellitus. The Diabetes Control and Complications Trial Research Group. *New Engl J Med*, pp. 977-986
7) Frye, E. B., et al. (1998) Role of the Maillard reaction in aging of tissue proteins. Advanced glycation end product-dependent increase in imidazolium cross-links in human lens proteins. *J Biol Chem* 273, 18714-18719
8) Yan, S. F., et al. (2009) Tempering the wrath of RAGE: an emerging therapeutic strategy against diabetic complications, neurodegeneration, and inflammation. *Ann Med* 41, 408-422
9) Yan, S. F., et al. (2010) The RAGE axis: a fundamental mechanism signaling danger to the vulnerable vasculature. *Circ Res* 106, 842-853
10) Hudson, B. I., et al. (2008) Interaction of the RAGE cytoplasmic domain with diaphanous-1 is required for ligand-stimulated cellular migration through activation of Rac1 and Cdc42. *J Biol Chem* 283, 34457-34468
11) Rai, V., et al. (2012) Signal transduction in receptor for advanced glycation end products (RAGE): solution structure of C-terminal rage (ctRAGE) and its binding to mDia1. *J Biol Chem* 287, 5133-5144
12) Xu, Y., et al. (2010) Advanced glycation end product (AGE)-receptor for AGE (RAGE) signaling and up-regulation of Egr-1 in hypoxic macrophages. *J Biol Chem* 285, 23233-23240
13) Toure, F., et al (2012) Formin mDia1 mediates vascular remodeling via integration of oxidative and signal transduction pathways. *Circ Res* 110, 1279-1293.

What is claimed is:

1. A method for treating or ameliorating in a mammal a disease or condition that is causally related to RAGE activity in vivo, which comprises administering to the mammal an effective disease-treating or condition-treating amount of a compound according to formula B-I':

109

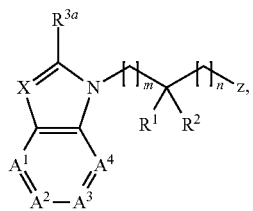

wherein
each $A^1$, $A^2$, $A^3$, and $A^4$ is independently $CR^4$ or N; provided that only 1 or 2 of $A^1$, $A^2$, $A^3$, and $A^4$ are N at any one time;

Z is substituted amino, substituted hydroxyl, substituted or unsubstituted aryl, or substituted or unsubstituted heteroaryl;

X is $CR^{5a}$ or N;

$R^1$ is hydroxy, substituted hydroxyl, amino, or substituted amino;

$R^2$ is H, alkyl or aryl;

$R^{3a}$ is H, substituted or unsubstituted alkyl, substituted or unsubstituted cycloalkyl, substituted or unsubstituted aryl, halo, or cyano;

each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;

$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring;

and each of the subscript m and n is independently 1, 2, or 3;

or a pharmaceutically acceptable salt, solvate or prodrug thereof;

or stereoisomers, isotopic variants and tautomers thereof;

wherein the disease or condition is selected from diabetes and its complications, atherosclerosis, peripheral vascular disease and associated complications, cardiovascular disease nephropathy, retinopathy, cardio- and cerebrovascular ischemia/reperfusion injury, heart attack, myocardial infarction, ischemic cardiomyopathy, cancer, tumor invasion and metastases, acute and chronic inflammation, arthritis, allergy asthma, obesity, pollution-associated tissue or organ damage, infection, sepsis, pneumonia, liver injury/damage, amyloidoses, skin disorders, colitis, lupus, and impaired wound healing.

2. The method according to claim 1, wherein Z is

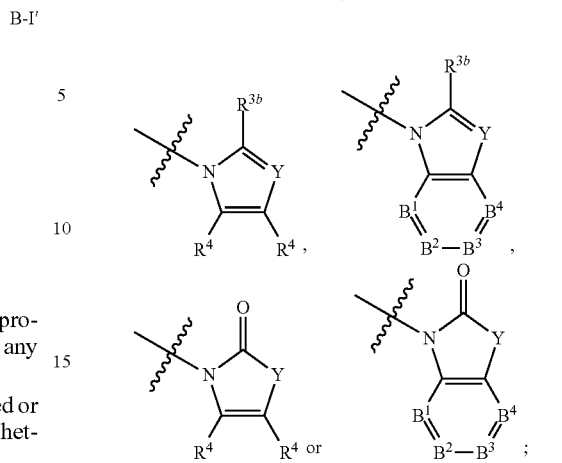

wherein $B^1$, $B^2$, $B^3$, and $B^4$ is independently $CR^4$ or N; Y is, $CR^{5b}$ or $NR^{5a}$; $R^{3b}$ is $R^{3a}$; and $R^4$ are as in claim 1; and $R^{5b}$ is independently H, substituted or unsubstituted alkyl, substituted or unsubstituted cycloalkyl, substituted or unsubstituted aryl, halo, or cyano; or $R^{5b}$ and $R^{3b}$ may join together to form a substituted or unsubstituted carbocyclic or heterocyclic ring.

3. The method according to claim 1, wherein the compound is according to formula B-I:

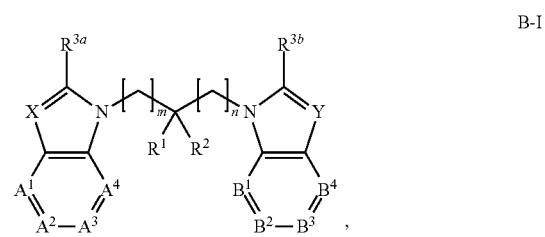

B-I wherein
each $A^1$, $A^2$, $A^3$, $A^4$, $B^1$, $B^2$, $B^3$, and $B^4$ is independently $CR^4$ or N; provided that only 1 or 2 of $A^1$, $A^2$, $A^3$, and $A^4$ are N, and only 1 or 2 of $B^1$, $B^2$, $B^3$, and $B^4$ are N at any one time;

X is $CR^{5a}$ or N; X is $CR^{5b}$ or N;

$R^1$ is hydroxy, substituted hydroxyl, amino, or substituted amino;

$R^2$ is H, alkyl or aryl;

each $R^{3a}$ and $R^{3b}$ is independently H, substituted or unsubstituted alkyl, substituted or unsubstituted cycloalkyl, substituted or unsubstituted aryl, halo, or cyano;

each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;

$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring;

$R^{5b}$ is independently H, substituted or unsubstituted alkyl, substituted or unsubstituted cycloalkyl, substituted or unsubstituted aryl, halo, or cyano; or $R^{5b}$ and $R^{3b}$ may join together to form a substituted or unsubstituted carbocyclic or heterocyclic ring;

and each of the subscript m and n is independently 1, 2, or 3;

or a pharmaceutically acceptable salt, solvate or prodrug thereof;

or stereoisomers, isotopic variants and tautomers thereof.

4. The method according to claim 1, wherein the compound is according to formula B-VII:

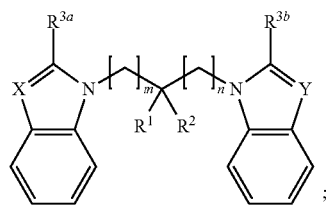

B-VII and wherein X, Y, $R^1$, $R^2$, $R^{3a}$, $R^{3b}$, m, and n are as in claim 3;

or a pharmaceutically acceptable salt, solvate or prodrug thereof;

or stereoisomers, isotopic variants and tautomers thereof.

5. The method according to claim 1, wherein the compound is according to formula B-VIIIa, B-VIIIb, B-VIIIc, or B-VIIId:

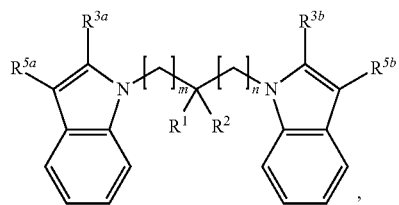

B-VIIIa

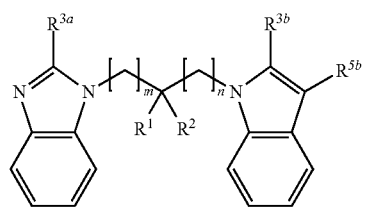

B-VIIIb

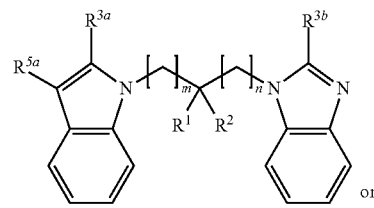

B-VIIIc

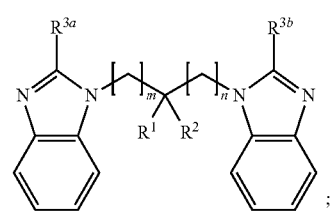

B-VIIId and wherein $R^1$, $R^2$, $R^{3a}$, $R^{3b}$, $R^{5a}$, $R^{5b}$, m, and n are as in claim 1;

or a pharmaceutically acceptable salt, solvate or prodrug thereof;

or stereoisomers, isotopic variants and tautomers thereof.

6. The method according to claim 1, wherein the compound is according to formula B-IXa, B-IXb, or B-IXc :

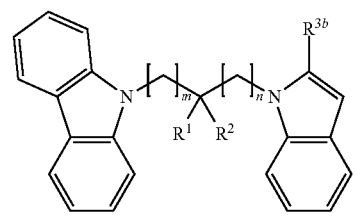

B-IXa

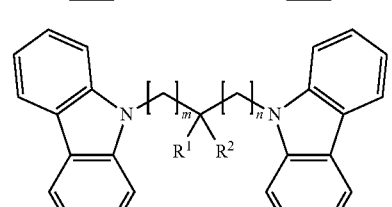

B-IXb

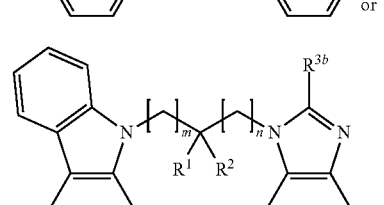

B-IXc and wherein $R^1$, $R^2$, $R^{3b}$, m, and n are as in claim 3;

or a pharmaceutically acceptable salt, solvate or prodrug thereof;

or stereoisomers, isotopic variants and tautomers thereof.

7. The method according to claim 1, wherein $R^1$ is OH, alkoxy, or acyloxy.

8. The method according claim 1, wherein $R^2$ is substituted or unsubstituted alkyl.

9. The method according to claim 1, wherein $R^2$ is substituted or unsubstituted aryl.

10. The method according to claim 1, wherein m is 1; and n is 1.

11. The method according to claim 1, wherein the compound is according to formula B-Xa, B-Xb, B-Xc, or B-Xd:

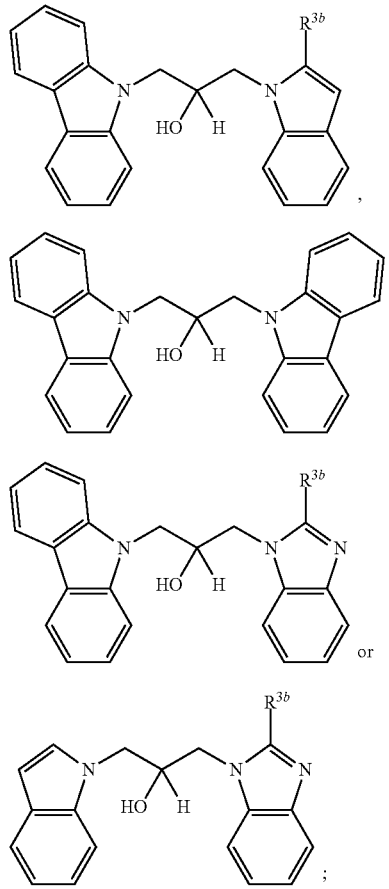

and wherein $R^{3b}$ is as in claim 3;

or a pharmaceutically acceptable salt, solvate or prodrug thereof;

or stereoisomers, isotopic variants and tautomers thereof.

12. The method according to claim 1, wherein $R^{3b}$ is independently H, substituted or unsubstituted alkyl, substituted or unsubstituted cycloalkyl, substituted or unsubstituted aryl, halo, or cyano.

13. The method according to claim 1, wherein the compound is according to formula B-XIa, B-XIb, B-XIc, B-XId, B-XIe, B-XIf, B-XIg, or B-XIh:

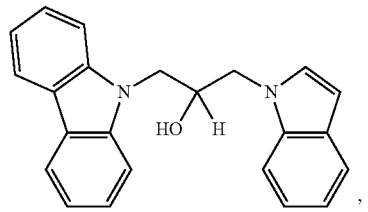

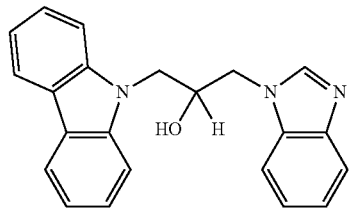

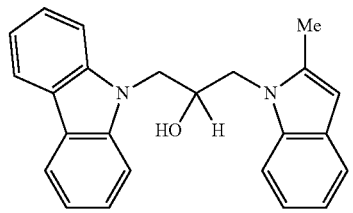

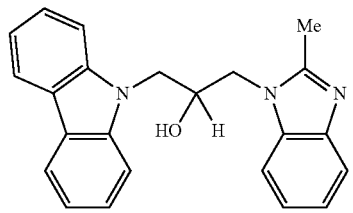

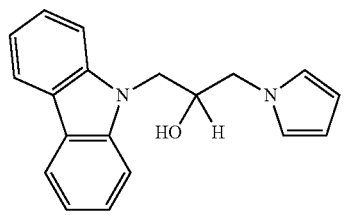

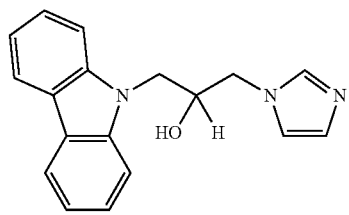

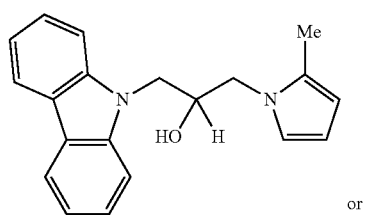

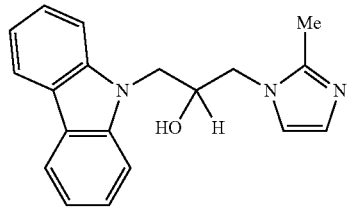

or a pharmaceutically acceptable salt, solvate or prodrug thereof;

or stereoisomers, isotopic variants and tautomers thereof.

14. The method according to claim 1, wherein the compound is according to formula B-XIIa, B-XIIb, B-XIIc, B-XIId, B-XIIe, or B-XIIf:

[Structure B-XIIa: carbazole-CH2-CH(OH)-CH2-N(benzimidazole with CF3)]

[Structure B-XIIb: carbazole-CH2-CH(OH)-CH2-N(benzimidazole with CF3)]

[Structure B-XIIc: carbazole-CH2-CH(OH)-CH2-N(benzimidazole with CHF2)]

[Structure B-XIId: carbazole-CH2-CH(OH)-CH2-N(benzimidazole with CHF2)]

[Structure B-XIIe: carbazole-CH2-CH(OH)-CH2-N(oxindole)]

[Structure B-XIIf: carbazole-CH2-CH(OH)-CH2-N(N-methyl-benzimidazolone)]

or a pharmaceutically acceptable salt, solvate or prodrug thereof;

or stereoisomers, isotopic variants and tautomers thereof.

15. The method according to claim 1, wherein the compound is according to formula B-XIIIa, B-XIIIb, B-XIIIc, or B-XIIId:

[Structure B-XIIIa: indole-CH2-CH(OH)-CH2-N(benzimidazole)]

[Structure B-XIIIb: indole-CH2-CH(OH)-CH2-N(benzimidazole with Me)]

[Structure B-XIIIc: indole-CH2-CH(OH)-CH2-N(benzimidazole with CF3)]

[Structure B-XIIId: indole-CH2-CH(OH)-CH2-N(benzimidazole with CHF2)]

or a pharmaceutically acceptable salt, solvate or prodrug thereof;

or stereoisomers, isotopic variants and tautomers thereof.

16. The method according to claim 1, wherein the compound is according to formula B-XIVa, or B-XIVb:

[Structure B-XIVa: benzimidazole-CH2-CH(OH)-CH2-N(diphenyl)]

[Structure B-XIVb: benzimidazole-CH2-CH(OH)-CH2-N(Me)(CH2-phenyl)]

or a pharmaceutically acceptable salt, solvate or prodrug or stereoisomers, isotopic variants and tautomers thereof.

17. The method according to claim 1, wherein the compound is according to formula B-XVa, B-XVb, B-XVc, or B-XVd:

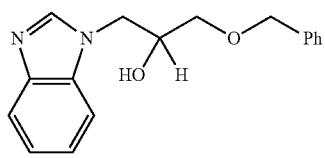
, B-XVa

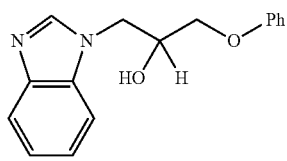
, B-XVb

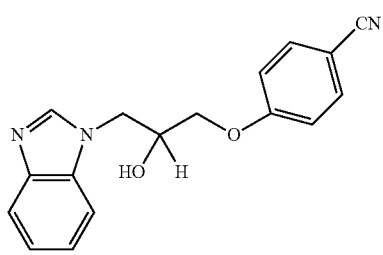
 B-XVc or

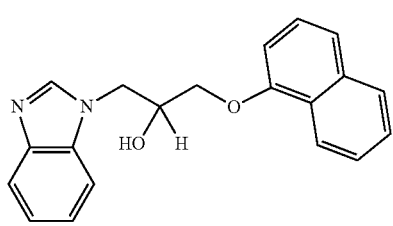
; B-XVd or a pharmaceutically acceptable salt, solvate or prodrug or stereoisomers, isotopic variants and tautomers thereof.

18. The method according to claim 1, wherein the compound is according to formula B-XId, or B-XIIIa.

19. The method of any one of claim 1, 2, or 3, wherein each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, Cl, F, nitro, and thiol.

20. A method for treating or ameliorating in a mammal a disease or condition that is causally related to RAGE activity in vivo, which comprises administering to the mammal an effective disease-treating or condition-treating amount of a compound according to formula B-I':

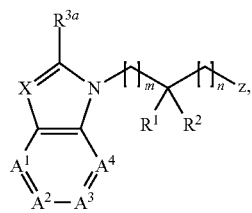
 B-I' wherein
each $A^1$, $A^2$, $A^3$, and $A^4$ is independently $CR^4$ or N; provided that only 1 or 2 of $A^1$, $A^2$, $A^3$, and $A^4$ are N at any one time;
Z is

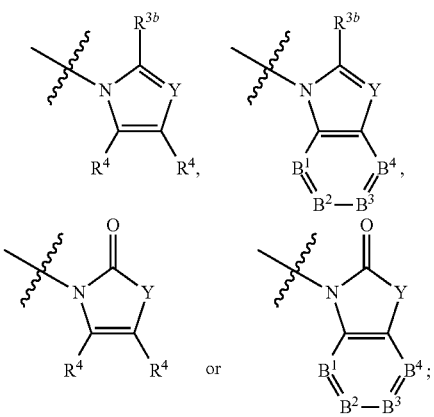

$B^1$, $B^2$, $B^3$, and $B^4$ is independently $CR^4$ or N; Y is $CR^{5b}$ or $NR^{5a}$; $R^{3b}$ is $R^{3a}$; $R^{5b}$ is independently H, substituted or unsubstituted alkyl, substituted or unsubstituted cycloalkyl, substituted or unsubstituted aryl, halo, or cyano; or $R^{5b}$ and $R^{3b}$ may join together to form a substituted or unsubstituted carbocyclic or heterocyclic ring;
X is $CR^{5a}$ or N;
$R^1$ is hydroxy, substituted hydroxyl, amino, or substituted amino;
$R^2$ is H, alkyl or aryl;
$R^{3a}$ is H, substituted or unsubstituted alkyl, substituted or unsubstituted cycloalkyl, substituted or unsubstituted aryl, halo, or cyano;
each $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, F, Cl, nitro, and thiol;

$R^{5a}$ is independently H, substituted or unsubstituted alkyl, substituted or unsubstituted cycloalkyl, substituted or unsubstituted aryl, halo, or cyano; or $R^{5a}$ and $R^{3a}$ may join together to form a substituted or unsubstituted carbocyclic or heterocyclic ring;

and each of the subscript m and n is independently 1, 2, or 3;

or a pharmaceutically acceptable salt, solvate or prodrug thereof;

or stereoisomers, isotopic variants and tautomers thereof;

wherein the disease or condition is selected from diabetes and its complications, atherosclerosis, peripheral vascular disease and associated complications, cardiovascular disease, nephropathy, retinopathy, cardio- and cerebrovascular ischemia/reperfusion injury, heart attack, stroke, myocardial infarction, ischernic cardiomyopathy, cancer, tumor invasion and metastases, acute and chronic inflammation, arthritis, allergy, asthma, obesity, pollution-associated tissue or organ damage, infection, sepsis, pneumonia, liver injury/damage, amyloidoses, skin disorders, skin aging, colitis, lupus, and impaired wound healing.

21. The method according to claim 20, wherein the compound is according to formula B-I:

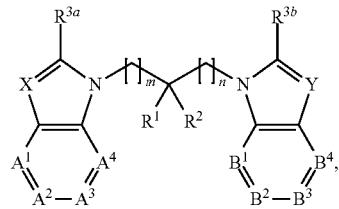

B-I wherein each $A^1$, $A^2$, $A^3$, $A^4$, $B^1$, $B^2$, $B^3$, $B^4$, $R^1$, $R^2$, $R^{3a}$, $R^{3b}$, $R^4$, $R^{5a}$, $R^{5a}$, m, and n are as in claim 20;

or a pharmaceutically acceptable salt, solvate or prodrug thereof; or stereoisomers, isotopic variants and tautomers thereof.

* * * * *

UNITED STATES PATENT AND TRADEMARK OFFICE
CERTIFICATE OF CORRECTION

PATENT NO. : 9,353,078 B2
APPLICATION NO. : 14/503919
DATED : May 31, 2016
INVENTOR(S) : Ann Marie Schmidt et al.

Page 1 of 1

It is certified that error appears in the above-identified patent and that said Letters Patent is hereby corrected as shown below:

In the Specification

Column 1, Line 16:
Please delete "The research leading to the present invention was funded in part by NIH grant 1R24DK103032-01. The United States govrnment has certain rights in the invention."
And insert --This invention was made with government support under R24 DK103032 awarded by the National Institutes of Health. The government has certain rights in the invention.--.

Signed and Sealed this
Fifteenth Day of April, 2025

Coke Morgan Stewart
*Acting Director of the United States Patent and Trademark Office*